US012098366B2

(12) United States Patent
Weiss et al.

(10) Patent No.: US 12,098,366 B2
(45) Date of Patent: Sep. 24, 2024

(54) MUTANT SUBGENOMIC PROMOTER LIBRARY AND USES THEREOF

(71) Applicant: Massachusetts Institute of Technology, Cambridge, MA (US)

(72) Inventors: Ron Weiss, Newton, MA (US); Jin Huh, Watertown, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 337 days.

(21) Appl. No.: 16/784,962

(22) Filed: Feb. 7, 2020

(65) Prior Publication Data

US 2020/0325472 A1 Oct. 15, 2020

Related U.S. Application Data

(60) Provisional application No. 62/831,561, filed on Apr. 9, 2019.

(51) Int. Cl.
*C12N 15/10* (2006.01)
*C12N 15/86* (2006.01)

(52) U.S. Cl.
CPC ..... *C12N 15/1086* (2013.01); *C12N 15/1072* (2013.01); *C12N 15/86* (2013.01)

(58) Field of Classification Search
None
See application file for complete search history.

(56) References Cited

U.S. PATENT DOCUMENTS 6,303,313 B1 * 10/2001 Wigler .................. C07K 16/00 435/6.16

FOREIGN PATENT DOCUMENTS

WO WO 2007/079428 A2 7/2007

OTHER PUBLICATIONS

Frolov et al (J. Virology 73:3854-65) (Year: 1999).*
STN registry excerpt as of May 12, 2000 (Year: 2000).*
Kim et al (Dec. 7, 2017 PLOS One 18 pages) (Year: 2017).*
International Search Report and Written Opinion mailed Jun. 16, 2020 for Application No. PCT/US2020/017196.
[No Author Listed], SIN packaging signal insertion nucleotide sequence. XP002799229. Genseq Database Acession No. ABZ23063. Apr. 11, 2003. 2 pages.
Alper et al., Tuning genetic control through promoter engineering. PNAS. Sep. 6, 2005;102(36):12678-83.
Cobb et al., Directed evolution: an evolving and enabling synthetic biology tool. Curr Opin Chem Biol. Aug. 2012;16(3-4):285-91. doi: 10.1016/j.cbpa.2012.05.186.
Hertz et al., Host-dependent evolution of the sindbis virus promoter for subgenomic mRNA synthesis. J Virology. Dec. 1995;69(12):7775-81.
Wielgosz et al., Sequence requirements for sindbis virus subgenomic mRNA promoter function in cultured cells. J Virology. Apr. 2001;75(8):3509-19.

* cited by examiner

*Primary Examiner* — Christopher M Gross
(74) *Attorney, Agent, or Firm* — Wolf, Greenfield & Sacks, P.C.

(57) ABSTRACT

Disclosed herein is a subgenomic promoter library derived from alphavirus. Also provided herein are methods of using the subgenomic promoters to produce antibodies and other molecules.

20 Claims, 3 Drawing Sheets

Specification includes a Sequence Listing.

SEQUENCE LISTING

```
<160> NUMBER OF SEQ ID NOS: 81

<210> SEQ ID NO 1
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 1

gacttccatc atagttatgg ccatgactac tctagctagc agtgttaaat cattcagcta     60

cctgagaggg gcccctataa ctctctacgg ctaacctgaa tggactacga catagtctag    120

tccgccaagg ccacc                                                     135


<210> SEQ ID NO 2

<400> SEQUENCE: 2

000


<210> SEQ ID NO 3
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 3

gacttccatc atatttatgg ccatgactac tctagctagc agtgttaaat cattcagcta     60

cctgagaggg gcccctataa ctctctacgg ctaacctgaa tggactacga catagtctag    120

tccgccaagg ccacc                                                     135


<210> SEQ ID NO 4
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 4

gacttgatgt cgacatcttt ggtcagaatc accatatcgg cgctcgccac atcctccgca     60

gtcagttcat tttccagacc gattgacccc tgggtttcta cttttacttc ccagcctttc    120

gctttcgcgg cactttccag cgcctctgct gccatttagg tgtgggcaac acc           173


<210> SEQ ID NO 5
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 5
```

-continued

```
gacttccatc atagttatgg ccatgactac tctagctagc agtgtgaaat cattcagcga     60

cctgagaggg gcccctataa ctctctacgg ctaacctgta tggactacga catagtctag    120

tccgccaagg ccacc                                                     135


<210> SEQ ID NO 6
<211> LENGTH: 161
<212> TYPE: DNA
<213> ORGANISM: Artificial Sequence
<220> FEATURE:
<223> OTHER INFORMATION: Synthetic polynucleotide

<400> SEQUENCE: 6

gactcaccca ccaccacagc aacgcgagca ctccatttat cagcgcaggc aaactgtttc     60

taaaagttgc cgccaccgtt gttggtcatc aatttcacgc ccggtagttc atcacgcaga    120

cgctcggcta ttgctatagc cgcagatagt gtatcagcac c                        161


<210> SEQ ID NO 7
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 7

gacttgatgc cgatatctat gaccagaatc gccatatcag cgctcgcctt atcttccgca     60

gtcagttcat tttccggacc aattaattcc tgggtttcca ccttcacttc ccagcctttc    120

gctttcgctg caatatccag cgcctctgct gccatatagg tatgggcaac acc           173


<210> SEQ ID NO 8
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 8

gacttgatgc cgatatcttt ggtcagattc accatatcag cgctcgccac ttcttccgca     60

gtcagttcat tttccagatc aaatgacccc tgggcttcta ctttcacttc ccagcctttc    120

gctttcgcgg cagtttccag cgcctctgct gccatatagg tatgggcaac acc           173


<210> SEQ ID NO 9
<211> LENGTH: 136
<212> TYPE: DNA
<213> ORGANISM: Artificial Sequence
<220> FEATURE:
<223> OTHER INFORMATION: Synthetic polynucleotide

<400> SEQUENCE: 9

gacttccatc atagttatgg ccatgactac tctagatagc agtgttaaat cattcagcta     60

cctgagaggg ggcccctata actctctacg gctaacctta ttggactacg acatagtcta    120

gctcgccaag gccacc                                                    136


<210> SEQ ID NO 10
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 10
```

gacttccatc atagttatgg ccatgactac tctagctatc agtgttaaat cattcagcta 60
cctgagaggg gcccctataa ctctctacgg ctaacctgaa tggactacaa catagtctag 120
tccgccaagg ccacc 135

<210> SEQ ID NO 11
<211> LENGTH: 161
<212> TYPE: DNA
<213> ORGANISM: Artificial Sequence
<220> FEATURE:
<223> OTHER INFORMATION: Synthetic polynucleotide

<400> SEQUENCE: 11
gactcatcca gcaccacagc aacgcgggta ccccatttat cagcacgggc gaactgtttc 60
ttgaagttgc caccgccaag gttggtcatc aatttcacgc ccggtaactc atcacgcaga 120
cactcagcta atgccatagc cgcagattgt gtatcagcac c 161

<210> SEQ ID NO 12
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 12
gacttgatgc cgatatcttt gatcagtatc accttatcaa cgctagccac aacttccgca 60
gtcagtgatt tttccagacc aattgacccc agggtttcta ctttcacttc cctgcctttc 120
gcattcccgg cactttccag cgcctctact gcaatatagg tatgggcaac acc 173

<210> SEQ ID NO 13
<211> LENGTH: 134
<212> TYPE: DNA
<213> ORGANISM: Artificial Sequence
<220> FEATURE:
<223> OTHER INFORMATION: Synthetic polynucleotide

<400> SEQUENCE: 13
gacttccatc atagatatgg ccatgactac tctagctagc agtgttaaat ctttcagcta 60
cctgagaggg cccccataac tctctacgga taacctgaat ggactacgac atagtctggt 120
ccgccaaggc cacc 134

<210> SEQ ID NO 14

<400> SEQUENCE: 14

000

<210> SEQ ID NO 15
<211> LENGTH: 174
<212> TYPE: DNA
<213> ORGANISM: Artificial Sequence
<220> FEATURE:
<223> OTHER INFORMATION: Synthetic polynucleotide

<400> SEQUENCE: 15
gacttgatgc cgatatcttt ggtcagaatc accatatcag cgctcgccac atcttcctgt 60
agtcagttca tttccctgac catttgaccc ctgggtttct attctcactt cccagccttt 120
cgcttttgca gcactttctg gcgcctctgc agccgtatag gtatgggcaa cacc 174

<210> SEQ ID NO 16
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 16
gacttccatc atagttatgg ccgtgactac tctagctagc agtgttaaat cattcagcta 60
cctgagaggg gcccctaaaa ctctctaccg ctaacctgaa tggactacta catagtctaa 120
tccgccaagg ccacc 135

<210> SEQ ID NO 17
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 17
gacttccatc atagttatgg ccatgactac tctagctagc agtgttaaat cattcagcta 60
cctgagaggg gcccctataa ctctctacgg ctaacctgaa tggactacga catagtctag 120
tcagccaagg ccacc 135

<210> SEQ ID NO 18
<211> LENGTH: 134
<212> TYPE: DNA
<213> ORGANISM: Artificial Sequence
<220> FEATURE:
<223> OTHER INFORMATION: Synthetic polynucleotide

<400> SEQUENCE: 18
gacttccatc atagttacgg ccatgactcc tcaagcaagc agtgttagat cattcagcta 60
cctgagaggg accctataac tctctacggc taacctgaat ggtcttcgac atagtctaga 120
ccgccgaggc cacc 134

<210> SEQ ID NO 19
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 19
gacttccatc atagttatgg ccatgactac tctagctagc agtgttaaat cattcagcta 60
cctgagaggg gcccctataa ctctctacgg ctaacctgaa tggactacga catagtctag 120
tccgccaagg ccacc 135

<210> SEQ ID NO 20
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 20
gacttgatgc cgttatcttt ggtcagaatc accatatcag cgtttgcctc atctcccgca 60
gtcagttcat tttccagacc aattgacccc tgggtttcta ctttcacttc ccagcctttc 120
gctttcgcgg cactttccag cgcctctgct gccatattgg tatgggcaac acc 173

<210> SEQ ID NO 21
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 21
gacttccatc atagttatgg ccatgactat tctagctagc agtgataaat cattcagcta 60
cctgagaggg gcccctataa ctctctacgg ctaacctgaa tggactacga catagtctag 120
cccgccaagg ccacc 135

<210> SEQ ID NO 22
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 22
gacttccatc atagttatgg ccatgactac tctagctagc agtgttaaat cattcagcta 60
cctgagaggg gcccctataa ctctctacag ctaacctgaa tggactacga catagtctag 120
tccgccaagg ccacc 135

<210> SEQ ID NO 23

<400> SEQUENCE: 23

000

<210> SEQ ID NO 24
<211> LENGTH: 172
<212> TYPE: DNA
<213> ORGANISM: Artificial Sequence
<220> FEATURE:
<223> OTHER INFORMATION: Synthetic polynucleotide

<400> SEQUENCE: 24
gacttgatgc cgatatcatt agtcaaaatc accaaatcag cgctcgccac atcttccgca 60
gtcagatcat tttccagacc aattgacccc tgggtttcta ctttcacttc cagcctttcg 120
ctttcgcggc actttccagc gcttctgctg ccatataggt atgggcagca cc 172

<210> SEQ ID NO 25
<211> LENGTH: 160
<212> TYPE: DNA
<213> ORGANISM: Artificial Sequence
<220> FEATURE:
<223> OTHER INFORMATION: Synthetic polynucleotide

<400> SEQUENCE: 25
gactcaccca gcatcacagc atcgcgggcc ccccatttat cagcacggta aacagtttct 60
taaagctgtc gccgccgtgg ttggtcatca attccacgcc cggtaattcg tcatgcagac 120
gctcatctaa tgccatagcc gctgattgtg tatcagcacc 160

<210> SEQ ID NO 26
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 26
gacttgatgt cgatatcttt ggtcagaatc accatatcag cgctcgccac atcttccgca 60
atcagttcat tttccagacc aattgatgcc tgggtttcta ctttcacttc ccagcctttc 120
gctttcgcgg cacttttcag cgcctctgct gccatatagg tatgggcaac acc 173

<210> SEQ ID NO 27
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 27
gacttccatc atagttatgg ccatgactac tctacctagc agtgttaaat cattcagcta 60
cctgagaggg gcccctataa ctctctacgg ctaacctgaa tggactacga catagtctag 120
tccgccaagg ccacc 135

<210> SEQ ID NO 28
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 28
gacttcaatc atagtcatgg ctatgactac tccagctagc agtgttaaat cattcagcta 60
cctgggagtg gcccctataa ctctctacgg ctaacctgaa tggactacga catagtctag 120
ttcgccaagg ccacc 135

<210> SEQ ID NO 29
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 29
gacttccatc atagttatga ccatgactac tctagctagc agtgttaaat cattcagcta 60
cctgagaggg gcccctataa ctctctacgg ctaacctgaa tggactacga catagtctag 120
cccgccaagg ccacc 135

<210> SEQ ID NO 30
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 30
gacttccatc atagttttgg ccatgactac tctagctagc agtgttaaat cattcagcta 60
cctgagaggg gcccctataa ctctttacgg ctaacctgaa tggactacga catagtctag 120
tccgccaagg ccacc 135

<210> SEQ ID NO 31
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 31
gacttccatc atagttatgg ccatgactac tctagctagc agtgttaaat cattcagcta 60
cctgagaggg gcccctataa ctctttacgg ctaacctgaa tggactacga catagtctag 120
tccgccaagg ccacc 135

<210> SEQ ID NO 32
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 32
gacttccatc ttagttatgg ccatgactac tctagctagc agtgttaaat cattcagcta 60
cctgagaggg gcccttataa ctctctactg ctaacctgaa tggactacga catagtctag 120
tccgccaagg ccacc 135

<210> SEQ ID NO 33
<211> LENGTH: 171
<212> TYPE: DNA
<213> ORGANISM: Artificial Sequence
<220> FEATURE:
<223> OTHER INFORMATION: Synthetic polynucleotide

<400> SEQUENCE: 33
gacttgatgc cgatatcttt ggcagaatca ccatatcagc gctcgcacat cttccgcagt 60
cagttcatta tccagactga ttgacccctg ggtttctact ttcacttccc agcctttcgc 120
cttcgcggca ctttccagcg cctctgctgc catataggta tgggcaacac c 171

<210> SEQ ID NO 34
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 34
gacttccatc atagttacgg ccatgactac tcgagctagc agtgttaaat cattcagcta 60
cctgagaggg gaccttttaa ctctctacgg ctaacctgta tggactacga caaagtctag 120
tcagccaagg ccacc 135

<210> SEQ ID NO 35
<211> LENGTH: 171
<212> TYPE: DNA
<213> ORGANISM: Artificial Sequence
<220> FEATURE:
<223> OTHER INFORMATION: Synthetic polynucleotide

<400> SEQUENCE: 35
gacttgatgc cgatatcttt ggcagaatca ccatatcagc gctcgcacat cttccgcagt 60
cagttcatta tccagactga ttgacccctg ggtttctact ttcacttccc agcctttcgc 120
cttcgcggca ctttccagcg cctctgctgc catataggta tgggcaacac c 171

<210> SEQ ID NO 36
<211> LENGTH: 135
<212> TYPE: DNA
<213> ORGANISM: Artificial Sequence
<220> FEATURE:

<223> OTHER INFORMATION: Synthetic polynucleotide

<400> SEQUENCE: 36
gacttccatc atagttatgg ccatgactac tctagctagc agtgttagat cattcagcca 60
cctgagaggg gcccctaaaa ctctctacgg ctgacctgaa tggactacga catagtttag 120
ttcaccaagg ccacc 135

<210> SEQ ID NO 37
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 37
gacttccatc atagttatgg ccatgactac tctagctagc agtgttaaat cattcagcta 60
cctgagaggg acccctatga ctctctacgg ctaacctgaa tggactacga catagtctag 120
tcagccaagg ccacc 135

<210> SEQ ID NO 38
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 38
gacttccatc atagttatgg ccatgactac tctagctagc agtgttaaat cattcagcta 60
cctgagaggg gcccctataa ctctctacgg ctaacctgaa gagcgcttcc tcaggccacc 120

<210> SEQ ID NO 39
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 39
gacttccatc atagttatgg ccatgactac tctagctagc agtgttaaat cattcagcta 60
cctgagatgg gcccctataa ctctctacgg ctaacctgaa tggactacga catagtctag 120
tccgccaagg ccacc 135

<210> SEQ ID NO 40
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 40
gacttccatc atcgttatgg ccatggctac tctagctagc agtgttaaat cattcagcta 60
cctgagaggg gcccctataa ctctctacgt ctaaccggaa tggactacga catagtctag 120
tccgccaagc ccacc 135

<210> SEQ ID NO 41

<400> SEQUENCE: 41

000

<210> SEQ ID NO 42

<400> SEQUENCE: 42

000

<210> SEQ ID NO 43
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 43
gacttgatgc cgatatcttt ggtcagaatc accatatcag cgctcgccac atcttccgca 60
gtcagttcat tttctagacc aattgacccc tgggtttcta ctttcacttc ccagcctttc 120
gctttcgcgg cactttccag cgcctctgct gccatatagg tatgggcaac acc 173

<210> SEQ ID NO 44
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 44
gacttccatc atagttatgg ccatgactac tctagctagc agtgttaaat cattcagcta 60
cctgagaggg gcccctataa ctctctacgg ctaacctgaa tggactacta catagtctag 120
tccgccaagg ccacc 135

<210> SEQ ID NO 45

<400> SEQUENCE: 45

000

<210> SEQ ID NO 46
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 46
gacttgatgc cgatatcctt gctcaggatc accgtatcag cgctcgccac atcttcggca 60
gtcagttcat tttccatacc aactggcccc tgggtttcta ctttcgcgtc ccagcctttc 120
gctttcgtgg cactttccag catctctgct gccatatagg tatgtgcaac acc 173

<210> SEQ ID NO 47
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 47
gacttccatc atagttatgg ccatgactac tctagctagt agtgttaaat cattcagcta 60
cctgagaggg gcccctataa ctctctacgg ctaacctgaa tggactacga catagtctag 120
tccgccaagg ccacc 135

<210> SEQ ID NO 48
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 48
gacttccatc atagttatgg ccatgactac tctagctagc agtgttgaat cattcagcta 60
cctgagaggg gcccctataa ctctctacgg ctaacctgaa cggactacga catagtctag 120
tccgccaagg ccacc 135

<210> SEQ ID NO 49
<211> LENGTH: 134
<212> TYPE: DNA
<213> ORGANISM: Artificial Sequence
<220> FEATURE:
<223> OTHER INFORMATION: Synthetic polynucleotide

<400> SEQUENCE: 49
gacttccatc atagttatgg ccatgactac tctagctagc agtgtaaatc attcagctac 60
ctgagagggg cccctataac tctctacggc taacctgaat gcactacgac atagtctagt 120
ccgcacaggc cacc 134

<210> SEQ ID NO 50
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 50
gacttccatc atagttatgg ccatgactac tctagctagc agtgttaaat cattcagcta 60
cctgagaggg gcccctataa ctctctacgg ctaacctgga tggactacga catagtctag 120
tccgccaagg ccacc 135

<210> SEQ ID NO 51

<400> SEQUENCE: 51

000

<210> SEQ ID NO 52
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 52
gacttgacgc cgacatctat ggtcagaacc accaaatcag tgctcgcctc atcttctgca 60
gtaagttcat tttccagacc aatcgacccc tgggtttctt ctttctcttc ccagcctttc 120
gctttcgcgg cactttccag cgcccctgct gccatatagg catgggttac acc 173

<210> SEQ ID NO 53
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 53
gacttccatc atagttatgg ccatgactac tctagctagc agtgttaaat cattcagcta 60
cctgagaggg gcccctataa ctctctatgg ctaacctgaa tggactacga cttagtctag 120
tccgccatgg ccacc 135

<210> SEQ ID NO 54
<211> LENGTH: 159
<212> TYPE: DNA
<213> ORGANISM: Artificial Sequence
<220> FEATURE:
<223> OTHER INFORMATION: Synthetic polynucleotide

<400> SEQUENCE: 54
gacttccagc atagttatcg ccaagactac tctagctagc attgttaaat cattcagcta 60
cctgagaggg gcccctataa ctctctacgg ctaacctgaa tggactacga cattgtctag 120
tccgccaagg ccacctgaag agcgcttcct cagcccacc 159

<210> SEQ ID NO 55
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 55
gacttccatc atagttatgg ccatgactac tctagctagc agtgttaaat cattcagcta 60
cctgagaggg gcccctataa ctctctacgg ctagcctgaa tggactacga catagtctag 120
tccgccaagg ccacc 135

<210> SEQ ID NO 56
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 56
gacttccatc atagttatgg ccatgactac tctagctagc agtgttaaat cattcagcta 60
cctgaggggg gcccctataa ctctctacgg ctaacctgaa tggactacga catagtctag 120
tccgccaagg ccacc 135

<210> SEQ ID NO 57

<400> SEQUENCE: 57

000

<210> SEQ ID NO 58
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 58
gacttgatgc aggtatcttt ggtcggaacc accatatcaa cgctctccac atcctccgca 60
gtcagcacat tatccagacc aattgacccc tgtgtttcta ctatctcttc cccacctttc 120
gctttcgcgg cgctttcctg cgcctctgcc gccatatagg tatgggcaac acc 173

<210> SEQ ID NO 59
<211> LENGTH: 134
<212> TYPE: DNA
<213> ORGANISM: Artificial Sequence
<220> FEATURE:
<223> OTHER INFORMATION: Synthetic polynucleotide

<400> SEQUENCE: 59
gacttccatc atagttatgg ccatgactac tctagctagc agagttaatc attcagctac 60
ctgagagggg cccctataac tctctacggc aaacctgaat ggactacgac atagtctagt 120
ccgccaaggc cacc 134

<210> SEQ ID NO 60
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 60
gacttccatc atagttatgg ccatgactac tctagctagc agtgttaaat cattcagctt 60
cctgagaggg gcccctataa ctctctacgg ctaacctgaa tggactacga catagtctag 120
tccgccaagg ccacc 135

<210> SEQ ID NO 61
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 61
gacttccatc atagttatgg ccatgactac tctagctagc agtgttaaat cattcagcta 60
cctgagaggg gcccctataa ctctctacgg ctaacctgaa aggtctacga catagtctag 120
tccgccaagg ccacc 135

<210> SEQ ID NO 62
<211> LENGTH: 134
<212> TYPE: DNA
<213> ORGANISM: Artificial Sequence
<220> FEATURE:
<223> OTHER INFORMATION: Synthetic polynucleotide

<400> SEQUENCE: 62
gacttccatc atagttacgg ccatgaccac tatagctagc agtgttaaat cattaagcta 60
cctaagaggg gccccttaa ctatatacgg ctaacctgaa gggctacgac atagtctagt 120
ccgccaaggc cacc 134

<210> SEQ ID NO 63
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 63
gacttccatc atagttatgc ccttgactac tctagctagc agtgttaaat cattcagcta 60
cctgagaggg gcccctataa ctctctacgg ctaacctgaa tggactacga catagtctag 120
tccgccaagg ccacc 135

<210> SEQ ID NO 64
<211> LENGTH: 161
<212> TYPE: DNA
<213> ORGANISM: Artificial Sequence
<220> FEATURE:
<223> OTHER INFORMATION: Synthetic polynucleotide

<400> SEQUENCE: 64
gactcaccca gcaccacagc aacacgggct acccattcat cagcctgggc agactgtttc 60
ttaaagttgc cgacgccgcg cttggtcatc aatctcacgt ccggtaattc atcactcaga 120
cgctctgcta atgccatagc cgcagattgt gtatcagcac c 161

<210> SEQ ID NO 65
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 65
gacttgatgc cgatatctat ggtcaggatc accattacgt cgctcgccac atctttcgca 60
gtcagttcat tttccaggcc tattgacccc tgggtttcta ttatcacttc ccatcctttc 120
gcattcgcgg tactttccag cgcctctgcc gccaaatagg tgtagactac acc 173

<210> SEQ ID NO 66
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 66
gacttccatc ataattaagg ccatgactac tcaagctagc agtgttaaat cgttcagtcg 60
cctaagaggg gacactttaa ctctctacgg ctaacctgta tcgactacga cttagtctag 120
tctgccaagg ccacc 135

<210> SEQ ID NO 67
<211> LENGTH: 172
<212> TYPE: DNA
<213> ORGANISM: Artificial Sequence
<220> FEATURE:
<223> OTHER INFORMATION: Synthetic polynucleotide

<400> SEQUENCE: 67
gacttgatgc cgatatcttc ggtcagaatc accatatcag cgctcacaac atcttcacca 60
gtcagtagat tttccagacc aattgacccg tgggcttcta ctttcacttc ccagcctttc 120
gctttcgcgg cactttccag cgcctctgct gcctataggc atgggcaaca cc 172

<210> SEQ ID NO 68
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 68
gacttgatgc cgatatctct ggtcagaatc accatatcag cgctcgccat atcttccgca 60
gtcagttcat tttccaaacc aattgaccca tgggtttcta ccttcacttc ccagcctttc 120
gctttcgcgg cactttccag cgcctctgct gccatatagt tatgggcaac acc 173

<210> SEQ ID NO 69
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 69
gacttccatc atagttacgg ccacgtctac tctagcttgc agtgtcaaat caatcagcca 60
cc 62

<210> SEQ ID NO 70
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 70
gacttccatc atagttatgg ccatgactac tctagctagc aatgttaaat cattcagcta 60
cctgagaggg gcccctataa ctctctacgg ctaacctgca tggactacga catagtctag 120
tccgccaagg ccacc 135

<210> SEQ ID NO 71
<211> LENGTH: 196
<212> TYPE: DNA
<213> ORGANISM: Artificial Sequence
<220> FEATURE:
<223> OTHER INFORMATION: Synthetic polynucleotide

<400> SEQUENCE: 71
gacttgatga cgatatcttt ggtcggaatc accatatcaa tgctcgccac atcttccgcg 60
gtaagttcat cttccagaca attgacccct gggttactac tatcacttcc ctgccttacg 120
ctttgcggca cttaccagcg cctccattgc catataggaa tgggcaacac ctgaagagcg 180
cttcgtcgag gccacc 196

<210> SEQ ID NO 72
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 72
gacttccatc atagatatgg ccaagactag tctagctatt agtgataaat cattcaacta 60
cctgagaggg gcccccatta ctcactacgg ctaacctgaa cggagtacgg cattgtctag 120
tctgccaagg ccacc 135

<210> SEQ ID NO 73
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 73
gacttccatc atagttatgg ccatgactac tctagctagc agtgttgaat cattcagcta 60
cctgagaggg gcccctataa ctctctacgg ctaacctgaa tggactacga catagtctag 120
tccgccaagg ccacc 135

<210> SEQ ID NO 74
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 74
gacttgatgc cgatatctta ggtcagaatc accatatcag tgatcgcaac atcttccgca 60
gacaattcat tttccaaacc aattgacccc tgggtttcta ctttcgcttc tcagcctttc 120
gctttcgcgg cactttccag cgcctctgct gtcataaagg tatgggcaac acc 173

<210> SEQ ID NO 75
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 75 gccacc 6

<210> SEQ ID NO 76
<211> LENGTH: 151
<212> TYPE: DNA
<213> ORGANISM: Artificial Sequence
<220> FEATURE:
<223> OTHER INFORMATION: Synthetic polynucleotide

<400> SEQUENCE: 76
gctcttcaga cttccatcat agttatggcc atgactactc tagctagcag tgttaaatca 60
ttcagctacc tgagaggggc ccctataact ctctacggct aacctgaatg gactacgaca 120
tagtctagtc cgccaaggcc acctgaagag c 151

<210> SEQ ID NO 77
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 77
tattgggcgc tcttcagact 20

<210> SEQ ID NO 78
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 78
gaggaagcgc tcttcaggtg 20

<210> SEQ ID NO 79
<211> LENGTH: 13
<212> TYPE: RNA
<213> ORGANISM: Artificial Sequence
<220> FEATURE:
<223> OTHER INFORMATION: Synthetic polynucleotide

<400> SEQUENCE: 79
gccgccrcca ugg 13

<210> SEQ ID NO 80
<211> LENGTH: 181
<212> TYPE: DNA
<213> ORGANISM: Artificial Sequence
<220> FEATURE:
<223> OTHER INFORMATION: Synthetic polynucleotide

<400> SEQUENCE: 80
gacttccatc atacgttatg gccatgacta ctctagctag cagtgttaaa tcattcagct 60
acctgagagg ggcccctata actctctacg gctaacctga atggactacg acatagtcta 120
gtccgccaag gccaccatat aggtatgggc aacaccyrmm gagcgcttcg tcgaggccac 180
c 181

<210> SEQ ID NO 81
<211> LENGTH: 238
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (5)..(5)
<223> OTHER INFORMATION: Position 5 to 5 may be absent, if present n is C.
<220> FEATURE:
<221> NAME/KEY: misc_feature
<222> LOCATION: (6)..(6)
<223> OTHER INFORMATION: Position 6 to 6 may be absent, if present n is A.
<220> FEATURE:
<221> NAME/KEY: misc_feature
<222> LOCATION: (7)..(7)
<223> OTHER INFORMATION: n is T or C.
<220> FEATURE:
<221> NAME/KEY: misc_feature
<222> LOCATION: (8)..(8)
<223> OTHER INFORMATION: n is  C or G.
<220> FEATURE:
<221> NAME/KEY: misc_feature
<222> LOCATION: (9)..(9)
<223> OTHER INFORMATION: n is C or A.
<220> FEATURE:
<221> NAME/KEY: misc_feature
<222> LOCATION: (10)..(10)
<223> OTHER INFORMATION: n is C, T or A.
<220> FEATURE:
<221> NAME/KEY: misc_feature
<222> LOCATION: (11)..(11)
<223> OTHER INFORMATION: n is T, G or C.
<220> FEATURE:
<221> NAME/KEY: misc_feature
<222> LOCATION: (12)..(12)
<223> OTHER INFORMATION: n is C, T or A.
<220> FEATURE:
<221> NAME/KEY: misc_feature
<222> LOCATION: (13)..(13)
<223> OTHER INFORMATION: Position 13 to 13 may be absent, if present n is C or A.
<220> FEATURE:
<221> NAME/KEY: misc_feature
<222> LOCATION: (14)..(14)
<223> OTHER INFORMATION: Position 14 to 14 may be absent, if present n is G.
<220> FEATURE:
<221> NAME/KEY: misc_feature
<222> LOCATION: (15)..(15)
<223> OTHER INFORMATION: Position 15 to 15 may be absent, if present n is T, A or G.
<220> FEATURE:
<221> NAME/KEY: misc_feature

```
<222> LOCATION: (16)..(16)
<223> OTHER INFORMATION: Position 16 to 16 may be absent, if present n
      is T or C.
<220> FEATURE:
<221> NAME/KEY: misc_feature
<222> LOCATION: (17)..(17)
<223> OTHER INFORMATION: Position 17 to 17 may be absent, if present n
      is A or C.
<220> FEATURE:
<221> NAME/KEY: misc_feature
<222> LOCATION: (18)..(18)
<223> OTHER INFORMATION: n is G, T or A.
<220> FEATURE:
<221> NAME/KEY: misc_feature
<222> LOCATION: (19)..(19)
<223> OTHER INFORMATION: n is T, A or C.
<220> FEATURE:
<221> NAME/KEY: misc_feature
<222> LOCATION: (20)..(20)
<223> OTHER INFORMATION: n is T, C or A.
<220> FEATURE:
<221> NAME/KEY: misc_feature
<222> LOCATION: (21)..(21)
<223> OTHER INFORMATION: n is A, T or C.
<220> FEATURE:
<221> NAME/KEY: misc_feature
<222> LOCATION: (22)..(22)
<223> OTHER INFORMATION: n is T, C or A.
<220> FEATURE:
<221> NAME/KEY: misc_feature
<222> LOCATION: (23)..(23)
<223> OTHER INFORMATION: n is G, C or A.
<220> FEATURE:
<221> NAME/KEY: misc_feature
<222> LOCATION: (24)..(24)
<223> OTHER INFORMATION: n is G, C or A.
<220> FEATURE:
<221> NAME/KEY: misc_feature
<222> LOCATION: (25)..(25)
<223> OTHER INFORMATION: Position 25 to 25 may be absent, if present n
      is C or T.
<220> FEATURE:
<221> NAME/KEY: misc_feature
<222> LOCATION: (26)..(26)
<223> OTHER INFORMATION: Position 26 to 26 may be absent, if present n
      is A.
<220> FEATURE:
<221> NAME/KEY: misc_feature
<222> LOCATION: (27)..(27)
<223> OTHER INFORMATION: Position 27 to 27 may be absent, if present n
      is A or T.
<220> FEATURE:
<221> NAME/KEY: misc_feature
<222> LOCATION: (28)..(28)
<223> OTHER INFORMATION: n is C or T.
<220> FEATURE:
<221> NAME/KEY: misc_feature
<222> LOCATION: (29)..(29)
<223> OTHER INFORMATION: n is A, T or G.
<220> FEATURE:
<221> NAME/KEY: misc_feature
<222> LOCATION: (30)..(30)
<223> OTHER INFORMATION: n is T, A, C, or G.
<220> FEATURE:
<221> NAME/KEY: misc_feature
<222> LOCATION: (31)..(31)
<223> OTHER INFORMATION: n is G, T or A.
<220> FEATURE:
<221> NAME/KEY: misc_feature
<222> LOCATION: (32)..(32)
<223> OTHER INFORMATION: n is A, G, or T.
<220> FEATURE:
<221> NAME/KEY: misc_feature
<222> LOCATION: (33)..(33)
<223> OTHER INFORMATION: n is C, T, or G.
<220> FEATURE:
<221> NAME/KEY: misc_feature
<222> LOCATION: (34)..(34)
<223> OTHER INFORMATION: n is T, C or A.
```

<220> FEATURE:
<221> NAME/KEY: misc_feature
<222> LOCATION: (35)..(35)
<223> OTHER INFORMATION: n is A, C or G.
<220> FEATURE:
<221> NAME/KEY: misc_feature
<222> LOCATION: (36)..(36)
<223> OTHER INFORMATION: n is C, T, or G.
<220> FEATURE:
<221> NAME/KEY: misc_feature
<222> LOCATION: (37)..(37)
<223> OTHER INFORMATION: n is T, C or A.
<220> FEATURE:
<221> NAME/KEY: misc_feature
<222> LOCATION: (38)..(38)
<223> OTHER INFORMATION: n is C, A, G or T.
<220> FEATURE:
<221> NAME/KEY: misc_feature
<222> LOCATION: (39)..(39)
<223> OTHER INFORMATION: n is T, C, G or A.
<220> FEATURE:
<221> NAME/KEY: misc_feature
<222> LOCATION: (40)..(40)
<223> OTHER INFORMATION: n is A, T or G.
<220> FEATURE:
<221> NAME/KEY: misc_feature
<222> LOCATION: (41)..(41)
<223> OTHER INFORMATION: Position 41 to 41 may be absent, if present n
is T or A.
<220> FEATURE:
<221> NAME/KEY: misc_feature
<222> LOCATION: (42)..(42)
<223> OTHER INFORMATION: Position 42 to 42 may be absent, if present n
is C or T.
<220> FEATURE:
<221> NAME/KEY: misc_feature
<222> LOCATION: (43)..(43)
<223> OTHER INFORMATION: Position 43 to 43 may be absent, if present n
is A, G or T.
<220> FEATURE:
<221> NAME/KEY: misc_feature
<222> LOCATION: (44)..(44)
<223> OTHER INFORMATION: Position 44 to 44 may be absent, if present n
is G, A or T.
<220> FEATURE:
<221> NAME/KEY: misc_feature
<222> LOCATION: (45)..(45)
<223> OTHER INFORMATION: Position 45 to 45 may be absent, if present n
is C or T.
<220> FEATURE:
<221> NAME/KEY: misc_feature
<222> LOCATION: (46)..(46)
<223> OTHER INFORMATION: n is G, C or A.
<220> FEATURE:
<221> NAME/KEY: misc_feature
<222> LOCATION: (47)..(47)
<223> OTHER INFORMATION: n is C, A or T.
<220> FEATURE:
<221> NAME/KEY: misc_feature
<222> LOCATION: (48)..(48)
<223> OTHER INFORMATION: n is T, A or C.
<220> FEATURE:
<221> NAME/KEY: misc_feature
<222> LOCATION: (49)..(49)
<223> OTHER INFORMATION: n is A, T or C.
<220> FEATURE:
<221> NAME/KEY: misc_feature
<222> LOCATION: (50)..(50)
<223> OTHER INFORMATION: n is G, T, A or C.
<220> FEATURE:
<221> NAME/KEY: misc_feature
<222> LOCATION: (51)..(51)
<223> OTHER INFORMATION: n is C or T.
<220> FEATURE:
<221> NAME/KEY: misc_feature
<222> LOCATION: (52)..(52)
<223> OTHER INFORMATION: Position 52 to 52 may be absent, if present n
is C or A.
<220> FEATURE:

```
<221> NAME/KEY: misc_feature
<222> LOCATION: (53)..(53)
<223> OTHER INFORMATION: Position 53 to 53 may be absent, if present n
      is A or T.
<220> FEATURE:
<221> NAME/KEY: misc_feature
<222> LOCATION: (54)..(54)
<223> OTHER INFORMATION: Position 54 to 54 may be absent, if present n
      is C or T.
<220> FEATURE:
<221> NAME/KEY: misc_feature
<222> LOCATION: (55)..(55)
<223> OTHER INFORMATION: Position 55 to 55 may be absent, if present n
      is A or T.
<220> FEATURE:
<221> NAME/KEY: misc_feature
<222> LOCATION: (56)..(56)
<223> OTHER INFORMATION: Position 56 to 56 may be absent, if present n
      is T or A.
<220> FEATURE:
<221> NAME/KEY: misc_feature
<222> LOCATION: (57)..(57)
<223> OTHER INFORMATION: Position 57 to 57 may be absent, if present n
      is C.
<220> FEATURE:
<221> NAME/KEY: misc_feature
<222> LOCATION: (58)..(58)
<223> OTHER INFORMATION: Position 58 to 58 may be absent, if present n
      is T or C.
<220> FEATURE:
<221> NAME/KEY: misc_feature
<222> LOCATION: (59)..(59)
<223> OTHER INFORMATION: Position 59 to 59 may be absent, if present n
      is T or C.
<220> FEATURE:
<221> NAME/KEY: misc_feature
<222> LOCATION: (60)..(60)
<223> OTHER INFORMATION: Position 60 to 60 may be absent, if present n
      is C.
<220> FEATURE:
<221> NAME/KEY: misc_feature
<222> LOCATION: (61)..(61)
<223> OTHER INFORMATION: Position 61 to 61 may be absent, if present n
      is C, T, G or A.
<220> FEATURE:
<221> NAME/KEY: misc_feature
<222> LOCATION: (62)..(62)
<223> OTHER INFORMATION: Position 62 to 62 may be absent, if present n
      is T.
<220> FEATURE:
<221> NAME/KEY: misc_feature
<222> LOCATION: (63)..(63)
<223> OTHER INFORMATION: Position 63 to 63 may be absent, if present n
      is A, G or C.
<220> FEATURE:
<221> NAME/KEY: misc_feature
<222> LOCATION: (64)..(64)
<223> OTHER INFORMATION: Position 64 to 64 may be absent, if present n
      is G, A, T, C.
<220> FEATURE:
<221> NAME/KEY: misc_feature
<222> LOCATION: (65)..(65)
<223> OTHER INFORMATION: Position 65 to 65 may be absent, if present n
      is T, A, or G.
<220> FEATURE:
<221> NAME/KEY: misc_feature
<222> LOCATION: (66)..(66)
<223> OTHER INFORMATION: Position 66 to 66 may be absent, if present n
      is G or A.
<220> FEATURE:
<221> NAME/KEY: misc_feature
<222> LOCATION: (67)..(67)
<223> OTHER INFORMATION: Position 67 to 67 may be absent, if present n
      is T, A, or G.
<220> FEATURE:
<221> NAME/KEY: misc_feature
<222> LOCATION: (68)..(68)
<223> OTHER INFORMATION: Position 68 to 68 may be absent, if present n
      is T, G, C, or A.
```

<220> FEATURE:
<221> NAME/KEY: misc_feature
<222> LOCATION: (69)..(69)
<223> OTHER INFORMATION: Position 69 to 69 may be absent, if present n is A or G.
<220> FEATURE:
<221> NAME/KEY: misc_feature
<222> LOCATION: (70)..(70)
<223> OTHER INFORMATION: Position 70 to 70 may be absent, if present n is A or G.
<220> FEATURE:
<221> NAME/KEY: misc_feature
<222> LOCATION: (71)..(71)
<223> OTHER INFORMATION: Position 71 to 71 may be absent, if present n is A, T, or C.
<220> FEATURE:
<221> NAME/KEY: misc_feature
<222> LOCATION: (72)..(72)
<223> OTHER INFORMATION: Position 72 to 72 may be absent, if present n is T, A, C or G.
<220> FEATURE:
<221> NAME/KEY: misc_feature
<222> LOCATION: (73)..(73)
<223> OTHER INFORMATION: Position 73 to 73 may be absent, if present n is C, T, G or A.
<220> FEATURE:
<221> NAME/KEY: misc_feature
<222> LOCATION: (74)..(74)
<223> OTHER INFORMATION: Position 74 to 74 may be absent, if present n is A, T or G.
<220> FEATURE:
<221> NAME/KEY: misc_feature
<222> LOCATION: (75)..(75)
<223> OTHER INFORMATION: Position 75 to 75 may be absent, if present n is T or A.
<220> FEATURE:
<221> NAME/KEY: misc_feature
<222> LOCATION: (76)..(76)
<223> OTHER INFORMATION: Position 76 to 76 may be absent, if present n is T or C.
<220> FEATURE:
<221> NAME/KEY: misc_feature
<222> LOCATION: (77)..(77)
<223> OTHER INFORMATION: Position 77 to 77 may be absent, if present n is C, A or T.
<220> FEATURE:
<221> NAME/KEY: misc_feature
<222> LOCATION: (78)..(78)
<223> OTHER INFORMATION: Position 78 to 78 may be absent, if present n is A, T or C.
<220> FEATURE:
<221> NAME/KEY: misc_feature
<222> LOCATION: (79)..(79)
<223> OTHER INFORMATION: Position 79 to 79 may be absent, if present n is G, A, C or T.
<220> FEATURE:
<221> NAME/KEY: misc_feature
<222> LOCATION: (80)..(80)
<223> OTHER INFORMATION: Position 80 to 80 may be absent, if present n is C or T.
<220> FEATURE:
<221> NAME/KEY: misc_feature
<222> LOCATION: (81)..(81)
<223> OTHER INFORMATION: Position 81 to 81 may be absent, if present n is T, G, C or A.
<220> FEATURE:
<221> NAME/KEY: misc_feature
<222> LOCATION: (82)..(82)
<223> OTHER INFORMATION: Position 82 to 82 may be absent, if present n is A, T or G.
<220> FEATURE:
<221> NAME/KEY: misc_feature
<222> LOCATION: (83)..(83)
<223> OTHER INFORMATION: Position 83 to 83 may be absent, if present n is C, A or G.
<220> FEATURE:
<221> NAME/KEY: misc_feature
<222> LOCATION: (84)..(84)
<223> OTHER INFORMATION: n is C or T.

<220> FEATURE:
<221> NAME/KEY: misc_feature
<222> LOCATION: (85)..(85)
<223> OTHER INFORMATION: Position 85 to 85 may be absent, if present n is T or C.
<220> FEATURE:
<221> NAME/KEY: misc_feature
<222> LOCATION: (86)..(86)
<223> OTHER INFORMATION: Position 86 to 86 may be absent, if present n is G, A or T.
<220> FEATURE:
<221> NAME/KEY: misc_feature
<222> LOCATION: (87)..(87)
<223> OTHER INFORMATION: Position 87 to 87 may be absent, if present n is G.
<220> FEATURE:
<221> NAME/KEY: misc_feature
<222> LOCATION: (88)..(88)
<223> OTHER INFORMATION: Position 88 to 88 may be absent, if present n is G.
<220> FEATURE:
<221> NAME/KEY: misc_feature
<222> LOCATION: (89)..(89)
<223> OTHER INFORMATION: Position 89 to 89 may be absent, if present n is C.
<220> FEATURE:
<221> NAME/KEY: misc_feature
<222> LOCATION: (90)..(90)
<223> OTHER INFORMATION: Position 90 to 90 may be absent, if present n is A, G or T.
<220> FEATURE:
<221> NAME/KEY: misc_feature
<222> LOCATION: (91)..(91)
<223> OTHER INFORMATION: Position 91 to 91 may be absent, if present n is G or A.
<220> FEATURE:
<221> NAME/KEY: misc_feature
<222> LOCATION: (92)..(92)
<223> OTHER INFORMATION: Position 92 to 92 may be absent, if present n is A or G.
<220> FEATURE:
<221> NAME/KEY: misc_feature
<222> LOCATION: (93)..(93)
<223> OTHER INFORMATION: Position 93 to 93 may be absent, if present n is G.
<220> FEATURE:
<221> NAME/KEY: misc_feature
<222> LOCATION: (94)..(94)
<223> OTHER INFORMATION: Position 94 to 94 may be absent, if present n is G, T, A, or C.
<220> FEATURE:
<221> NAME/KEY: misc_feature
<222> LOCATION: (95)..(95)
<223> OTHER INFORMATION: n is G, T or C.
<220> FEATURE:
<221> NAME/KEY: misc_feature
<222> LOCATION: (96)..(96)
<223> OTHER INFORMATION: n is G, T or A.
<220> FEATURE:
<221> NAME/KEY: misc_feature
<222> LOCATION: (97)..(97)
<223> OTHER INFORMATION: n is G, A or T.
<220> FEATURE:
<221> NAME/KEY: misc_feature
<222> LOCATION: (98)..(98)
<223> OTHER INFORMATION: n is C, A or T.
<220> FEATURE:
<221> NAME/KEY: misc_feature
<222> LOCATION: (99)..(99)
<223> OTHER INFORMATION: n is C, T or G.
<220> FEATURE:
<221> NAME/KEY: misc_feature
<222> LOCATION: (100)..(100)
<223> OTHER INFORMATION: n is C, A, or G.
<220> FEATURE:
<221> NAME/KEY: misc_feature
<222> LOCATION: (101)..(101)
<223> OTHER INFORMATION: n is C, T, A or G.
<220> FEATURE:

<221> NAME/KEY: misc_feature
<222> LOCATION: (102)..(102)
<223> OTHER INFORMATION: n is T, C, G or A.
<220> FEATURE:
<221> NAME/KEY: misc_feature
<222> LOCATION: (103)..(103)
<223> OTHER INFORMATION: n is A, T, G or C.
<220> FEATURE:
<221> NAME/KEY: misc_feature
<222> LOCATION: (104)..(104)
<223> OTHER INFORMATION: Position 104 to 104 may be absent, if present n is C.
<220> FEATURE:
<221> NAME/KEY: misc_feature
<222> LOCATION: (105)..(105)
<223> OTHER INFORMATION: Position 105 to 105 may be absent, if present n is C.
<220> FEATURE:
<221> NAME/KEY: misc_feature
<222> LOCATION: (106)..(106)
<223> OTHER INFORMATION: Position 106 to 106 may be absent, if present n is G, T, A or C.
<220> FEATURE:
<221> NAME/KEY: misc_feature
<222> LOCATION: (107)..(107)
<223> OTHER INFORMATION: Position 107 to 107 may be absent, if present n is G, T, or A.
<220> FEATURE:
<221> NAME/KEY: misc_feature
<222> LOCATION: (108)..(108)
<223> OTHER INFORMATION: Position 108 to 108 may be absent, if present n is T, C or G.
<220> FEATURE:
<221> NAME/KEY: misc_feature
<222> LOCATION: (109)..(109)
<223> OTHER INFORMATION: Position 109 to 109 may be absent, if present n is T or G.
<220> FEATURE:
<221> NAME/KEY: misc_feature
<222> LOCATION: (110)..(110)
<223> OTHER INFORMATION: Position 110 to 110 may be absent, if present n is T, A or G.
<220> FEATURE:
<221> NAME/KEY: misc_feature
<222> LOCATION: (111)..(111)
<223> OTHER INFORMATION: Position 111 to 111 may be absent, if present n is T, A or C.
<220> FEATURE:
<221> NAME/KEY: misc_feature
<222> LOCATION: (112)..(112)
<223> OTHER INFORMATION: Position 112 to 112 may be absent, if present n is A, G, T or C.
<220> FEATURE:
<221> NAME/KEY: misc_feature
<222> LOCATION: (113)..(113)
<223> OTHER INFORMATION: Position 113 to 113 may be absent, if present n is A, T or G.
<220> FEATURE:
<221> NAME/KEY: misc_feature
<222> LOCATION: (114)..(114)
<223> OTHER INFORMATION: Position 114 to 114 may be absent, if present n is C, T or G.
<220> FEATURE:
<221> NAME/KEY: misc_feature
<222> LOCATION: (115)..(115)
<223> OTHER INFORMATION: Position 115 to 115 may be absent, if present n is T, or C.
<220> FEATURE:
<221> NAME/KEY: misc_feature
<222> LOCATION: (116)..(116)
<223> OTHER INFORMATION: Position 116 to 116 may be absent, if present n is C, A, T or G.
<220> FEATURE:
<221> NAME/KEY: misc_feature
<222> LOCATION: (117)..(117)
<223> OTHER INFORMATION: Position 117 to 117 may be absent, if present n is T, A or C.
<220> FEATURE:
<221> NAME/KEY: misc_feature

```
<222> LOCATION: (118)..(118)
<223> OTHER INFORMATION: Position 118 to 118 may be absent, if present n
      is C, T or A.
<220> FEATURE:
<221> NAME/KEY: misc_feature
<222> LOCATION: (119)..(119)
<223> OTHER INFORMATION: Position 119 to 119 may be absent, if present n
      is T, A, G or C.
<220> FEATURE:
<221> NAME/KEY: misc_feature
<222> LOCATION: (120)..(120)
<223> OTHER INFORMATION: Position 120 to 120 may be absent, if present n
      is A or C.
<220> FEATURE:
<221> NAME/KEY: misc_feature
<222> LOCATION: (121)..(121)
<223> OTHER INFORMATION: Position 121 to 121 may be absent, if present n
      is C, T, G or A.
<220> FEATURE:
<221> NAME/KEY: misc_feature
<222> LOCATION: (122)..(122)
<223> OTHER INFORMATION: Position 122 to 122 may be absent, if present n
      is G, A, C or T.
<220> FEATURE:
<221> NAME/KEY: misc_feature
<222> LOCATION: (123)..(123)
<223> OTHER INFORMATION: Position 123 to 123 may be absent, if present n
      is G, C or T.
<220> FEATURE:
<221> NAME/KEY: misc_feature
<222> LOCATION: (124)..(124)
<223> OTHER INFORMATION: Position 124 to 124 may be absent, if present n
      is C, A or T.
<220> FEATURE:
<221> NAME/KEY: misc_feature
<222> LOCATION: (125)..(125)
<223> OTHER INFORMATION: Position 125 to 125 may be absent, if present n
      is T, A, C or G.
<220> FEATURE:
<221> NAME/KEY: misc_feature
<222> LOCATION: (126)..(126)
<223> OTHER INFORMATION: Position 126 to 126 may be absent, if present n
      is A, G, C or T.
<220> FEATURE:
<221> NAME/KEY: misc_feature
<222> LOCATION: (127)..(127)
<223> OTHER INFORMATION: Position 127 to 127 may be absent, if present n
      is A, G, C or T.
<220> FEATURE:
<221> NAME/KEY: misc_feature
<222> LOCATION: (128)..(128)
<223> OTHER INFORMATION: Position 128 to 128 may be absent, if present n
      is C or G.
<220> FEATURE:
<221> NAME/KEY: misc_feature
<222> LOCATION: (129)..(129)
<223> OTHER INFORMATION: Position 129 to 129 may be absent, if present n
      is C or T.
<220> FEATURE:
<221> NAME/KEY: misc_feature
<222> LOCATION: (130)..(130)
<223> OTHER INFORMATION: Position 130 to 130 may be absent, if present n
      is T, G or C.
<220> FEATURE:
<221> NAME/KEY: misc_feature
<222> LOCATION: (131)..(131)
<223> OTHER INFORMATION: Position 131 to 131 may be absent, if present n
      is G, C or T.
<220> FEATURE:
<221> NAME/KEY: misc_feature
<222> LOCATION: (132)..(132)
<223> OTHER INFORMATION: Position 132 to 132 may be absent, if present n
      is G.
<220> FEATURE:
<221> NAME/KEY: misc_feature
<222> LOCATION: (133)..(133)
<223> OTHER INFORMATION: Position 133 to 133 may be absent, if present n
      is T.
<220> FEATURE:
```

<221> NAME/KEY: misc_feature
<222> LOCATION: (134)..(134)
<223> OTHER INFORMATION: Position 134 to 134 may be absent, if present n is C.
<220> FEATURE:
<221> NAME/KEY: misc_feature
<222> LOCATION: (135)..(135)
<223> OTHER INFORMATION: Position 135 to 135 may be absent, if present n is A.
<220> FEATURE:
<221> NAME/KEY: misc_feature
<222> LOCATION: (136)..(136)
<223> OTHER INFORMATION: Position 136 to 136 may be absent, if present n is T.
<220> FEATURE:
<221> NAME/KEY: misc_feature
<222> LOCATION: (137)..(137)
<223> OTHER INFORMATION: Position 137 to 137 may be absent, if present n is C.
<220> FEATURE:
<221> NAME/KEY: misc_feature
<222> LOCATION: (138)..(138)
<223> OTHER INFORMATION: Position 138 to 138 may be absent, if present n is A.
<220> FEATURE:
<221> NAME/KEY: misc_feature
<222> LOCATION: (139)..(139)
<223> OTHER INFORMATION: Position 139 to 139 may be absent, if present n is A.
<220> FEATURE:
<221> NAME/KEY: misc_feature
<222> LOCATION: (140)..(140)
<223> OTHER INFORMATION: Position 140 to 140 may be absent, if present n is T.
<220> FEATURE:
<221> NAME/KEY: misc_feature
<222> LOCATION: (141)..(141)
<223> OTHER INFORMATION: Position 141 to 141 may be absent, if present n is C.
<220> FEATURE:
<221> NAME/KEY: misc_feature
<222> LOCATION: (142)..(142)
<223> OTHER INFORMATION: Position 142 to 142 may be absent, if present n is T.
<220> FEATURE:
<221> NAME/KEY: misc_feature
<222> LOCATION: (143)..(143)
<223> OTHER INFORMATION: Position 143 to 143 may be absent, if present n is C.
<220> FEATURE:
<221> NAME/KEY: misc_feature
<222> LOCATION: (144)..(144)
<223> OTHER INFORMATION: Position 144 to 144 may be absent, if present n is A.
<220> FEATURE:
<221> NAME/KEY: misc_feature
<222> LOCATION: (145)..(145)
<223> OTHER INFORMATION: Position 145 to 145 may be absent, if present n is C.
<220> FEATURE:
<221> NAME/KEY: misc_feature
<222> LOCATION: (146)..(146)
<223> OTHER INFORMATION: Position 146 to 146 may be absent, if present n is G.
<220> FEATURE:
<221> NAME/KEY: misc_feature
<222> LOCATION: (147)..(147)
<223> OTHER INFORMATION: Position 147 to 147 may be absent, if present n is T.
<220> FEATURE:
<221> NAME/KEY: misc_feature
<222> LOCATION: (148)..(148)
<223> OTHER INFORMATION: Position 148 to 148 may be absent, if present n is C.
<220> FEATURE:
<221> NAME/KEY: misc_feature
<222> LOCATION: (149)..(149)
<223> OTHER INFORMATION: Position 149 to 149 may be absent, if present n is C.

```
<220> FEATURE:
<221> NAME/KEY: misc_feature
<222> LOCATION: (150)..(150)
<223> OTHER INFORMATION: Position 150 to 150 may be absent, if present n
      is A, G, C or T.
<220> FEATURE:
<221> NAME/KEY: misc_feature
<222> LOCATION: (151)..(151)
<223> OTHER INFORMATION: Position 151 to 151 may be absent, if present n
      is A, T, C or G.
<220> FEATURE:
<221> NAME/KEY: misc_feature
<222> LOCATION: (152)..(152)
<223> OTHER INFORMATION: Position 152 to 152 may be absent, if present n
      is T, A, C or G.
<220> FEATURE:
<221> NAME/KEY: misc_feature
<222> LOCATION: (153)..(153)
<223> OTHER INFORMATION: Position 153 to 153 may be absent, if present n
      is G, C, or A.
<220> FEATURE:
<221> NAME/KEY: misc_feature
<222> LOCATION: (154)..(154)
<223> OTHER INFORMATION: Position 154 to 154 may be absent, if present n
      is G, C, A or T.
<220> FEATURE:
<221> NAME/KEY: misc_feature
<222> LOCATION: (155)..(155)
<223> OTHER INFORMATION: Position 155 to 155 may be absent, if present n
      is A, C or T.
<220> FEATURE:
<221> NAME/KEY: misc_feature
<222> LOCATION: (156)..(156)
<223> OTHER INFORMATION: Position 156 to 156 may be absent, if present n
      is C, G or T.
<220> FEATURE:
<221> NAME/KEY: misc_feature
<222> LOCATION: (157)..(157)
<223> OTHER INFORMATION: Position 157 to 157 may be absent, if present n
      is T or C.
<220> FEATURE:
<221> NAME/KEY: misc_feature
<222> LOCATION: (158)..(158)
<223> OTHER INFORMATION: Position 158 to 158 may be absent, if present n
      is A, T, G or C.
<220> FEATURE:
<221> NAME/KEY: misc_feature
<222> LOCATION: (159)..(159)
<223> OTHER INFORMATION: Position 159 to 159 may be absent, if present n
      is C or T.
<220> FEATURE:
<221> NAME/KEY: misc_feature
<222> LOCATION: (160)..(160)
<223> OTHER INFORMATION: Position 160 to 160 may be absent, if present n
      is G, T, A or C.
<220> FEATURE:
<221> NAME/KEY: misc_feature
<222> LOCATION: (161)..(161)
<223> OTHER INFORMATION: Position 161 to 161 may be absent, if present n
      is A or G.
<220> FEATURE:
<221> NAME/KEY: misc_feature
<222> LOCATION: (162)..(162)
<223> OTHER INFORMATION: Position 162 to 162 may be absent, if present n
      is C or T.
<220> FEATURE:
<221> NAME/KEY: misc_feature
<222> LOCATION: (163)..(163)
<223> OTHER INFORMATION: Position 163 to 163 may be absent, if present n
      is A, T or G.
<220> FEATURE:
<221> NAME/KEY: misc_feature
<222> LOCATION: (164)..(164)
<223> OTHER INFORMATION: Position 164 to 164 may be absent, if present n
      is T, A, C or G.
<220> FEATURE:
<221> NAME/KEY: misc_feature
<222> LOCATION: (165)..(165)
<223> OTHER INFORMATION: Position 165 to 165 may be absent, if present n
```

```
      is A or T.
<220> FEATURE:
<221> NAME/KEY: misc_feature
<222> LOCATION: (166)..(166)
<223> OTHER INFORMATION: Position 166 to 166 may be absent, if present n
      is G, T or A.
<220> FEATURE:
<221> NAME/KEY: misc_feature
<222> LOCATION: (167)..(167)
<223> OTHER INFORMATION: Position 167 to 167 may be absent, if present n
      is A.
<220> FEATURE:
<221> NAME/KEY: misc_feature
<222> LOCATION: (168)..(168)
<223> OTHER INFORMATION: Position 168 to 168 may be absent, if present n
      is C.
<220> FEATURE:
<221> NAME/KEY: misc_feature
<222> LOCATION: (169)..(169)
<223> OTHER INFORMATION: Position 169 to 169 may be absent, if present n
      is G or A.
<220> FEATURE:
<221> NAME/KEY: misc_feature
<222> LOCATION: (170)..(170)
<223> OTHER INFORMATION: Position 170 to 170 may be absent, if present n
      is C.
<220> FEATURE:
<221> NAME/KEY: misc_feature
<222> LOCATION: (171)..(171)
<223> OTHER INFORMATION: Position 171 to 171 may be absent, if present n
      is T.
<220> FEATURE:
<221> NAME/KEY: misc_feature
<222> LOCATION: (172)..(172)
<223> OTHER INFORMATION: Position 172 to 172 may be absent, if present n
      is C.
<220> FEATURE:
<221> NAME/KEY: misc_feature
<222> LOCATION: (173)..(173)
<223> OTHER INFORMATION: Position 173 to 173 may be absent, if present n
      is G or A.
<220> FEATURE:
<221> NAME/KEY: misc_feature
<222> LOCATION: (174)..(174)
<223> OTHER INFORMATION: Position 174 to 174 may be absent, if present n
      is T, G or A.
<220> FEATURE:
<221> NAME/KEY: misc_feature
<222> LOCATION: (175)..(175)
<223> OTHER INFORMATION: Position 175 to 175 may be absent, if present n
      is C or T.
<220> FEATURE:
<221> NAME/KEY: misc_feature
<222> LOCATION: (176)..(176)
<223> OTHER INFORMATION: Position 176 to 176 may be absent, if present n
      is T or C.
<220> FEATURE:
<221> NAME/KEY: misc_feature
<222> LOCATION: (177)..(177)
<223> OTHER INFORMATION: Position 177 to 177 may be absent, if present n
      is A, G or T.
<220> FEATURE:
<221> NAME/KEY: misc_feature
<222> LOCATION: (178)..(178)
<223> OTHER INFORMATION: Position 178 to 178 may be absent, if present n
      is G, A or T.
<220> FEATURE:
<221> NAME/KEY: misc_feature
<222> LOCATION: (179)..(179)
<223> OTHER INFORMATION: Position 179 to 179 may be absent, if present n
      is T, C or A.
<220> FEATURE:
<221> NAME/KEY: misc_feature
<222> LOCATION: (180)..(180)
<223> OTHER INFORMATION: Position 180 to 180 may be absent, if present n
      is C or T.
<220> FEATURE:
<221> NAME/KEY: misc_feature
<222> LOCATION: (181)..(181)
```

```
<223> OTHER INFORMATION: Position 181 to 181 may be absent, if present n
      is C, A or T.
<220> FEATURE:
<221> NAME/KEY: misc_feature
<222> LOCATION: (182)..(182)
<223> OTHER INFORMATION: Position 182 to 182 may be absent, if present n
      is G, A or C.
<220> FEATURE:
<221> NAME/KEY: misc_feature
<222> LOCATION: (183)..(183)
<223> OTHER INFORMATION: Position 183 to 183 may be absent, if present n
      is C, A or T.
<220> FEATURE:
<221> NAME/KEY: misc_feature
<222> LOCATION: (184)..(184)
<223> OTHER INFORMATION: Position 184 to 184 may be absent, if present n
      is C or T.
<220> FEATURE:
<221> NAME/KEY: misc_feature
<222> LOCATION: (185)..(185)
<223> OTHER INFORMATION: Position 185 to 185 may be absent, if present n
      is A, C, G or T.
<220> FEATURE:
<221> NAME/KEY: misc_feature
<222> LOCATION: (186)..(186)
<223> OTHER INFORMATION: Position 186 to 186 may be absent, if present n
      is A, T or C.
<220> FEATURE:
<221> NAME/KEY: misc_feature
<222> LOCATION: (187)..(187)
<223> OTHER INFORMATION: Position 187 to 187 may be absent, if present n
      is G, T, A, or C.
<220> FEATURE:
<221> NAME/KEY: misc_feature
<222> LOCATION: (188)..(188)
<223> OTHER INFORMATION: Position 188 to 188 may be absent, if present n
      is G, C or A.
<220> FEATURE:
<221> NAME/KEY: misc_feature
<222> LOCATION: (189)..(189)
<223> OTHER INFORMATION: Position 189 to 189 may be absent, if present n
      is C or T.
<220> FEATURE:
<221> NAME/KEY: misc_feature
<222> LOCATION: (190)..(190)
<223> OTHER INFORMATION: Position 190 to 190 may be absent, if present n
      is C, T or A.
<220> FEATURE:
<221> NAME/KEY: misc_feature
<222> LOCATION: (191)..(191)
<223> OTHER INFORMATION: Position 191 to 191 may be absent, if present n
      is A or G.
<220> FEATURE:
<221> NAME/KEY: misc_feature
<222> LOCATION: (192)..(192)
<223> OTHER INFORMATION: Position 192 to 192 may be absent, if present n
      is C or T.
<220> FEATURE:
<221> NAME/KEY: misc_feature
<222> LOCATION: (193)..(193)
<223> OTHER INFORMATION: Position 193 to 193 may be absent, if present n
      is C, A or T.
<220> FEATURE:
<221> NAME/KEY: misc_feature
<222> LOCATION: (194)..(194)
<223> OTHER INFORMATION: Position 194 to 194 may be absent, if present n
      is A, T, A or G.
<220> FEATURE:
<221> NAME/KEY: misc_feature
<222> LOCATION: (195)..(195)
<223> OTHER INFORMATION: Position 195 to 195 may be absent, if present n
      is T, G, or A.
<220> FEATURE:
<221> NAME/KEY: misc_feature
<222> LOCATION: (196)..(196)
<223> OTHER INFORMATION: Position 196 to 196 may be absent, if present n
      is A or T.
<220> FEATURE:
<221> NAME/KEY: misc_feature
```

<222> LOCATION: (197)..(197)
<223> OTHER INFORMATION: Position 197 to 197 may be absent, if present n is T, or A.
<220> FEATURE:
<221> NAME/KEY: misc_feature
<222> LOCATION: (198)..(198)
<223> OTHER INFORMATION: Position 198 to 198 may be absent, if present n is A or G.
<220> FEATURE:
<221> NAME/KEY: misc_feature
<222> LOCATION: (199)..(199)
<223> OTHER INFORMATION: Position 199 to 199 may be absent, if present n is G, A, or T.
<220> FEATURE:
<221> NAME/KEY: misc_feature
<222> LOCATION: (200)..(200)
<223> OTHER INFORMATION: Position 200 to 200 may be absent, if present n is G or T.
<220> FEATURE:
<221> NAME/KEY: misc_feature
<222> LOCATION: (201)..(201)
<223> OTHER INFORMATION: Position 201 to 201 may be absent, if present n is T, C, or A.
<220> FEATURE:
<221> NAME/KEY: misc_feature
<222> LOCATION: (202)..(202)
<223> OTHER INFORMATION: Position 202 to 202 may be absent, if present n is A or G.
<220> FEATURE:
<221> NAME/KEY: misc_feature
<222> LOCATION: (203)..(203)
<223> OTHER INFORMATION: Position 203 to 203 may be absent, if present n is T or C.
<220> FEATURE:
<221> NAME/KEY: misc_feature
<222> LOCATION: (204)..(204)
<223> OTHER INFORMATION: Position 204 to 204 may be absent, if present n is G, T, A or C.
<220> FEATURE:
<221> NAME/KEY: misc_feature
<222> LOCATION: (205)..(205)
<223> OTHER INFORMATION: Position 205 to 205 may be absent, if present n is G, T or A.
<220> FEATURE:
<221> NAME/KEY: misc_feature
<222> LOCATION: (206)..(206)
<223> OTHER INFORMATION: Position 206 to 206 may be absent, if present n is G, C or A.
<220> FEATURE:
<221> NAME/KEY: misc_feature
<222> LOCATION: (207)..(207)
<223> OTHER INFORMATION: Position 207 to 207 may be absent, if present n is C or T.
<220> FEATURE:
<221> NAME/KEY: misc_feature
<222> LOCATION: (208)..(208)
<223> OTHER INFORMATION: Position 208 to 208 may be absent, if present n is A or T.
<220> FEATURE:
<221> NAME/KEY: misc_feature
<222> LOCATION: (209)..(209)
<223> OTHER INFORMATION: Position 209 to 209 may be absent, if present n is A, C or G.
<220> FEATURE:
<221> NAME/KEY: misc_feature
<222> LOCATION: (210)..(210)
<223> OTHER INFORMATION: Position 210 to 210 may be absent, if present n is C or A.
<220> FEATURE:
<221> NAME/KEY: misc_feature
<222> LOCATION: (211)..(211)
<223> OTHER INFORMATION: Position 211 to 211 may be absent, if present n is A or G.
<220> FEATURE:
<221> NAME/KEY: misc_feature
<222> LOCATION: (212)..(212)
<223> OTHER INFORMATION: Position 212 to 212 may be absent, if present n is C.
<220> FEATURE:

<221> NAME/KEY: misc_feature
<222> LOCATION: (213)..(213)
<223> OTHER INFORMATION: Position 213 to 213 may be absent, if present n is C.
<220> FEATURE:
<221> NAME/KEY: misc_feature
<222> LOCATION: (214)..(214)
<223> OTHER INFORMATION: Position 214 to 214 may be absent, if present n is C or T.
<220> FEATURE:
<221> NAME/KEY: misc_feature
<222> LOCATION: (215)..(215)
<223> OTHER INFORMATION: Position 215 to 215 may be absent, if present n is A or G.
<220> FEATURE:
<221> NAME/KEY: misc_feature
<222> LOCATION: (216)..(216)
<223> OTHER INFORMATION: Position 216 to 216 may be absent, if present n is C or A.
<220> FEATURE:
<221> NAME/KEY: misc_feature
<222> LOCATION: (217)..(217)
<223> OTHER INFORMATION: Position 217 to 217 may be absent, if present n is C or A.
<220> FEATURE:
<221> NAME/KEY: misc_feature
<222> LOCATION: (218)..(218)
<223> OTHER INFORMATION: Position 218 to 218 may be absent, if present n is G.
<220> FEATURE:
<221> NAME/KEY: misc_feature
<222> LOCATION: (219)..(219)
<223> OTHER INFORMATION: Position 219 to 219 may be absent, if present n is A.
<220> FEATURE:
<221> NAME/KEY: misc_feature
<222> LOCATION: (220)..(220)
<223> OTHER INFORMATION: Position 220 to 220 may be absent, if present n is G.
<220> FEATURE:
<221> NAME/KEY: misc_feature
<222> LOCATION: (221)..(221)
<223> OTHER INFORMATION: Position 221 to 221 may be absent, if present n is C.
<220> FEATURE:
<221> NAME/KEY: misc_feature
<222> LOCATION: (222)..(222)
<223> OTHER INFORMATION: Position 222 to 222 may be absent, if present n is G.
<220> FEATURE:
<221> NAME/KEY: misc_feature
<222> LOCATION: (223)..(223)
<223> OTHER INFORMATION: Position 223 to 223 may be absent, if present n is C.
<220> FEATURE:
<221> NAME/KEY: misc_feature
<222> LOCATION: (224)..(224)
<223> OTHER INFORMATION: Position 224 to 224 may be absent, if present n is T.
<220> FEATURE:
<221> NAME/KEY: misc_feature
<222> LOCATION: (225)..(225)
<223> OTHER INFORMATION: Position 225 to 225 may be absent, if present n is T.
<220> FEATURE:
<221> NAME/KEY: misc_feature
<222> LOCATION: (226)..(226)
<223> OTHER INFORMATION: Position 226 to 226 may be absent, if present n is C.
<220> FEATURE:
<221> NAME/KEY: misc_feature
<222> LOCATION: (227)..(227)
<223> OTHER INFORMATION: Position 227 to 227 may be absent, if present n is G.
<220> FEATURE:
<221> NAME/KEY: misc_feature
<222> LOCATION: (228)..(228)
<223> OTHER INFORMATION: Position 228 to 228 may be absent, if present n is T.

```
<220> FEATURE:
<221> NAME/KEY: misc_feature
<222> LOCATION: (229)..(229)
<223> OTHER INFORMATION: Position 229 to 229 may be absent, if present n
      is C.
<220> FEATURE:
<221> NAME/KEY: misc_feature
<222> LOCATION: (230)..(230)
<223> OTHER INFORMATION: Position 230 to 230 may be absent, if present n
      is G.
<220> FEATURE:
<221> NAME/KEY: misc_feature
<222> LOCATION: (231)..(231)
<223> OTHER INFORMATION: Position 231 to 231 may be absent, if present n
      is A.
<220> FEATURE:
<221> NAME/KEY: misc_feature
<222> LOCATION: (232)..(232)
<223> OTHER INFORMATION: Position 232 to 232 may be absent, if present n
      is G.
<220> FEATURE:
<221> NAME/KEY: misc_feature
<222> LOCATION: (233)..(233)
<223> OTHER INFORMATION: Position 233 to 233 may be absent, if present n
      is G.
<220> FEATURE:
<221> NAME/KEY: misc_feature
<222> LOCATION: (234)..(234)
<223> OTHER INFORMATION: Position 234 to 234 may be absent, if present n
      is C.
<220> FEATURE:
<221> NAME/KEY: misc_feature
<222> LOCATION: (235)..(235)
<223> OTHER INFORMATION: Position 235 to 235 may be absent, if present n
      is C.
<220> FEATURE:
<221> NAME/KEY: misc_feature
<222> LOCATION: (236)..(236)
<223> OTHER INFORMATION: Position 236 to 236 may be absent, if present n
      is A.
<220> FEATURE:
<221> NAME/KEY: misc_feature
<222> LOCATION: (237)..(237)
<223> OTHER INFORMATION: Position 237 to 237 may be absent, if present n
      is C.
<220> FEATURE:
<221> NAME/KEY: misc_feature
<222> LOCATION: (238)..(238)
<223> OTHER INFORMATION: Position 238 to 238 may be absent, if present n
      is C.

<400> SEQUENCE: 81

gactnnnnnn nnnnnnnnnn nnnnnnnnnn nnnnnnnnnn nnnnnnnnnn nnnnnnnnnn      60

nnnnnnnnnn nnnnnnnnnn nnnnnnnnnn nnnnnnnnnn nnnnnnnnnn nnnnnnnnnn     120

nnnnnnnnnn nnnnnnnnnn nnnnnnnnnn nnnnnnnnnn nnnnnnnnnn nnnnnnnnnn     180

nnnnnnnnnn nnnnnnnnnn nnnnnnnnnn nnnnnnnnnn nnnnnnnnnn nnnnnnnn       238
```

MUTANT SUBGENOMIC PROMOTER LIBRARY AND USES THEREOF

RELATED APPLICATION

This application claims priority under 35 U.S.C. § 119(e) to U.S. Provisional Application Ser. No. 62/831,561, filed Apr. 9, 2019, the entire contents of which are incorporated by reference herein.

FEDERALLY SPONSORED RESEARCH

This invention was made with Government support under Grant Nos. R01 CA206218 and R01 EB025854 awarded by the National Institutes of Health (NIH). The Government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jul. 5, 2022, is named M065670466US01-SEQ-GIC and is 51,363 bytes in size.

BACKGROUND

The study of gene function often requires changing the expression of a gene and evaluating the consequences. In principle, the expression of any given gene can be modulated in a quasi-continuum of discrete expression levels but the traditional approaches are usually limited to two extremes: gene knockout and strong overexpression. However, many applications necessitate a slight change in gene expression level different from that of a counterpart wild-type gene expression level in a specific window; this requirement can be met by using promoter libraries. Therefore, it is of interest to develop promoters with differential levels of activity to control expression levels of multiple transgenes in one construct.

SUMMARY

The present disclosure is based, at least in part, on the unexpected discovery that certain mutants of a subgenomic promoter derived from alphavirus have differential activity in driving the expression of operably linked transgenes (e.g., genes encoding therapeutic molecules or antibody). These mutant subgenomic promoters may be used to fine tune expression level of multiple transgenes from a single alphavirus replicon (e.g., increase functional antibody production).

In some aspects, the present disclosure provides an engineered subgenomic promoter library, comprising a plurality of promoters, wherein each promoter comprises a nucleotide sequence of $\mathrm{GACT}X_1X_2X_3X_4X_5X_6X_7X_8X_9X_{10}X_{11}X_{12}X_{13}X_{14}X_{15}X_{16}X_{17}X_{18}X_{19}X_{20}$ $X_{21}X_{22}X_{23}X_{24}X_{25}X_{26}X_{27}X_{28}X_{29}X_{30}X_{31}X_{32}X_{33}X_{34}X_{35}X_{36}X_{37}X_{38}X_{39}$ $X_{40}X_{41}X_{42}X_{43}X_{44}X_{45}X_{46}X_{47}X_{48}X_{49}X_{50}X_{51}X_{52}X_{53}X_{54}X_{55}X_{56}X_{57}X_{58}$ $X_{59}X_{60}X_{61}X_{62}X_{63}X_{64}X_{65}X_{66}X_{67}X_{68}X_{69}X_{70}X_{71}X_{72}X_{73}X_{74}X_{75}X_{76}X_{77}$ $X_{78}X_{79}X_{80}X_{81}X_{82}X_{83}X_{84}X_{85}X_{86}X_{87}X_{88}X_{89}X_{90}X_{91}X_{92}X_{93}X_{94}X_{95}X_{96}$ -continued $X_{97}X_{98}X_{99}X_{100}X_{101}X_{012}X_{103}X_{104}X_{105}X_{106}X_{107}X_{108}X_{109}X_{110}X_{111}$ $X_{112}X_{113}X_{114}X_{115}X_{116}X_{117}X_{118}X_{119}X_{120}X_{121}X_{122}X_{123}X_{124}X_{125}$ $X_{126}X_{127}X_{128}X_{129}X_{130}X_{131}X_{132}X_{133}X_{134}X_{135}X_{136}X_{137}X_{138}X_{139}$ $X_{140}X_{141}X_{142}X_{143}X_{144}X_{145}X_{146}X_{147}X_{148}X_{149}X_{150}X_{151}X_{152}X_{153}$ $X_{154}X_{155}X_{156}X_{157}X_{158}X_{159}X_{160}X_{161}X_{162}X_{163}X_{164}X_{165}X_{166}X_{167}$ $X_{168}X_{169}X_{170}X_{171}X_{172}X_{173}X_{174}X_{175}X_{176}X_{177}X_{178}X_{179}X_{180}X_{181}$ $X_{182}X_{183}X_{184}X_{185}X_{186}X_{187}X_{188}X_{189}X_{199}X_{200}X_{201}X_{201}X_{203}X_{204}$ $X_{205}X_{206}X_{207}X_{208}X_{209}X_{210}X_{211}X_{212}X_{213}X_{214}X_{215}X_{216}X_{217}X_{218}$ $X_{219}X_{220}X_{221}X_{222}X_{223}X_{224}X_{225}X_{226}X_{227}X_{228}X_{229}X_{230}X_{231}X_{232}$ $X_{233}X_{234}$, wherein $X_1$ is absent or present, and when $X_1$ is present, $X_1$=C; wherein $X_2$ is absent or present, and when $X_2$ is present, $X_2$=A; wherein $X_3$=T or C; wherein $X_4$=C or G; wherein $X_5$=C or A; wherein $X_6$=C, T or A; wherein $X_7$=T, G or C; wherein $X_8$=C, T or A; wherein $X_9$ is absent or present, and when $X_9$ is present, $X_9$=C or A; wherein $X_{10}$ is absent or present, and when $X_{10}$ is present, $X_{10}$=G; wherein $X_{11}$ is absent or present, and when $X_{11}$ is present, $X_{11}$=T, A or G; wherein $X_{12}$ is absent or present, and when $X_{12}$ is present, $X_{12}$=T or C; wherein $X_{13}$ is absent or present, and when $X_{13}$ is present, $X_{13}$=A or C; wherein $X_{14}$=G, T or A; wherein $X_{15}$=T, A or C; wherein $X_{16}$=T, C or A; wherein $X_{17}$=A, T or C; wherein $X_{18}$=T, C or A; wherein $X_{19}$=G, C or A; wherein $X_{20}$=G, C or A; wherein $X_{21}$ is absent or present, and when $X_{21}$ is present, $X_{21}$=C or T; wherein $X_{22}$ is absent or present, and when $X_{22}$ is present, $X_{22}$=A; wherein $X_{23}$ is absent or present, and when $X_{23}$ is present, $X_{23}$=A or T; wherein $X_{24}$=C or T; wherein $X_{25}$=A, T or G; wherein $X_{26}$=T, A, C, or G; wherein $X_{27}$=G, T or A; wherein $X_{28}$=A, G, or T; wherein $X_{29}$=C, T, or G; wherein $X_{30}$=T, C or A; wherein $X_{31}$=A, C or G; wherein $X_{32}$=C, T, or G; wherein $X_{33}$=T, C or A; wherein $X_{34}$=C, A, G or T; wherein $X_{35}$=T, C, G or A; wherein $X_{36}$=A, T or G; wherein $X_{37}$ is absent or present, and when $X_{37}$ is present, $X_{37}$=T or A; wherein $X_{38}$ is absent or present, and when $X_{38}$ is present, $X_{38}$=C or T; wherein $X_{39}$ is absent or present, and when $X_{39}$ is present, $X_{39}$=A, G or T; wherein $X_{40}$ is absent or present, and when $X_{40}$ is present, $X_{40}$=G, A or T; wherein $X_{41}$ is absent or present, and when $X_{41}$ is present, $X_{41}$=C or T; wherein $X_{42}$=G, C or A; wherein $X_{43}$=C, A or T; wherein $X_{44}$=T, A or C; wherein $X_{45}$=A, T or C; wherein $X_{46}$=G, T, A or C; wherein $X_{47}$=C or T; wherein $X_{48}$ is absent or present, and when $X_{48}$ is present, $X_{48}$=C or A; wherein $X_{49}$ is absent or present, and when $X_{49}$ is present, $X_{49}$=A or T; wherein $X_{50}$ is absent or present, and when $X_{50}$ is present, $X_{50}$=C or T; wherein $X_{51}$ is absent or present, and when $X_{51}$ is present, $X_{51}$=A or T; wherein $X_{52}$ is absent or present, and when $X_{52}$ is present, $X_{52}$=T or A; wherein $X_{53}$ is absent or present, and when $X_{53}$ is present, $X_{53}$=C; wherein $X_{54}$ is absent or present, and when $X_{54}$ is present, $X_{54}$=T or C; wherein $X_{55}$ is absent or present, and when $X_{55}$ is present, $X_{55}$=T or C; wherein $X_{56}$ is absent or present, and when $X_{56}$ is present, $X_{56}$=C; wherein $X_{57}$ is absent or present, and when $X_{57}$ is present, $X_{57}$=C, T, G or A; wherein $X_{58}$ is absent or present, and when $X_{58}$ is present, $X_{58}$=T; wherein $X_{59}$ is absent or present, and when $X_{59}$ is present, $X_{59}$=A, G or C; wherein $X_{60}$ is absent or present, and when $X_{60}$ is present, $X_{60}$=G, A, T, C; wherein $X_{61}$ is absent or present, and when $X_{61}$ is present, $X_{61}$=T, A, or G; wherein $X_{62}$ is absent or present, and when $X_{62}$ is present, $X_{62}$=G or A; wherein $X_{63}$ is absent or present, and when $X_{63}$ is present, $X_{63}$=T, A, or G; wherein $X_{64}$ is absent or present, and when $X_{64}$ is present, $X_{64}$=T, G, C, or A; wherein $X_{65}$ is absent or present, and when $X_{65}$ is present, $X_{65}$=A or G; wherein $X_{66}$ is absent or present, and when $X_{66}$ is present, $X_{66}$=A or G; wherein $X_{67}$ is absent or present, and when $X_{67}$ is present, $X_{67}$=A, T, or C; wherein $X_{68}$ is absent or present, and when $X_{68}$ is present, $X_{68}$=T, A, C or G; wherein $X_{69}$ is absent or present, and when $X_{69}$ is present, $X_{69}$=C, T, G or A; wherein $X_{70}$ is absent or present, and when $X_{70}$ is present, $X_{70}$=A, T or G; wherein $X_{71}$ is absent or present, and when $X_{71}$ is present, $X_{71}$=T or A; wherein $X_{72}$ is absent or present, and when $X_{72}$ is present, $X_{72}$=T or C; wherein $X_{73}$ is absent or present, and when $X_{73}$ is present, $X_{73}$=C, A or T; wherein $X_{74}$ is absent or present, and when $X_{74}$ is present, $X_{74}$=A, T or C; wherein $X_{75}$ is absent or present, and when $X_{75}$ is present, $X_{75}$=G, A, C or T; wherein $X_{76}$ is absent or present, and when $X_{76}$ is present, $X_{76}$=C or T; wherein $X_{77}$ is absent or present, and when $X_{77}$ is present, $X_{77}$=T, G, C or A; wherein $X_{78}$ is absent or present, and when $X_{78}$ is present, $X_{78}$=A, T or G; wherein $X_{79}$ is absent or present, and when $X_{79}$ is present, $X_{79}$=C, A or G; wherein $X_{80}$=C or T; wherein $X_{81}$ is absent or present, and when $X_{81}$ is present, $X_{81}$=T or C; wherein $X_{82}$ is absent or present, and when $X_{82}$ is present, $X_{82}$=G, A or T; wherein $X_{83}$ is absent or present, and when $X_{83}$ is present, $X_{83}$=G; wherein $X_{84}$ is absent or present, and when $X_{84}$ is present, $X_{84}$=G; wherein $X_{85}$ is absent or present, and when $X_{85}$ is present, $X_{85}$=C; wherein $X_{86}$ is absent or present, and when $X_{86}$ is present, $X_{86}$=A, G or T; wherein $X_{87}$ is absent or present, and when $X_{87}$ is present, $X_{87}$=G or A; wherein $X_{88}$ is absent or present, and when $X_{88}$ is present, $X_{88}$=A or G; wherein $X_{89}$ is absent or present, and when $X_{89}$ is present, $X_{89}$=G; wherein $X_{90}$ is absent or present, and when $X_{90}$ is present, $X_{90}$=G, T, A, or C; wherein $X_{91}$=G, T or C; wherein $X_{92}$=G, T or A; wherein $X_{93}$=G, A or T; wherein $X_{94}$=C, A or T; wherein $X_{95}$=C, T or G; wherein $X_{96}$=C, A, or G; wherein $X_{97}$=C, T, A or G; wherein $X_{98}$=T, C, G or A; wherein $X_{99}$=A, T, G or C; wherein $X_{100}$ is absent or present, and when $X_{100}$ is present, $X_{100}$=C; wherein $X_{101}$ is absent or present, and when $X_{101}$ is present, $X_{101}$=C; wherein $X_{102}$ is absent or present, and when $X_{102}$ is present, $X_{102}$=G, T, A or C; wherein $X_{103}$ is absent or present, and when $X_{103}$ is present, $X_{103}$=G, T, or A; wherein $X_{104}$ is absent or present, and when $X_{104}$ is present, $X_{104}$=T, C or G; wherein $X_{105}$ is absent or present, and when $X_{105}$ is present, $X_{105}$=T or G; wherein $X_{106}$ is absent or present, and when $X_{106}$ is present, $X_{106}$=T, A or G; wherein $X_{107}$ is absent or present, and when $X_{107}$ is present, $X_{107}$=T, A or C; wherein $X_{108}$ is absent or present, and when $X_{108}$ is present, $X_{108}$=A, G, T or C; wherein $X_{109}$ is absent or present, and when $X_{109}$ is present, $X_{109}$=A, T or G; wherein $X_{110}$ is absent or present, and when $X_{110}$ is present, $X_{110}$=C, T or G; wherein $X_{111}$ is absent or present, and when $X_{111}$ is present, $X_{111}$=T, or C; wherein $X_{112}$ is absent or present, and when $X_{112}$ is present, $X_{112}$=C, A, T or G; wherein $X_{113}$ is absent or present, and when $X_{113}$ is present, $X_{113}$=T, A or C; wherein $X_{114}$ is absent or present, and when $X_{114}$ is present, $X_{114}$=C, T or A; wherein $X_{115}$ is absent or present, and when $X_{115}$ is present, $X_{115}$=T, A, G or C; wherein $X_{116}$ is absent or present, and when $X_{116}$ is present, $X_{116}$=A or C; wherein $X_{117}$ is absent or present, and when $X_{117}$ is present, $X_{117}$=C, T, G or A; wherein $X_{118}$ is absent or present, and when $X_{118}$ is present, $X_{118}$=G, A, C or T; wherein $X_{119}$ is absent or present, and when $X_{119}$ is present, $X_{119}$=G, C or T; wherein $X_{120}$ is absent or present, and when $X_{120}$ is present, $X_{120}$=C, A or T; wherein $X_{121}$ is absent or present, and when $X_{121}$ is present, $X_{121}$=T, A, C or G; wherein $X_{122}$ is absent or present, and when $X_{122}$ is present, $X_{122}$=A, G, C or T; wherein $X_{123}$ is absent or present, and when $X_{123}$ is present, $X_{123}$=A, G, C or T; wherein $X_{124}$ is absent or present, and when $X_{124}$ is present, $X_{124}$=C or G; wherein $X_{125}$ is absent or present, and when $X_{125}$ is present, $X_{125}$=C or T; wherein $X_{126}$ is absent or present, and when $X_{126}$ is present, $X_{126}$=T, G or C; wherein $X_{127}$ is absent or present, and when $X_{127}$ is present, $X_{127}$=G, C or T; wherein $X_{128}$ is absent or present, and when $X_{128}$ is present, $X_{128}$=G; wherein $X_{129}$ is absent or present, and when $X_{129}$ is present, $X_{129}$=T; wherein $X_{130}$ is absent or present, and when $X_{130}$ is present, $X_{130}$=C; wherein $X_{131}$ is absent or present, and when $X_{131}$ is present, $X_{131}$=A; wherein $X_{132}$ is absent or present, and when $X_{132}$ is present, $X_{132}$=T; wherein $X_{133}$ is absent or present, and when $X_{133}$ is present, $X_{133}$=C; wherein $X_{134}$ is absent or present, and when $X_{134}$ is present, $X_{134}$=A; wherein $X_{135}$ is absent or present, and when $X_{135}$ is present, $X_{135}$=A; wherein $X_{136}$ is absent or present, and when $X_{136}$ is present, $X_{136}$=T; wherein $X_{137}$ is absent or present, and when $X_{137}$ is present, $X_{137}$=C; wherein $X_{138}$ is absent or present, and when $X_{138}$ is present, $X_{138}$=T; wherein $X_{139}$ is absent or present, and when $X_{139}$ is present, $X_{139}$=C; wherein $X_{140}$ is absent or present, and when $X_{140}$ is present, $X_{140}$=A; wherein $X_{141}$ is absent or present, and when $X_{141}$ is present, $X_{141}$=C; wherein $X_{142}$ is absent or present, and when $X_{142}$ is present, $X_{142}$=G; wherein $X_{143}$ is absent or present, and when $X_{143}$ is present, $X_{143}$=T; wherein $X_{144}$ is absent or present, and when $X_{144}$ is present, $X_{144}$=C; wherein $X_{145}$ is absent or present, and when $X_{145}$ is present, $X_{145}$=C; wherein $X_{146}$ is absent or present, and when $X_{146}$ is present, $X_{146}$=A, G, C or T; wherein $X_{147}$ is absent or present, and when $X_{147}$ is present, $X_{147}$=A, T, C or G; wherein $X_{148}$ is absent or present, and when $X_{148}$ is present, $X_{148}$=T, A, C or G; wherein $X_{149}$ is absent or present, and when $X_{149}$ is present, $X_{149}$=G, C, or A; wherein $X_{150}$ is absent or present, and when $X_{150}$ is present, $X_{150}$=G, C, A or T; wherein $X_{151}$ is absent or present, and when $X_{151}$ is present, $X_{151}$=A, C or T; wherein $X_{152}$ is absent or present, and when $X_{152}$ is present, $X_{152}$=C, G or T; wherein $X_{153}$ is absent or present, and when $X_{153}$ is present, $X_{153}$=T or C; wherein $X_{154}$ is absent or present, and when $X_{154}$ is present, $X_{154}$=A, T, G or C; wherein $X_{155}$ is absent or present, and when $X_{155}$ is present, $X_{155}$=C or T; wherein $X_{156}$ is absent or present, and when $X_{156}$ is present, $X_{156}$=G, T, A or C; wherein $X_{157}$ is absent or present, and when $X_{157}$ is present, $X_{157}$=A or G; wherein $X_{158}$ is absent or present, and when $X_{158}$ is present, $X_{158}$=C or T; wherein $X_{159}$ is absent or present, and when $X_{159}$ is present, $X_{159}$=A, T or G; wherein $X_{160}$ is absent or present, and when $X_{160}$ is present, $X_{160}$=T, A, C or G; wherein $X_{161}$ is absent or present, and when $X_{161}$ is present, $X_{161}$=A or T; wherein $X_{162}$ is absent or present, and when $X_{162}$ is present, $X_{162}$=G, T or A; wherein $X_{163}$ is absent or present, and when $X_{163}$ is present, $X_{163}$=A; wherein $X_{164}$ is absent or present, and when $X_{164}$ is present, $X_{164}$=C; wherein $X_{165}$ is absent or present, and when $X_{165}$ is present, $X_{165}$=G or A; wherein $X_{166}$ is absent or present, and when $X_{166}$ is present, $X_{166}$=C; wherein $X_{167}$ is absent or present, and when $X_{167}$ is present, $X_{167}$=T; wherein $X_{168}$ is absent or present, and when $X_{168}$ is present, $X_{168}$=C; wherein $X_{169}$ is absent or present, and when $X_{169}$ is present, $X_{169}$=G or A; wherein $X_{170}$ is absent or present, and when $X_{170}$ is present, $X_{170}$=T, G or A; wherein $X_{171}$ is absent or present, and when $X_{171}$ is present, $X_{171}$=C or T; wherein $X_{172}$ is absent or present, and when $X_{172}$ is present, $X_{172}$=T or C; wherein $X_{173}$ is absent or present, and when $X_{173}$ is present, $X_{173}$=A, G or T; wherein $X_{174}$ is absent or present, and when $X_{174}$ is present, $X_{174}$=G, A or T; wherein $X_{175}$ is absent or present, and when $X_{175}$ is present, $X_{175}$=T, C or A; wherein $X_{176}$ is absent or present, and when $X_{176}$ is present, $X_{176}$=C or T; wherein $X_{177}$ is absent or present, and when $X_{177}$ is present, $X_{177}$=C, A or T; wherein $X_{178}$ is absent or present, and when $X_{178}$ is present, $X_{178}$=G, A or C; wherein $X_{179}$ is absent or present, and when $X_{179}$ is present, $X_{179}$=C, A or T; wherein $X_{180}$ is absent or present, and when $X_{180}$ is present, $X_{180}$=C or T; wherein $X_{181}$ is absent or present, and when $X_{181}$ is present, $X_{181}$=A, C, G or T; wherein $X_{182}$ is absent or present, and when $X_{182}$ is present, $X_{182}$=A, T or C; wherein $X_{183}$ is absent or present, and when $X_{183}$ is present, $X_{183}$=G, T, A, or C; wherein $X_{184}$ is absent or present, and when $X_{184}$ is present, $X_{184}$=G, C or A; wherein $X_{185}$ is absent or present, and when $X_{185}$ is present, $X_{185}$=C or T; wherein $X_{186}$ is absent or present, and when $X_{186}$ is present, $X_{186}$=C, T or A; wherein $X_{187}$ is absent or present, and when $X_{187}$ is present, $X_{187}$=A or G; wherein $X_{188}$ is absent or present, and when $X_{188}$ is present, $X_{188}$=C or T; wherein $X_{189}$ is absent or present, and when $X_{189}$ is present, $X_{189}$=C, A or T; wherein $X_{190}$ is absent or present, and when $X_{190}$ is present, $X_{190}$=A, T, A or G; wherein $X_{191}$ is absent or present, and when $X_{191}$ is present, $X_{191}$=T, G, or A; wherein $X_{192}$ is absent or present, and when $X_{192}$ is present, $X_{192}$=A or T; wherein $X_{193}$ is absent or present, and when $X_{193}$ is present, $X_{193}$=T, or A; wherein $X_{194}$ is absent or present, and when $X_{194}$ is present, $X_{194}$=A or G; wherein $X_{195}$ is absent or present, and when $X_{195}$ is present, $X_{195}$=G, A, or T; wherein $X_{196}$ is absent or present, and when $X_{196}$ is present, $X_{196}$=G or T; wherein $X_{197}$ is absent or present, and when $X_{197}$ is present, $X_{197}$=T, C, or A; wherein $X_{198}$ is absent or present, and when $X_{198}$ is present, $X_{198}$=A or G; wherein $X_{199}$ is absent or present, and when $X_{199}$ is present, $X_{199}$=T or C; wherein $X_{200}$ is absent or present, and when $X_{200}$ is present, $X_{200}$=G, T, A or C; wherein $X_{201}$ is absent or present, and when $X_{201}$ is present, $X_{201}$=G, T or A; wherein $X_{202}$ is absent or present, and when $X_{202}$ is present, $X_{202}$=G, C or A; wherein $X_{203}$ is absent or present, and when $X_{203}$ is present, $X_{203}$=C or T; wherein $X_{204}$ is absent or present, and when $X_{204}$ is present, $X_{204}$=A or T; wherein $X_{205}$ is absent or present, and when $X_{205}$ is present, $X_{205}$=A, C or G; wherein $X_{206}$ is absent or present, and when $X_{206}$ is present, $X_{206}$=C or A; wherein $X_{207}$ is absent or present, and when $X_{207}$ is present, $X_{207}$=A or G; wherein $X_{208}$ is absent or present, and when $X_{208}$ is present, $X_{208}$=C; wherein $X_{209}$ is absent or present, and when $X_{209}$ is present, $X_{209}$=C; wherein $X_{210}$ is absent or present, and when $X_{210}$ is present, $X_{210}$=C or T; wherein $X_{211}$ is absent or present, and when $X_{211}$ is present, $X_{211}$=A or G; wherein $X_{212}$ is absent or present, and when $X_{212}$ is present, $X_{212}$=C or A; wherein $X_{213}$ is absent or present, and when $X_{213}$ is present, $X_{213}$=C or A; wherein $X_{214}$ is absent or present, and when $X_{214}$ is present, $X_{214}$=G; wherein $X_{215}$ is absent or present, and when $X_{215}$ is present, $X_{215}$=A; wherein $X_{216}$ is absent or present, and when $X_{216}$ is present, $X_{216}$=G; wherein $X_{217}$ is absent or present, and when $X_{217}$ is present, $X_{217}$=C; wherein $X_{218}$ is absent or present, and when $X_{218}$ is present, $X_{218}$=G; wherein $X_{219}$ is absent or present, and when $X_{219}$ is present, $X_{219}$=C; wherein $X_{220}$ is absent or present, and when $X_{220}$ is present, $X_{220}$=T; wherein $X_{221}$ is absent or present, and when $X_{221}$ is present, $X_{221}$=T; wherein $X_{222}$ is absent or present, and when $X_{222}$ is present, $X_{222}$=C; wherein $X_{223}$ is absent or present, and when $X_{223}$ is present, $X_{223}$=G; wherein $X_{224}$ is absent or present, and when $X_{224}$ is present, $X_{224}$=T; wherein $X_{225}$ is absent or present, and when $X_{225}$ is present, $X_{225}$=C; wherein $X_{226}$ is absent or present, and when $X_{226}$ is present, $X_{226}$=G; wherein $X_{227}$ is absent or present, and when $X_{227}$ is present, $X_{227}$=A; wherein $X_{228}$ is absent or present, and when $X_{228}$ is present, $X_{228}$=G; wherein $X_{229}$ is absent or present, and when $X_{229}$ is present, $X_{229}$=G; wherein $X_{230}$ is absent or present, and when $X_{230}$ is present, $X_{230}$=C; wherein $X_{231}$ is absent or present, and when $X_{231}$ is present, $X_{231}$=C; wherein $X_{232}$ is absent or present, and when $X_{232}$ is present, $X_{232}$=A; wherein $X_{233}$ is absent or present, and when $X_{233}$ is present, $X_{233}$=C; wherein $X_{234}$ is absent or present, and when $X_{234}$ is present, $X_{234}$=C (SEQ ID NO: 81).

In some aspects, the present disclosure provides an engineered subgenomic promoter library comprising a plurality of promoters. Each promoter can comprise a nucleic acid sequence at least 70% identical to nucleic acid sequences of SEQ IDs NO: 1-74 and 81. In some embodiments, the engineered subgenomic promoter library is a subgenomic promoter derived from an alphavirus. In some embodiments, the alphavirus is Venezuela Equine Encephalitis virus, Semliki Forest virus, or Sindbis virus.

The subgenomic promoters described herein may further comprise restriction endonuclease sites at the 5' and 3' ends. In some embodiments, the restriction endonuclease sites at the 5' and 3' ends are SapI sites.

In some embodiments, the engineered subgenomic promoter library comprises engineered subgenomic promoters having differential activities.

Other aspects of the present disclosure provide engineered nucleic acids. In some embodiments, the engineered nucleic acids include a promoter selected from the engineered subgenomic promoter library and the promoter is operably linked to a transgene. In some embodiments, the transgene encodes a therapeutic molecule or a detectable molecule. In other embodiments, the transgene encodes a heavy chain or a light chain of an antibody.

Further provided herein are expression cassettes that include one or more engineered nucleic acid described herein. In some embodiments, the expression cassette is an antibody expression cassette. In some embodiments, the antibody expression cassettes include a first and a second engineered nucleic acids as described herein. In some embodiments, the first engineered nucleic acid includes a transgene encoding a heavy chain of an antibody. In some embodiments, the second engineered nucleic acid includes a transgene encoding a light chain of an antibody. In some embodiments, the antibody expression cassette comprises a first engineered nucleic acid comprising a first engineered subgenomic promoter selected from the engineered subgenomic promoter library operably linked to a first transgene, and the first transgene encodes a heavy chain of an antibody; and a second engineered nucleic acid comprising a second engineered subgenomic promoter selected from the engineered subgenomic promoter library operably linked to a second transgene, and the second transgene encodes a light chain of an antibody.

In another aspect, the disclosure provides vectors comprising the engineered nucleic acid described herein. In some embodiments, the vectors include one or more engineered nucleic acid, or one or more expression cassette described herein. In some embodiments, the vector is a plasmid, a RNA replicon, linear double stranded DNA, viral vectors, liposome or nanoparticles. In some examples, the RNA replicon is derived from an alphavirus. In one example, the one or more engineered nucleic acid is located at the subgenomic region of the RNA replicon.

In another aspect, the present disclosure also provides cells comprising the engineered nucleic acid or the expression cassette described herein are provided.

Other aspects of the invention provide methods for selecting an antibody expression cassette for optimized production of functional antibody. The methods include constructing an antibody expression cassette library comprising a plurality of antibody expression cassettes for expression of a heavy chain and a light chain of an antibody, wherein the antibody expression cassette comprises: a first engineered nucleic acid comprising a first engineered subgenomic promoter selected from the engineered subgenomic promoter library operably linked to a first transgene, and the first transgene encodes a heavy chain of an antibody; and a second engineered nucleic acid comprising a second engineered subgenomic promoter selected from the engineered subgenomic promoter library operably linked to a second transgene, and the second transgene encodes a light chain of an antibody. The methods further include delivering the plurality of engineered nucleic acids to a population of cells; culturing the cell under conditions allowing for expression of the heavy chain and the light chain of the antibody; measuring a level of functional antibody comprising the heavy chain and the light chain produced by population of cells; selecting cell(s) expressing optimal level of functional antibody; and determining the nucleic acid sequence of the subgenomic promoter in the first engineered nucleic acid and the nucleic acid sequence of the subgenomic promoter in the second engineered nucleic acid.

In another aspect, methods for producing an antibody are provided. The methods include constructing an antibody expression cassette described herein for expression of a heavy chain and a light chain of an antibody; delivering the antibody expression cassette to a population of cells or a host animal; culturing the cell or growing the host animal under conditions allowing for expression of the heavy chain and the light chain of the antibody; and harvesting the cultured host cell or culture medium or tissue from the host animal for collection of the antibody. In some embodiments, the method further includes purifying the antibody.

Also provided herein are methods for producing one or more molecules. The methods include constructing an expression cassette described herein for expression of the one or more molecules; delivering the expression cassette to a population of cells or a host animal; culturing the cell or growing the host animal under conditions allowing for expression of the one or more molecules; and harvesting the cultured host cell or culture medium or tissue from the host animal for collection of the molecule. In some embodiments, the method further includes purifying the one or more molecules. In some embodiments, the one or more molecules encoded by the expression cassette (e.g., by a transgene operably linked to a subgenomic promoter) is a detectable molecule or a therapeutic molecule.

The details of embodiments of the invention are set forth in the description below. Other features or advantages of the present invention will be apparent from the following drawings and detailed description of several embodiments, and also from the appended claims.

BRIEF DESCRIPTION OF DRAWINGS

FIG. 1A is a chart illustrating the gating strategy for sorting cells expressing various levels of m Venus and mKate. FIG. 1B is a chart showing the varying expression strength of different subgenomic promoters selected from the subgenomic promoter library.

DETAILED DESCRIPTION

Figure 1A:
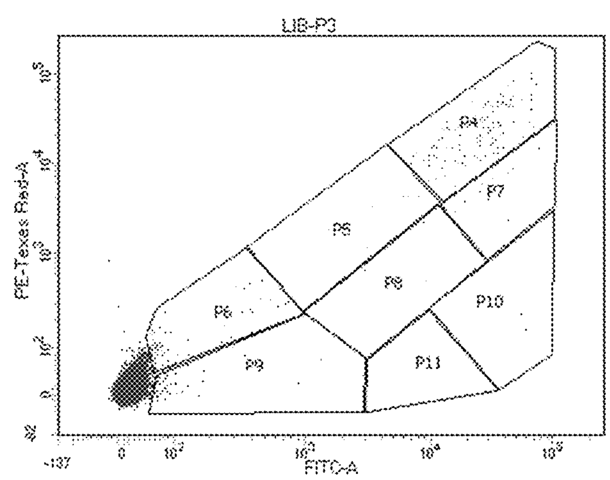
FIGS. 1A-1B are graphs showing that the subgenomic mutant promoters in the library have differential levels of activity.

The present disclosure is based, at least in part, on the unexpected discovery that certain mutants of a subgenomic promoter derived from alphavirus have differential activity in driving the expression of downstream transgenes (e.g., therapeutic molecules or antibody). These mutant subgenomic promoters may be used to fine tune expression level of multiple transgenes from a single alphavirus replicon (e.g., increase functional antibody production).

I. Engineered Subgenomic Promoter Library

A "promoter" refers to a control region of a nucleic acid sequence at which initiation and rate of transcription of the remainder of a nucleic acid sequence are controlled. A promoter regulates (e.g., activates or represses) expression or transcription of the nucleic acid sequence that it is operably linked to. A promoter may also contain sub-regions at which regulatory proteins and molecules may bind, such as RNA polymerase and transcription factors. Promoters may be constitutive, inducible, activatable, repressible, tissue-specific, cell type-specific, cell state-specific, or any combination thereof. In some embodiments, the promoter described herein is a subgenomic promoter.

Promoters of the present disclosure are engineered promoters. An engineered promoter is a promoter that is not "naturally occurring." The engineered promoters of the present disclosure may be produced using recombinant cloning and/or nucleic acid amplification technology, including polymerase chain reaction (PCR) (see U.S. Pat. Nos. 4,683,202 and 5,928,906). The term "subgenomic promoter" is used interchangeably with "engineered subgenomic promoter" herein.

Promoters of the present disclosure are subgenomic promoters derived from an alphavirus. Many positive-sense RNA viruses, e.g., alphaviruses, produce these subgenomic mRNAs (sgRNA) as one of the common infection techniques used by these viruses and generally transcribe late viral genes. As used herein, the term "subgenome" or "subgenomic" refers to a smaller section of the whole replicon genome. Accordingly, subgenomic transcription, as used herein, refers to the transcription of one or more genes in the replicon genome but not all the genes constituting the replicon genome, which genes can be heterologous to the virus genome, such as transgenes in engineered virus genomes including the replicons described herein. Thus in some embodiments, subgenomic transcription refers to transcription of the genes of experimental or therapeutic interest, which are described elsewhere herein (e.g., antibodies). In such cases, the subgenomic promoter is a promoter used to regulate transcription of a specific heterologous gene to which the promoter is operably linked, resulting in the formation of mRNA for that gene alone.

In some embodiments, the length of an engineered subgenomic promoter is 200 nucleotides or shorter. In some embodiments, a subgenomic promoter may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 nucleotides long.

A virus is a small pathogen that is only capable of replication inside a living host cell (e.g., prokaryotic and eukaryotic cells). Outside of living cells, viruses exist as independent particles (e.g., viral particles or virions), which comprise genetic material in the form of DNA or RNA, which can be single-stranded or double-stranded. Viruses with DNA genomes are referred to as DNA viruses, and viruses with RNA genomes are referred to as RNA viruses. In some cases, the virus comprises nucleic acid-associated proteins and the combination of the virus and nucleic acid-associated proteins is referred to as nucleoprotein. In addition to the genetic material, viruses have a single or double protein coat, also known as a capsid, which facilitates attachment of the virus to a living host cell's receptors during infection and protects the genetic material of the virus from enzymatic degradation. The combination of nucleoprotein and the capsid is referred to as a nucleocapsid. In some cases, viruses have a lipid bilayer envelope, studded with virus-coded, glycosylated (trans) membrane-associated proteins. Once a virus has infected a living host cell, the virus is dependent on the living host cell to supply the machinery for its replication, and propagation thereafter. The viral genome codes for some structural proteins and non-structural regulatory proteins.

In some embodiments, the subgenomic promoter provided herein is derived from an alphavirus. Distinct from host mRNA, alphavirus replicon RNAs encode a set of four nonstructural proteins (nsPs 1-4) that are responsible both for genome replication. When engineered to include gene(s) encoding non-viral products, such as therapeutic molecules, in place of one or more of the nonstructural protein genes, alphavirus replicon RNAs provide for transcription of such non-viral products under the subgenomic promoter(s) to which the gene(s) are operably linked.

Alphaviruses are part of the Group IV Togaviridae family of viruses, possess a positive sense, single-stranded RNA genome, and are characterized by an icosahedral nucleocapsid. Other non-limiting examples of Group IV viruses include Astroviridae, Caliciviridae, Coronaviridae, Flaviviridae, Picornaviridae, Arteriviridae, and Togaviridae. The alphavirus genus includes 26 enveloped viruses that infect eukaryotes. Alphaviruses have a broad host range and are transmitted by mosquitos and hematophagous arthropods. Non-limiting examples of alphaviruses include Venezuelan equine encephalitis virus (VEE), Semliki Forest virus (SF), Sindbis virus (SIN), Eastern Equine Encephalitis virus (EEE), Western equine encephalitis virus (WEE), Everglades virus (EVE), Mucambo virus (MUC), Pixuna virus (PIX), Semliki Forest virus (SF), Middelburg virus (MID), Chikungunya virus (CHIK), O'Nyong-Nyong virus (ONN), Ross River virus (RR), Barmah Forest virus (BF), Getah virus (GET), Sagiyama virus (SAG), Bebaru virus (BEB), Mayaro virus (MAY), Una virus (UNA), Aura virus (AURA), Babanki virus (BAB), Highlands J virus (HJ), and Fort Morgan virus (FM).

In some instances, the alphavirus replicon is a VEE alphavirus replicon. The virion of VEE is spherical and possesses a lipid membrane with glycoprotein surface proteins spread around the outer surface. Typically. VEE has a genome of approximately 11.45 kb, excluding the 5'-terminal cap and 3'-terminal poly(A) tract, and comprises 4 nonstructural proteins (nsPs) and 5 structural proteins. The non-structural proteins include nsP1, nsP2, nsP3, and nsP4, while the structural region encodes proteins C. E3, E2, 6K, and E1. In some instances, the subgenomic promoter is a WT subgenomic promoter derived from VEE. In other instances, the subgenomic promoter is a mutant subgenomic promoter. Mutant sequences of the subgenomic promoters can be obtained by conventional methods in the art, e.g., error prone PCR. Non limiting examples of mutations of the mutant subgenomic promoters are point mutations, deletions, or insertions.

Exemplary sequence of the wild type VEE virus subgenomic promoter region (−99/+30) and a Kozak sequence (in bold face) is set forth in SEQ ID NO: 1:

(SEQ ID NO: 1)
GACTTCCATCATAGTTATGGCCATGACTACTCTAGCTAGCAGTGTTAAAT

CATTCAGCTACCTGAGAGGGGCCCCTATAACTCTCTACGGCTAACCTGAA

TGGACTACGACATAGTCTAGTCCGCCAAGGCCACC.

A Kozak sequence is a sequence which occurs in eukaryotic mRNA and plays a major role in the initiation of the translation process. In some embodiments, the Kozak sequence has a consensus sequence (gcc)gccRccAUGG (SEQ ID NO: 79). In this consensus sequence, AUG indicate the translation start codon, coding for Methionine; uppercase letters indicate highly conserved bases, i.e. the 'AUGG' sequence is constant or rarely, if ever, changes; 'R' indicates that a purine (adenine or guanine) is always observed at this position (with adenine being more frequent according to Kozak); a lower-case letter denotes the most common base at a position where the base can nevertheless vary; the sequence in parentheses (gcc) is of uncertain significance. Variations of the Kozak sequence are known in the art, and can be selected according to the application of interest (see, e.g., Hernadez, Conservation and Variability of the AUG Initiation Codon Context in Eukaryotes, *Trends in Biochemical Sciences*, Volume 44, Issue 12, December 2019, Pages 1009-1021). In some embodiments, An exemplary Kozak sequence is GCCACC (SEQ ID NO: 75). In some embodiments, the subgenomic promoter optionally comprises a Kozak sequence at the 3' end.

In some embodiments, the mutant subgenomic promoters in the subgenomic promoter library comprises one or more mutation compared to the wild-type subgenomic promoters. In some embodiments, the subgenomic promoters in the library comprises a consensus nucleotide sequence as set forth in SEQ ID NO: 81:

$GACTX_1X_2X_3X_4X_5X_6X_7X_8X_9X_{10}X_{11}X_{12}X_{13}X_{14}X_{15}X_{16}X_{17}X_{18}X_{19}X_{20}$
$X_{21}X_{22}X_{23}X_{24}X_{25}X_{26}X_{27}X_{28}X_{29}X_{30}X_{31}X_{32}X_{33}X_{34}X_{35}X_{36}X_{37}X_{38}X_{39}$
$X_{40}X_{41}X_{42}X_{43}X_{44}X_{45}X_{46}X_{47}X_{48}X_{49}X_{50}X_{51}X_{52}X_{53}X_{54}X_{55}X_{56}X_{57}X_{58}$
$X_{59}X_{60}X_{61}X_{62}X_{63}X_{64}X_{65}X_{66}X_{67}X_{68}X_{69}X_{70}X_{71}X_{72}X_{73}X_{74}X_{75}X_{76}X_{77}$
$X_{78}X_{79}X_{80}X_{81}X_{82}X_{83}X_{84}X_{85}X_{86}X_{87}X_{88}X_{89}X_{90}X_{91}X_{92}X_{93}X_{94}X_{95}X_{96}$
$X_{97}X_{98}X_{99}X_{100}X_{101}X_{012}X_{103}X_{104}X_{105}X_{106}X_{107}X_{108}X_{109}X_{110}X_{111}$
$X_{112}X_{113}X_{114}X_{115}X_{116}X_{117}X_{118}X_{119}X_{120}X_{121}X_{122}X_{123}X_{124}X_{125}$
$X_{126}X_{127}X_{128}X_{129}X_{130}X_{131}X_{132}X_{133}X_{134}X_{135}X_{136}X_{137}X_{138}X_{139}$
$X_{140}X_{141}X_{142}X_{143}X_{144}X_{145}X_{146}X_{147}X_{148}X_{149}X_{150}X_{151}X_{152}X_{153}$
$X_{154}X_{155}X_{156}X_{157}X_{158}X_{159}X_{160}X_{161}X_{162}X_{163}X_{164}X_{165}X_{166}X_{167}$
$X_{168}X_{169}X_{170}X_{171}X_{172}X_{173}X_{174}X_{175}X_{176}X_{177}X_{178}X_{179}X_{180}X_{181}$
$X_{182}X_{183}X_{184}X_{185}X_{186}X_{187}X_{188}X_{189}X_{199}X_{200}X_{201}X_{201}X_{203}X_{204}$
$X_{205}X_{206}X_{207}X_{208}X_{209}X_{210}X_{211}X_{212}X_{213}X_{214}X_{215}X_{216}X_{217}X_{218}$
$X_{219}X_{220}X_{221}X_{222}X_{223}X_{224}X_{225}X_{226}X_{227}X_{228}X_{229}X_{230}X_{231}X_{232}$
$X_{233}X_{234}$, in which $X_1$ is absent or present, and when $X_1$ is present, $X_1$=C; wherein $X_2$ is absent or present, and when $X_2$ is present, $X_2$=A; wherein $X_3$=T or C; wherein $X_4$=C or G; wherein $X_5$=C or A; wherein $X_6$=C, T or A; wherein $X_7$=T, G or C; wherein $X_8$=C, T or A; wherein $X_9$ is absent or present, and when $X_9$ is present, $X_9$=C or A; wherein $X_{10}$ is absent or present, and when $X_{10}$ is present, $X_{10}$=G; wherein $X_{11}$ is absent or present, and when $X_{11}$ is present, $X_{11}$=T, A or G; wherein $X_{12}$ is absent or present, and when $X_{12}$ is present, $X_{12}$=T or C; wherein $X_{13}$ is absent or present, and when $X_{13}$ is present, $X_{13}$=A or C; wherein $X_{14}$=G, T or A; wherein $X_{15}$=T, A or C; wherein $X_{16}$=T, C or A; wherein $X_{17}$=A, T or C; wherein $X_{18}$=T, C or A; wherein $X_{19}$=G, C or A; wherein $X_{20}$=G, C or A; wherein $X_{21}$ is absent or present, and when $X_{21}$ is present, $X_{21}$=C or T; wherein $X_{22}$ is absent or present, and when $X_{22}$ is present, $X_{22}$=A; wherein $X_{23}$ is absent or present, and when $X_{23}$ is present, $X_{23}$=A or T; wherein $X_{24}$=C or T; wherein $X_{25}$=A, T or G; wherein $X_{26}$=T, A, C, or G; wherein $X_{27}$=G, T or A; wherein $X_{28}$=A, G, or T; wherein $X_{29}$=C, T, or G; wherein $X_{30}$=T, C or A; wherein $X_{31}$=A, C or G; wherein $X_{32}$=C, T, or G; wherein $X_{33}$=T, C or A; wherein $X_{34}$=C, A, G or T; wherein $X_{35}$=T, C, G or A; wherein $X_{36}$=A, T or G; wherein $X_{37}$ is absent or present, and when $X_{37}$ is present, $X_{37}$=T or A; wherein $X_{38}$ is absent or present, and when $X_{38}$ is present, $X_{38}$=C or T; wherein $X_{39}$ is absent or present, and when $X_{39}$ is present, $X_{39}$=A, G or T; wherein $X_{40}$ is absent or present, and when $X_{40}$ is present, $X_{40}$=G, A or T; wherein $X_{41}$ is absent or present, and when $X_{41}$ is present, $X_{41}$=C or T; wherein $X_{42}$=G, C or A; wherein $X_{43}$=C, A or T; wherein $X_{44}$=T, A or C; wherein $X_{45}$=A, T or C; wherein $X_{46}$=G, T, A or C; wherein $X_{47}$=C or T; wherein $X_{48}$ is absent or present, and when $X_{48}$ is present, $X_{48}$=C or A; wherein $X_{49}$ is absent or present, and when $X_{49}$ is present, $X_{49}$=A or T; wherein $X_{50}$ is absent or present, and when $X_{50}$ is present, $X_{50}$=C or T; wherein $X_{51}$ is absent or present, and when $X_{51}$ is present, $X_{51}$=A or T; wherein $X_{52}$ is absent or present, and when $X_{52}$ is present, $X_{52}$=T or A; wherein $X_{53}$ is absent or present, and when $X_{53}$ is present, $X_{53}$=C; wherein $X_{54}$ is absent or present, and when $X_{54}$ is present, $X_{54}$=T or C; wherein $X_{55}$ is absent or present, and when $X_{55}$ is present, $X_{55}$=T or C; wherein $X_{56}$ is absent or present, and when $X_{56}$ is present, $X_{56}$=C; wherein $X_{57}$ is absent or present, and when $X_{57}$ is present, $X_{57}$=C, T, G or A; wherein $X_{58}$ is absent or present, and when $X_{58}$ is present, $X_{58}$=T; wherein $X_{59}$ is absent or present, and when $X_{59}$ is present, $X_{59}$=A, G or C; wherein $X_{60}$ is absent or present, and when $X_{60}$ is present, $X_{60}$=G, A, T, C; wherein $X_{61}$ is absent or present, and when $X_{61}$ is present, $X_{61}$=T, A, or G; wherein $X_{62}$ is absent or present, and when $X_{62}$ is present, $X_{62}$=G or A; wherein $X_{63}$ is absent or present, and when $X_{63}$ is present, $X_{63}$=T, A, or G; wherein $X_{64}$ is absent or present, and when $X_{64}$ is present, $X_{64}$=T, G, C, or A; wherein $X_{65}$ is absent or present, and when $X_{65}$ is present, $X_{65}$=A or G; wherein $X_{66}$ is absent or present, and when $X_{66}$ is present, $X_{66}$=A or G; wherein $X_{67}$ is absent or present, and when $X_{67}$ is present, $X_{67}$=A, T, or C; wherein $X_{68}$ is absent or present, and when $X_{68}$ is present, $X_{68}$=T, A, C or G; wherein $X_{69}$ is absent or present, and when $X_{69}$ is present, $X_{69}$=C, T, G or A; wherein $X_{70}$ is absent or present, and when $X_{70}$ is present, $X_{70}$=A, T or G; wherein $X_{71}$ is absent or present, and when $X_{71}$ is present, $X_{71}$=T or A; wherein $X_{72}$ is absent or present, and when $X_{72}$ is present, $X_{72}$=T or C; wherein $X_{73}$ is absent or present, and when $X_{73}$ is present, $X_{73}$=C, A or T; wherein $X_{74}$ is absent or present, and when $X_{74}$ is present, $X_{74}$=A, T or C; wherein $X_{75}$ is absent or present, and when $X_{75}$ is present, $X_{75}$=G, A, C or T; wherein $X_{76}$ is absent or present, and when $X_{76}$ is present, $X_{76}$=C or T; wherein $X_{77}$ is absent or present, and when $X_{77}$ is present, $X_{77}$=T, G, C or A; wherein $X_{78}$ is absent or present, and when $X_{78}$ is present, $X_{78}$=A, T or G; wherein $X_{79}$ is absent or present, and when $X_{79}$ is present, $X_{79}$=C, A or G; wherein $X_{80}$=C or T; wherein $X_{81}$ is absent or present, and when $X_{81}$ is present, $X_{81}$=T or C; wherein $X_{82}$ is absent or present, and when $X_{82}$ is present, $X_{82}$=G, A or T; wherein $X_{83}$ is absent or present, and when $X_{83}$ is present, $X_{83}$=G; wherein $X_{84}$ is absent or present, and when $X_{84}$ is present, $X_{84}$=G; wherein $X_{85}$ is absent or present, and when $X_{85}$ is present, $X_{85}$=C; wherein $X_{86}$ is absent or present, and when $X_{86}$ is present, $X_{86}$=A, G or T; wherein $X_{87}$ is absent or present, and when $X_{87}$ is present, $X_{87}$=G or A; wherein $X_{88}$ is absent or present, and when $X_{88}$ is present, $X_{88}$=A or G; wherein $X_{89}$ is absent or present, and when $X_{89}$ is present, $X_{89}$=G; wherein $X_{90}$ is absent or present, and when $X_{90}$ is present, $X_{90}$=G, T, A, or C; wherein $X_{91}$=G, T or C; wherein $X_{92}$=G, T or A; wherein $X_{93}$=G, A or T; wherein $X_{94}$=C, A or T; wherein $X_{95}$=C, T or G; wherein $X_{96}$=C, A, or G; wherein $X_{97}$=C, T, A or G; wherein $X_{98}$=T, C, G or A; wherein $X_{99}$=A, T, G or C; wherein $X_{100}$ is absent or present, and when $X_{100}$ is present, $X_{100}$=C; wherein $X_{101}$ is absent or present, and when $X_{101}$ is present, $X_{101}$=C; wherein $X_{102}$ is absent or present, and when $X_{102}$ is present, $X_{102}$=G, T, A or C; wherein $X_{103}$ is absent or present, and when $X_{103}$ is present, $X_{103}$=G, T, or A; wherein $X_{104}$ is absent or present, and when $X_{104}$ is present, $X_{104}$=T, C or G; wherein $X_{105}$ is absent or present, and when $X_{105}$ is present, $X_{105}$=T or G; wherein $X_{106}$ is absent or present, and when $X_{106}$ is present, $X_{106}$=T, A or G; wherein $X_{107}$ is absent or present, and when $X_{107}$ is present, $X_{107}$=T, A or C; wherein $X_{108}$ is absent or present, and when $X_{108}$ is present, $X_{108}$=A, G, T or C; wherein $X_{109}$ is absent or present, and when $X_{109}$ is present, $X_{109}$=A, T or G; wherein $X_{110}$ is absent or present, and when $X_{110}$ is present, $X_{110}$=C, T or G; wherein $X_{111}$ is absent or present, and when $X_{111}$ is present, $X_{111}$=T, or C; wherein $X_{112}$ is absent or present, and when $X_{112}$ is present, $X_{112}$=C, A, T or G; wherein $X_{113}$ is absent or present, and when $X_{113}$ is present, $X_{113}$=T, A or C; wherein $X_{114}$ is absent or present, and when $X_{114}$ is present, $X_{114}$=C, T or A; wherein $X_{115}$ is absent or present, and when $X_{115}$ is present, $X_{115}$=T, A, G or C; wherein $X_{116}$ is absent or present, and when $X_{116}$ is present, $X_{116}$=A or C; wherein $X_{17}$ is absent or present, and when $X_{117}$ is present, $X_{117}$=C, T, G or A; wherein $X_{118}$ is absent or present, and when $X_{118}$ is present, $X_{118}$=G, A, C or T; wherein $X_{119}$ is absent or present, and when $X_{119}$ is present, $X_{119}$=G, C or T; wherein $X_{120}$ is absent or present, and when $X_{120}$ is present, $X_{120}$=C, A or T; wherein $X_{121}$ is absent or present, and when $X_{121}$ is present, $X_{121}$=T, A, C or G; wherein $X_{122}$ is absent or present, and when $X_{122}$ is present, $X_{122}$=A, G, C or T; wherein $X_{123}$ is absent or present, and when $X_{123}$ is present, $X_{123}$=A, G, C or T; wherein $X_{124}$ is absent or present, and when $X_{124}$ is present, $X_{124}$=C or G; wherein $X_{125}$ is absent or present, and when $X_{125}$ is present, $X_{125}$=C or T; wherein $X_{126}$ is absent or present, and when $X_{126}$ is present, $X_{126}$=T, G or C; wherein $X_{127}$ is absent or present, and when $X_{127}$ is present, $X_{127}$=G, C or T; wherein $X_{128}$ is absent or present, and when $X_{128}$ is present, $X_{128}$=G; wherein $X_{129}$ is absent or present, and when $X_{129}$ is present, $X_{129}$=T; wherein $X_{130}$ is absent or present, and when $X_{130}$ is present, $X_{130}$=C; wherein $X_{131}$ is absent or present, and when $X_{131}$ is present, $X_{131}$=A; wherein $X_{132}$ is absent or present, and when $X_{132}$ is present, $X_{132}$=T; wherein $X_{133}$ is absent or present, and when $X_{133}$ is present, $X_{133}$=C; wherein $X_{134}$ is absent or present, and when $X_{134}$ is present, $X_{134}$=A; wherein $X_{135}$ is absent or present, and when $X_{135}$ is present, $X_{135}$=A; wherein $X_{136}$ is absent or present, and when $X_{136}$ is present, $X_{136}$=T; wherein $X_{137}$ is absent or present, and when $X_{137}$ is present, $X_{137}$=C; wherein $X_{138}$ is absent or present, and when $X_{138}$ is present, $X_{138}$=T; wherein $X_{139}$ is absent or present, and when $X_{139}$ is present, $X_{139}$=C; wherein $X_{140}$ is absent or present, and when $X_{140}$ is present, $X_{140}$=A; wherein $X_{141}$ is absent or present, and when $X_{141}$ is present, $X_{141}$=C; wherein $X_{142}$ is absent or present, and when $X_{142}$ is present, $X_{142}$=G; wherein $X_{143}$ is absent or present, and when $X_{143}$ is present, $X_{143}$=T; wherein $X_{144}$ is absent or present, and when $X_{144}$ is present, $X_{144}$=C; wherein $X_{145}$ is absent or present, and when $X_{145}$ is present, $X_{145}$=C; wherein $X_{146}$ is absent or present, and when $X_{146}$ is present, $X_{146}$=A, G, C or T; wherein $X_{147}$ is absent or present, and when $X_{147}$ is present, $X_{147}$=A, T, C or G; wherein $X_{148}$ is absent or present, and when $X_{148}$ is present, $X_{148}$=T, A, C or G; wherein $X_{149}$ is absent or present, and when $X_{149}$ is present, $X_{149}$=G, C, or A; wherein $X_{150}$ is absent or present, and when $X_{150}$ is present, $X_{150}$=G, C, A or T; wherein $X_{151}$ is absent or present, and when $X_{151}$ is present, $X_{151}$=A, C or T; wherein $X_{152}$ is absent or present, and when $X_{152}$ is present, $X_{152}$=C, G or T; wherein $X_{153}$ is absent or present, and when $X_{153}$ is present, $X_{153}$=T or C; wherein $X_{154}$ is absent or present, and when $X_{154}$ is present, $X_{154}$=A, T, G or C; wherein $X_{155}$ is absent or present, and when $X_{155}$ is present, $X_{155}$=C or T; wherein $X_{156}$ is absent or present, and when $X_{156}$ is present, $X_{156}$=G, T, A or C; wherein $X_{157}$ is absent or present, and when $X_{157}$ is present, $X_{157}$=A or G; wherein $X_{158}$ is absent or present, and when $X_{158}$ is present, $X_{158}$=C or T; wherein $X_{159}$ is absent or present, and when $X_{159}$ is present, $X_{159}$=A, T or G; wherein $X_{160}$ is absent or present, and when $X_{160}$ is present, $X_{160}$=T, A, C or G; wherein $X_{161}$ is absent or present, and when $X_{161}$ is present, $X_{161}$=A or T; wherein $X_{162}$ is absent or present, and when $X_{162}$ is present, $X_{162}$=G, T or A; wherein $X_{163}$ is absent or present, and when $X_{163}$ is present, $X_{163}$=A; wherein $X_{164}$ is absent or present, and when $X_{164}$ is present, $X_{164}$=C; wherein $X_{165}$ is absent or present, and when $X_{165}$ is present, $X_{165}$=G or A; wherein $X_{166}$ is absent or present, and when $X_{166}$ is present, $X_{166}$=C; wherein $X_{167}$ is absent or present, and when $X_{167}$ is present, $X_{167}$=T; wherein $X_{168}$ is absent or present, and when $X_{168}$ is present, $X_{168}$=C; wherein $X_{169}$ is absent or present, and when $X_{169}$ is present, $X_{169}$=G or A; wherein $X_{170}$ is absent or present, and when $X_{170}$ is present, $X_{170}$=T, G or A; wherein $X_{171}$ is absent or present, and when $X_{171}$ is present, $X_{171}$=C or T; wherein $X_{172}$ is absent or present, and when $X_{172}$ is present, $X_{172}$=T or C; wherein $X_{173}$ is absent or present, and when $X_{173}$ is present, $X_{173}$=A, G or T; wherein $X_{174}$ is absent or present, and when $X_{174}$ is present, $X_{174}$=G, A or T; wherein $X_{175}$ is absent or present, and when $X_{175}$ is present, $X_{175}$=T, C or A; wherein $X_{176}$ is absent or present, and when $X_{176}$ is present, $X_{176}$=C or T; wherein $X_{177}$ is absent or present, and when $X_{177}$ is present, $X_{177}$=C, A or T; wherein $X_{178}$ is absent or present, and when $X_{178}$ is present, $X_{178}$=G, A or C; wherein $X_{179}$ is absent or present, and when $X_{179}$ is present, $X_{179}$=C, A or T; wherein $X_{180}$ is absent or present, and when $X_{180}$ is present, $X_{180}$=C or T; wherein $X_{181}$ is absent or present, and when $X_{181}$ is present, $X_{181}$=A, C, G or T; wherein $X_{182}$ is absent or present, and when $X_{182}$ is present, $X_{182}$=A, T or C; wherein $X_{183}$ is absent or present, and when $X_{183}$ is present, $X_{183}$=G, T, A, or C; wherein $X_{184}$ is absent or present, and when $X_{184}$ is present, $X_{184}$=G, C or A; wherein $X_{185}$ is absent or present, and when $X_{185}$ is present, $X_{185}$=C or T; wherein $X_{186}$ is absent or present, and when $X_{186}$ is present, $X_{186}$=C, T or A; wherein $X_{187}$ is absent or present, and when $X_{187}$ is present, $X_{187}$=A or G; wherein $X_{188}$ is absent or present, and when $X_{188}$ is present, $X_{188}$=C or T; wherein $X_{189}$ is absent or present, and when $X_{189}$ is present, $X_{189}$=C, A or T; wherein $X_{190}$ is absent or present, and when $X_{190}$ is present, $X_{190}$=A, T, A or G; wherein $X_{191}$ is absent or present, and when $X_{191}$ is present, $X_{191}$=T, G, or A; wherein $X_{192}$ is absent or present, and when $X_{192}$ is present, $X_{192}$=A or T; wherein $X_{193}$ is absent or present, and when $X_{193}$ is present, $X_{193}$=T, or A; wherein $X_{194}$ is absent or present, and when $X_{194}$ is present, $X_{194}$=A or G; wherein $X_{195}$ is absent or present, and when $X_{195}$ is present, $X_{195}$=G, A, or T; wherein $X_{196}$ is absent or present, and when $X_{196}$ is present, $X_{196}$=G or T; wherein $X_{197}$ is absent or present, and when $X_{197}$ is present, $X_{197}$=T, C, or A; wherein $X_{198}$ is absent or present, and when $X_{198}$ is present, $X_{198}$=A or G; wherein $X_{199}$ is absent or present, and when $X_{199}$ is present, $X_{199}$=T or C; wherein $X_{200}$ is absent or present, and when $X_{200}$ is present, $X_{200}$=G, T, A or C; wherein $X_{201}$ is absent or present, and when $X_{201}$ is present, $X_{201}$=G, T or A; wherein $X_{202}$ is absent or present, and when $X_{202}$ is present, $X_{202}$=G, C or A; wherein $X_{203}$ is absent or present, and when $X_{203}$ is present, $X_{203}$=C or T; wherein $X_{204}$ is absent or present, and when $X_{204}$ is present, $X_{204}$=A or T; wherein $X_{205}$ is absent or present, and when $X_{205}$ is present, $X_{205}$=A, C or G; wherein $X_{206}$ is absent or present, and when $X_{206}$ is present, $X_{206}$=C or A; wherein $X_{207}$ is absent or present, and when $X_{207}$ is present, $X_{207}$=A or G; wherein $X_{208}$ is absent or present, and when $X_{208}$ is present, $X_{208}$=C; wherein $X_{209}$ is absent or present, and when $X_{209}$ is present, $X_{209}$=C; wherein $X_{210}$ is absent or present, and when $X_{210}$ is present, $X_{210}$=C or T; wherein $X_{211}$ is absent or present, and when $X_{211}$ is present, $X_{211}$=A or G; wherein $X_{212}$ is absent or present, and when $X_{212}$ is present, $X_{212}$=C or A; wherein $X_{213}$ is absent or present, and when $X_{213}$ is present, $X_{213}$=C or A; wherein $X_{214}$ is absent or present, and when $X_{214}$ is present, $X_{214}$=G; wherein $X_{215}$ is absent or present, and when $X_{215}$ is present, $X_{215}$=A; wherein $X_{216}$ is absent or present, and when $X_{216}$ is present, $X_{216}$=G; wherein $X_{217}$ is absent or present, and when $X_{217}$ is present, $X_{217}$=C; wherein $X_{218}$ is absent or present, and when $X_{218}$ is present, $X_{218}$=G; wherein $X_{219}$ is absent or present, and when $X_{219}$ is present, $X_{219}$=C; wherein $X_{220}$ is absent or present, and when $X_{220}$ is present, $X_{220}$=T; wherein $X_{221}$ is absent or present, and when $X_{221}$ is present, $X_{221}$=T; wherein $X_{222}$ is absent or present, and when $X_{222}$ is present, $X_{222}$=C; wherein $X_{223}$ is absent or present, and when $X_{223}$ is present, $X_{223}$=G; wherein $X_{224}$ is absent or present, and when $X_{224}$ is present, $X_{224}$=T; wherein $X_{225}$ is absent or present, and when $X_{225}$ is present, $X_{225}$=C; wherein $X_{226}$ is absent or present, and when $X_{226}$ is present, $X_{226}$=G; wherein $X_{227}$ is absent or present, and when $X_{227}$ is present, $X_{227}$=A; wherein $X_{228}$ is absent or present, and when $X_{228}$ is present, $X_{228}$=G; wherein $X_{229}$ is absent or present, and when $X_{229}$ is present, $X_{229}$=G; wherein $X_{230}$ is absent or present, and when $X_{230}$ is present, $X_{230}$=C; wherein $X_{231}$ is absent or present, and when $X_{231}$ is present, $X_{231}$=C; wherein $X_{232}$ is absent or present, and when $X_{232}$ is present, $X_{232}$=A; wherein $X_{233}$ is absent or present, and when $X_{233}$ is present, $X_{233}$=C; wherein $X_{234}$ is absent or present, and when $X_{234}$ is present, $X_{234}$=C.

Figure 2:
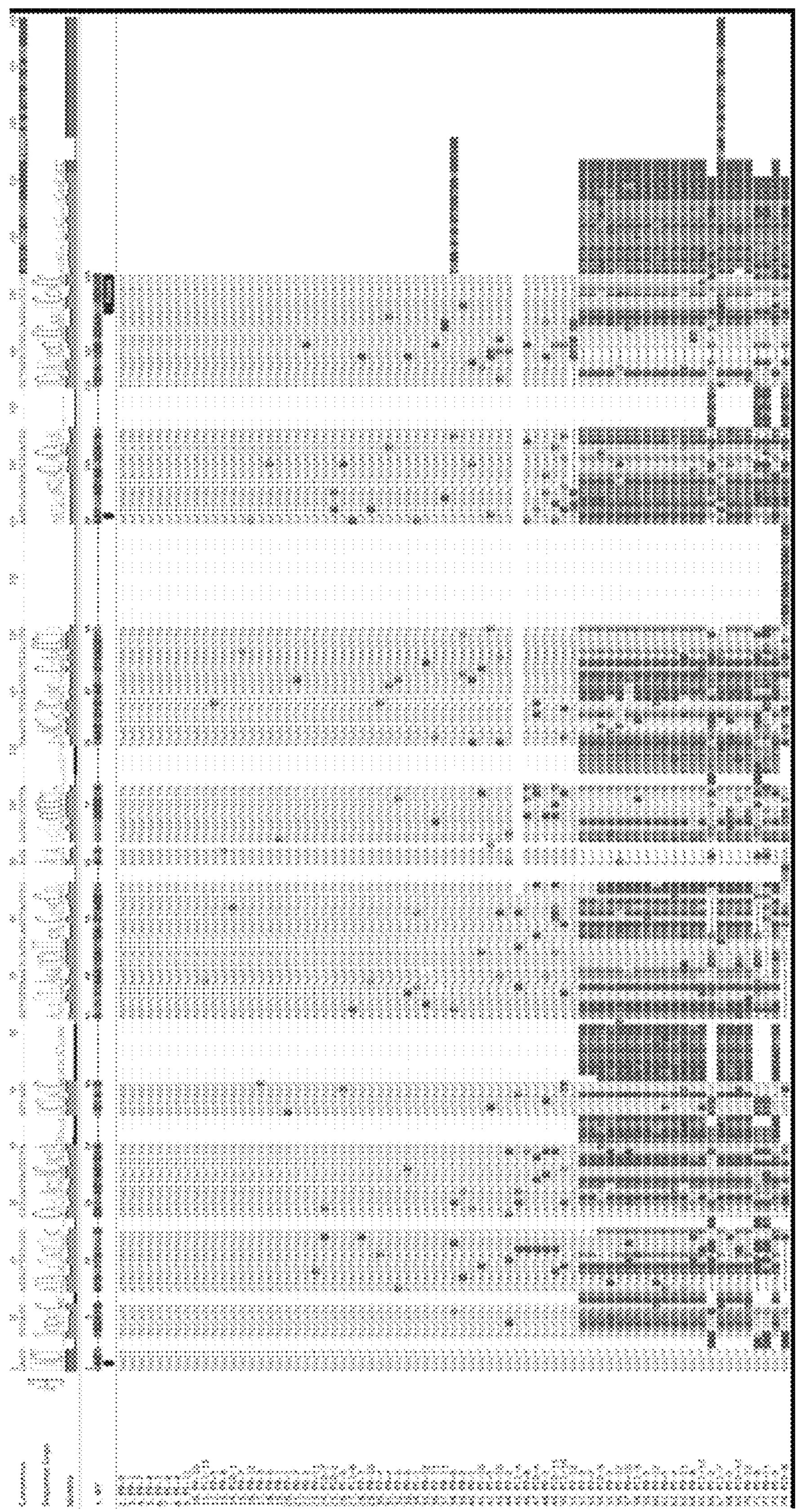
FIG. 2 is an illustration of the exemplary mutant subgenomic promoters in the subgenomic promoter library with annotated mutations as compared to wild type subgenomic promoter. Top to bottom, the sequences correspond to SEQ ID NOs: 80, 1, 1, 1, 1, 1, 1, 1, 19, 1, 1, 73, 31, 56, 60, 55, 50, 47, 44, 39, 27, 22, 17, 3, 64, 61, 10, 70, 29, 48, 30, 53, 32, 20, 5, 59, 37, 49, 54, 40, 16, 13, 9, 36, 28, 69, 34, 62, 18, 66, 72, 38, 35, 33, 65, 52, 15, 24, 68, 43, 4, 20, 8, 58, 46, 74, 6, 71, 7, 67, 26, 11, 25, 12, and 64.

Non-limiting exemplary sequences of mutant VEE virus subgenomic promoter region (−99/+30) are set forth in SEQ ID NOs: 2 to 74 (Kozak sequence in boldface if present; mutations in each mutant subgenomic promoter compared to wild type subgenomic promoter are annotated in FIG. 2). The sequences for SEQ ID NOs: 2, 14, 23, 41, 42, 45, 51, and 57 are not shown below because they are the same as the wild type subgenomic promoter (SEQ ID NO: 1).

(SEQ ID NO: 3)
GACTTCCATCATATTTATGGCCATGACTACTCTAGCTAGCAGTGTTAAAT
CATTCAGCTACCTGAGAGGGGCCCCTATAACTCTCTACGGCTAACCTGAA
TGGACTACGACATAGTCTAGTCCGCCAAGGCCACC

(SEQ ID NO: 4)
GACTTGATGTCGACATCTTTGGTCAGAATCACCATATCGGCGCTCGCCAC
ATCCTCCGCAGTCAGTTCATTTTCCAGACCGATTGACCCCTGGGTTTCTA
CTTTTACTTCCCAGCCTTTCGCTTTCGCGGCACTTTCCAGCGCCTCTGCT
GCCATTTAGGTGTGGGCAACACC (SEQ ID NO: 5)
GACTTCCATCATAGTTATGGCCATGACTACTCTAGCTAGCAGTGTGAAAT
CATTCAGCGACCTGAGAGGGGCCCCTATAACTCTCTACGGCTAACCTGTA
TGGACTACGACATAGTCTAGTCCGCCAAGGCCACC

-continued (SEQ ID NO: 6)
GACTCACCCACCACCACAGCAACGCGAGCACTCCATTTATCAGCGCAGGC
AAACTGTTTCTAAAAGTTGCCGCCACCGTTGTTGGTCATCAATTTCACGC
CCGGTAGTTCATCACGCAGACGCTCGGCTATTGCTATAGCCGCAGATAGT
GTATCAGCACC (SEQ ID NO: 7)
GACTTGATGCCGATATCTATGACCAGAATCGCCATATCAGCGCTCGCCTT
ATCTTCCGCAGTCAGTTCATTTTCCGGACCAATTAATTCCTGGGTTTCCA
CCTTCACTTCCCAGCCTTTCGCTTTCGCTGCAATATCCAGCGCCTCTGCT
GCCATATAGGTATGGGCAACACC (SEQ ID NO: 8)
GACTTGATGCCGATATCTTTGGTCAGATTCACCATATCAGCGCTCGCCAC
TTCTTCCGCAGTCAGTTCATTTTCCAGATCAAATGACCCCTGGGCTTCTA
CTTTCACTTCCCAGCCTTTCGCTTTCGCGGCAGTTTCCAGCGCCTCTGCT
GCCATATAGGTATGGGCAACACC (SEQ ID NO: 9)
GACTTCCATCATAGTTATGGCCATGACTACTCTAGATAGCAGTGTTAAAT
CATTCAGCTACCTGAGAGGGGGCCCCTATAACTCTCTACGGCTAACCTTA
TTGGACTACGACATAGTCTAGCTCGCCAAGGCCACC

(SEQ ID NO: 10)
GACTTCCATCATAGTTATGGCCATGACTACTCTAGCTATCAGTGTTAAAT
CATTCAGCTACCTGAGAGGGGCCCCTATAACTCTCTACGGCTAACCTGAA
TGGACTACAACATAGTCTAGTCCGCCAAGGCCACC

(SEQ ID NO: 11)
GACTCATCCAGCACCACAGCAACGCGGGTACCCCATTTATCAGCACGGGC
GAACTGTTTCTTGAAGTTGCCACCGCCAAGGTTGGTCATCAATTTCACGC
CCGGTAACTCATCACGCAGACACTCAGCTAATGCCATAGCCGCAGATTGT
GTATCAGCACC (SEQ ID NO: 12)
GACTTGATGCCGATATCTTTGATCAGTATCACCTTATCAACGCTAGCCAC
AACTTCCGCAGTCAGTGATTTTTCCAGACCAATTGACCCCAGGGTTTCTA
CTTTCACTTCCCTGCCTTTCGCATTCCCGGCACTTTCCAGCGCCTCTACT
GCAATATAGGTATGGGCAACACC (SEQ ID NO: 13)
GACTTCCATCATAGATATGGCCATGACTACTCTAGCTAGCAGTGTTAAAT
CTTTCAGCTACCTGAGAGGGCCCCCATAACTCTCTACGGATAACCTGAAT
GGACTACGACATAGTCTGGTCCGCCAAGGCCACC

(SEQ ID NO: 15)
GACTTGATGCCGATATCTTTGGTCAGAATCACCATATCAGCGCTCGCCAC
ATCTTCCTGTAGTCAGTTCATTTCCCTGACCATTTGACCCCTGGGTTTCT
ATTCTCACTTCCCAGCCTTTCGCTTTTGCAGCACTTTCTGGCGCCTCTGC
AGCCGTATAGGTATGGGCAACACC

-continued (SEQ ID NO: 16)
GACTTCCATCATAGTTATGGCCGTGACTACTCTAGCTAGCAGTGTTAAAT
CATTCAGCTACCTGAGAGGGGCCCCTAAAACTCTCTACCGCTAACCTGAA
TGGACTACTACATAGTCTAATCCGCCAAGGCCACC

(SEQ ID NO: 17)
GACTTCCATCATAGTTATGGCCATGACTACTCTAGCTAGCAGTGTTAAAT
CATTCAGCTACCTGAGAGGGGCCCCTATAACTCTCTACGGCTAACCTGAA
TGGACTACGACATAGTCTAGTCAGCCAAGGCCACC

(SEQ ID NO: 18)
GACTTCCATCATAGTTACGGCCATGACTCCTCAAGCAAGCAGTGTTAGAT
CATTCAGCTACCTGAGAGGGACCCTATAACTCTCTACGGCTAACCTGAAT
GGTCTTCGACATAGTCTAGACCGCCGAGGCCACC

(SEQ ID NO: 19)
GACTTCCATCATAGTTATGGCCATGACTACTCTAGCTAGCAGTGTTAAAT
CATTCAGCTACCTGAGAGGGGCCCCTATAACTCTCTACGGCTAACCTGAA
TGGACTACGACATAGTCTAGTCCGCCAAGGCCACC

(SEQ ID NO: 20)
GACTTGATGCCGTTATCTTTGGTCAGAATCACCATATCAGCGTTTGCCTC
ATCTCCCGCAGTCAGTTCATTTTCCAGACCAATTGACCCCTGGGTTTCTA
CTTTCACTTCCCAGCCTTTCGCTTTCGCGGCACTTTCCAGCGCCTCTGCT
GCCATATTGGTATGGGCAACACC (SEQ ID NO: 21)
GACTTCCATCATAGTTATGGCCATGACTATTCTAGCTAGCAGTGATAAAT
CATTCAGCTACCTGAGAGGGGCCCCTATAACTCTCTACGGCTAACCTGAA
TGGACTACGACATAGTCTAGCCCGCCAAGGCCACC

(SEQ ID NO: 22)
GACTTCCATCATAGTTATGGCCATGACTACTCTAGCTAGCAGTGTTAAAT
CATTCAGCTACCTGAGAGGGGCCCCTATAACTCTCTACAGCTAACCTGAA
TGGACTACGACATAGTCTAGTCCGCCAAGGCCACC

(SEQ ID NO: 24)
GACTTGATGCCGATATCATTAGTCAAAATCACCAAATCAGCGCTCGCCAC
ATCTTCCGCAGTCAGATCATTTTCCAGACCAATTGACCCCTGGGTTTCTA
CTTTCACTTCCAGCCTTTCGCTTTCGCGGCACTTTCCAGCGCTTCTGCTG
CCATATAGGTATGGGCAGCACC (SEQ ID NO: 25)
GACTCACCCAGCATCACAGCATCGCGGGCCCCCCATTTATCAGCACGGTA
AACAGTTTCTTAAAGCTGTCGCCGCCGTGGTTGGTCATCAATTCCACGCC
CGGTAATTCGTCATGCAGACGCTCATCTAATGCCATAGCCGCTGATTGTG
TATCAGCACC (SEQ ID NO: 26)
GACTTGATGTCGATATCTTTGGTCAGAATCACCATATCAGCGCTCGCCAC
ATCTTCCGCAATCAGTTCATTTTCCAGACCAATTGATGCCTGGGTTTCTA
CTTTCACTTCCCAGCCTTTCGCTTTCGCGGCACTTTTCAGCGCCTCTGCT
GCCATATAGGTATGGGCAACACC

-continued (SEQ ID NO: 27)
GACTTCCATCATAGTTATGGCCATGACTACTCTACCTAGCAGTGTTAAAT
CATTCAGCTACCTGAGAGGGGCCCCTATAACTCTCTACGGCTAACCTGAA
TGGACTACGACATAGTCTAGTCCGCCAAGGCCACC

(SEQ ID NO: 28)
GACTTCAATCATAGTCATGGCTATGACTACTCCAGCTAGCAGTGTTAAAT
CATTCAGCTACCTGGGAGTGGCCCCTATAACTCTCTACGGCTAACCTGAA
TGGACTACGACATAGTCTAGTTCGCCAAGGCCACC

(SEQ ID NO: 29)
GACTTCCATCATAGTTATGACCATGACTACTCTAGCTAGCAGTGTTAAAT
CATTCAGCTACCTGAGAGGGGCCCCTATAACTCTCTACGGCTAACCTGAA
TGGACTACGACATAGTCTAGCCCGCCAAGGCCACC

(SEQ ID NO: 30)
GACTTCCATCATAGTTTTGGCCATGACTACTCTAGCTAGCAGTGTTAAAT
CATTCAGCTACCTGAGAGGGGCCCCTATAACTCTTTACGGCTAACCTGAA
TGGACTACGACATAGTCTAGTCCGCCAAGGCCACC

(SEQ ID NO: 31)
GACTTCCATCATAGTTATGGCCATGACTACTCTAGCTAGCAGTGTTAAAT
CATTCAGCTACCTGAGAGGGGCCCCTATAACTCTTTACGGCTAACCTGAA
TGGACTACGACATAGTCTAGTCCGCCAAGGCCACC

(SEQ ID NO: 32)
GACTTCCATCTTAGTTATGGCCATGACTACTCTAGCTAGCAGTGTTAAAT
CATTCAGCTACCTGAGAGGGGCCCTTATAACTCTCTACTGCTAACCTGAA
TGGACTACGACATAGTCTAGTCCGCCAAGGCCACC

(SEQ ID NO: 33)
GACTTGATGCCGATATCTTTGGCAGAATCACCATATCAGCGCTCGCACAT
CTTCCGCAGTCAGTTCATTATCCAGACTGATTGACCCCTGGGTTTCTACT
TTCACTTCCCAGCCTTTCGCCTTCGCGGCACTTTCCAGCGCCTCTGCTGC
CATATAGGTATGGGCAACACC (SEQ ID NO: 34)
GACTTCCATCATAGTTACGGCCATGACTACTCGAGCTAGCAGTGTTAAAT
CATTCAGCTACCTGAGAGGGGACCTTTTAACTCTCTACGGCTAACCTGTA
TGGACTACGACAAAGTCTAGTCAGCCAAGGCCACC

(SEQ ID NO: 35)
GACTTGATGCCGATATCTTTGGCAGAATCACCATATCAGCGCTCGCACAT
CTTCCGCAGTCAGTTCATTATCCAGACTGATTGACCCCTGGGTTTCTACT
TTCACTTCCCAGCCTTTCGCCTTCGCGGCACTTTCCAGCGCCTCTGCTGC
CATATAGGTATGGGCAACACC (SEQ ID NO: 36)
GACTTCCATCATAGTTATGGCCATGACTACTCTAGCTAGCAGTGTTAGAT
CATTCAGCCACCTGAGAGGGGCCCCTAAAACTCTCTACGGCTGACCTGAA
TGGACTACGACATAGTTTAGTTCACCAAGGCCACC

(SEQ ID NO: 37)
GACTTCCATCATAGTTATGGCCATGACTACTCTAGCTAGCAGTGTTAAAT
CATTCAGCTACCTGAGAGGGACCCCTATGACTCTCTACGGCTAACCTGAA
TGGACTACGACATAGTCTAGTCAGCCAAGGCCACC

-continued (SEQ ID NO: 38)
GACTTCCATCATAGTTATGGCCATGACTACTCTAGCTAGCAGTGTTAAAT
CATTCAGCTACCTGAGAGGGGCCCCTATAACTCTCTACGGCTAACCTGAA
GAGCGCTTCCTCAGGCCACC

(SEQ ID NO: 39)
GACTTCCATCATAGTTATGGCCATGACTACTCTAGCTAGCAGTGTTAAAT
CATTCAGCTACCTGAGATGGGCCCCTATAACTCTCTACGGCTAACCTGAA
TGGACTACGACATAGTCTAGTCCGCCAAGGCCACC

(SEQ ID NO: 40)
GACTTCCATCATCGTTATGGCCATGGCTACTCTAGCTAGCAGTGTTAAAT
CATTCAGCTACCTGAGAGGGGCCCCTATAACTCTCTACGTCTAACCGGAA
TGGACTACGACATAGTCTAGTCCGCCAAGCCCACC (SEQ ID NO: 43)
GACTTGATGCCGATATCTTTGGTCAGAATCACCATATCAGCGCTCGCCAC
ATCTTCCGCAGTCAGTTCATTTTCTAGACCAATTGACCCCTGGGTTTCTA
CTTTCACTTCCCAGCCTTTCGCTTTCGCGGCACTTTCCAGCGCCTCTGCT
GCCATATAGGTATGGGCAACACC (SEQ ID NO: 44)
GACTTCCATCATAGTTATGGCCATGACTACTCTAGCTAGCAGTGTTAAAT
CATTCAGCTACCTGAGAGGGGCCCCTATAACTCTCTACGGCTAACCTGAA
TGGACTACTACATAGTCTAGTCCGCCAAGGCCACC

(SEQ ID NO: 46)
GACTTGATGCCGATATCCTTGCTCAGGATCACCGTATCAGCGCTCGCCAC
ATCTTCGGCAGTCAGTTCATTTTCCATACCAACTGGCCCCTGGGTTTCTA
CTTTCGCGTCCCAGCCTTTCGCTTTCGTGGCACTTTCCAGCATCTCTGCT
GCCATATAGGTATGTGCAACACC (SEQ ID NO: 47)
GACTTCCATCATAGTTATGGCCATGACTACTCTAGCTAGTAGTGTTAAAT
CATTCAGCTACCTGAGAGGGGCCCCTATAACTCTCTACGGCTAACCTGAA
TGGACTACGACATAGTCTAGTCCGCCAAGGCCACC

(SEQ ID NO: 48)
GACTTCCATCATAGTTATGGCCATGACTACTCTAGCTAGCAGTGTTGAAT
CATTCAGCTACCTGAGAGGGGCCCCTATAACTCTCTACGGCTAACCTGAA
CGGACTACGACATAGTCTAGTCCGCCAAGGCCACC

(SEQ ID NO: 49)
GACTTCCATCATAGTTATGGCCATGACTACTCTAGCTAGCAGTGTAAATC
ATTCAGCTACCTGAGAGGGGCCCCTATAACTCTCTACGGCTAACCTGAAT
GCACTACGACATAGTCTAGTCCGCACAGGCCACC

(SEQ ID NO: 50)
GACTTCCATCATAGTTATGGCCATGACTACTCTAGCTAGCAGTGTTAAAT
CATTCAGCTACCTGAGAGGGGCCCCTATAACTCTCTACGGCTAACCTGGA
TGGACTACGACATAGTCTAGTCCGCCAAGGCCACC

(SEQ ID NO: 52)
GACTTGACGCCGACATCTATGGTCAGAACCACCAAATCAGTGCTCGCCTC
ATCTTCTGCAGTAAGTTCATTTTCCAGACCAATCGACCCCTGGGTTTCTT
CTTTCTCTTCCCAGCCTTTCGCTTTCGCGGCACTTTCCAGCGCCCCTGCT
GCCATATAGGCATGGGTTACACC (SEQ ID NO: 53)
GACTTCCATCATAGTTATGGCCATGACTACTCTAGCTAGCAGTGTTAAAT
CATTCAGCTACCTGAGAGGGGCCCCTATAACTCTCTATGGCTAACCTGAA
TGGACTACGACTTAGTCTAGTCCGCCATGGCCACC

(SEQ ID NO: 54)
GACTTCCAGCATAGTTATCGCCAAGACTACTCTAGCTAGCATTGTTAAAT
CATTCAGCTACCTGAGAGGGGCCCCTATAACTCTCTACGGCTAACCTGAA
TGGACTACGACATTGTCTAGTCCGCCAAGGCCACCTGAAGAGCGCTTCCT
CAGCCCACC (SEQ ID NO: 55)
GACTTCCATCATAGTTATGGCCATGACTACTCTAGCTAGCAGTGTTAAAT
CATTCAGCTACCTGAGAGGGGCCCCTATAACTCTCTACGGCTAGCCTGAA
TGGACTACGACATAGTCTAGTCCGCCAAGGCCACC

(SEQ ID NO: 56)
GACTTCCATCATAGTTATGGCCATGACTACTCTAGCTAGCAGTGTTAAAT
CATTCAGCTACCTGAGGGGGGCCCCTATAACTCTCTACGGCTAACCTGAA
TGGACTACGACATAGTCTAGTCCGCCAAGGCCACC

(SEQ ID NO: 58)
GACTTGATGCAGGTATCTTTGGTCGGAACCACCATATCAACGCTCTCCAC
ATCCTCCGCAGTCAGCACATTATCCAGACCAATTGACCCCTGTGTTTCTA
CTATCTCTTCCCCACCTTTCGCTTTCGCGGCGCTTTCCTGCGCCTCTGCC
GCCATATAGGTATGGGCAACACC (SEQ ID NO: 59)
GACTTCCATCATAGTTATGGCCATGACTACTCTAGCTAGCAGAGTTAATC
ATTCAGCTACCTGAGAGGGGCCCCTATAACTCTCTACGGCAAACCTGAAT
GGACTACGACATAGTCTAGTCCGCCAAGGCCACC

(SEQ ID NO: 60)
GACTTCCATCATAGTTATGGCCATGACTACTCTAGCTAGCAGTGTTAAAT
CATTCAGCTTCCTGAGAGGGGCCCCTATAACTCTCTACGGCTAACCTGAA
TGGACTACGACATAGTCTAGTCCGCCAAGGCCACC

(SEQ ID NO: 61)
GACTTCCATCATAGTTATGGCCATGACTACTCTAGCTAGCAGTGTTAAAT
CATTCAGCTACCTGAGAGGGGCCCCTATAACTCTCTACGGCTAACCTGAA
AGGTCTACGACATAGTCTAGTCCGCCAAGGCCACC

(SEQ ID NO: 62)
GACTTCCATCATAGTTACGGCCATGACCACTATAGCTAGCAGTGTTAAAT
CATTAAGCTACCTAAGAGGGGCCCCCTTAACTATATACGGCTAACCTGAA
GGGCTACGACATAGTCTAGTCCGCCAAGGCCACC

(SEQ ID NO: 63)
GACTTCCATCATAGTTATGCCCTTGACTACTCTAGCTAGCAGTGTTAAAT
CATTCAGCTACCTGAGAGGGGCCCCTATAACTCTCTACGGCTAACCTGAA
TGGACTACGACATAGTCTAGTCCGCCAAGGCCACC

-continued (SEQ ID NO: 64)
GACTCACCCAGCACCACAGCAACACGGGCTACCCATTCATCAGCCTGGGC

AGACTGTTTCTTAAAGTTGCCGACGCCGCGCTTGGTCATCAATCTCACGT

CCGGTAATTCATCACTCAGACGCTCTGCTAATGCCATAGCCGCAGATTGT

GTATCAGCACC (SEQ ID NO: 65)
GACTTGATGCCGATATCTATGGTCAGGATCACCATTACGTCGCTCGCCAC

ATCTTTCGCAGTCAGTTCATTTTCCAGGCCTATTGACCCCTGGGTTTCTA

TTATCACTTCCCATCCTTTCGCATTCGCGGTACTTTCCAGCGCCTCTGCC

GCCAAATAGGTGTAGACTACACC (SEQ ID NO: 66)
GACTTCCATCATAATTAAGGCCATGACTACTCAAGCTAGCAGTGTTAAAT

CGTTCAGTCGCCTAAGAGGGGACACTTTAACTCTCTACGGCTAACCTGTA

TCGACTACGACTTAGTCTAGTCTGCCAAGGCCACC

(SEQ ID NO: 67)
GACTTGATGCCGATATCTTCGGTCAGAATCACCATATCAGCGCTCACAAC

ATCTTCACCAGTCAGTAGATTTTCCAGACCAATTGACCCGTGGGCTTCTA

CTTTCACTTCCCAGCCTTTCGCTTTCGCGGCACTTTCCAGCGCCTCTGCT

GCCTATAGGCATGGGCAACACC (SEQ ID NO: 68)
GACTTGATGCCGATATCTCTGGTCAGAATCACCATATCAGCGCTCGCCAT

ATCTTCCGCAGTCAGTTCATTTTCCAAACCAATTGACCCATGGGTTTCTA

CCTTCACTTCCCAGCCTTTCGCTTTCGCGGCACTTTCCAGCGCCTCTGCT

GCCATATAGTTATGGGCAACACC (SEQ ID NO: 69)
GACTTCCATCATAGTTACGGCCACGTCTACTCTAGCTTGCAGTGTCAAAT

CAATCAGCCACC

(SEQ ID NO: 70)
GACTTCCATCATAGTTATGGCCATGACTACTCTAGCTAGCAATGTTAAAT

CATTCAGCTACCTGAGAGGGGCCCCTATAACTCTCTACGGCTAACCTGCA

TGGACTACGACATAGTCTAGTCCGCCAAGGCCACC

(SEQ ID NO: 71)
GACTTGATGACGATATCTTTGGTCGGAATCACCATATCAATGCTCGCCAC

ATCTTCCGCGGTAAGTTCATCTTCCAGACAATTGACCCCTGGGTTACTAC

TATCACTTCCCTGCCTTACGCTTTGCGGCACTTACCAGCGCCTCCATTGC

CATATAGGAATGGGCAACACCTGAAGAGCGCTTCGTCGAGGCCACC

(SEQ ID NO: 72)
GACTTCCATCATAGATATGGCCAAGACTAGTCTAGCTATTAGTGATAAAT

CATTCAACTACCTGAGAGGGGCCCCCATTACTCACTACGGCTAACCTGAA

CGGAGTACGGCATTGTCTAGTCTGCCAAGGCCACC

(SEQ ID NO: 73)
GACTTCCATCATAGTTATGGCCATGACTACTCTAGCTAGCAGTGTTGAAT

CATTCAGCTACCTGAGAGGGGCCCCTATAACTCTCTACGGCTAACCTGAA

TGGACTACGACATAGTCTAGTCCGCCAAGGCCACC

-continued (SEQ ID NO: 74)
GACTTGATGCCGATATCTTAGGTCAGAATCACCATATCAGTGATCGCAAC

ATCTTCCGCAGACAATTCATTTTCCAAACCAATTGACCCCTGGGTTTCTA

CTTTCGCTTCTCAGCCTTTCGCTTTCGCGGCACTTTCCAGCGCCTCTGCT

GTCATAAAGGTATGGGCAACACC

A subgenomic promoter library, as used herein, refers to a plurality of subgenomic promoters, which includes mutant subgenomic promoters, and in some embodiments can include a wild type subgenomic promoter. In some instances, the subgenomic promoters in the library, each comprises a nucleic acid sequence at least 50%, 55%, 60%, 65%, 70%, 75%, 80%, 85%, 90%, 91%, 92%, 93%, 94%, 95%, 96%, 97%, 98%, 99% or 100% identical to nucleic acid sequences of SEQ IDs NO: 1-74 and 81. In some embodiments, the subgenomic promoters in the library, each comprises a nucleic acid sequence at least 80% identical to nucleic acid sequences of SEQ ID NO: 1-74 and 81. For example, an engineered subgenomic promoter may comprise a nucleotide sequence that is at least 85%, at least 90%, at least 95%, at least 97%, at least 98%, at least 99%, or at least 99.5% identical to the nucleotide sequence identified by any one of SEQ ID NOs: 1-74 and 81, and is able to regulate the expression (e.g., activate or repress) the sequence to which it is operably linked. In some embodiments, an engineered subgenomic promoter comprises a nucleotide sequence that is 95-99% identical to the nucleotide sequence identified by any one of SEQ ID NOs: 1-74 and 81, and is able to regulate the expression (e.g., activate or repress) the sequence to which it is operably linked. In some embodiments, an engineered subgenomic comprises a nucleotide sequence that is 95%-99%, 95%-98%, 95%-97%, 95%-96%, 96%-99%, 96%-98%, 96%-97%, 97%-99%, 97%-98%, or 98%-99% identical to the nucleotide sequence identified by any one of SEQ ID NOs: 1-74 and 81, and is able to regulate the expression (e.g., activate or repress) the sequence to which it is operably linked.

In some embodiments, each of the subgenomic promoters in the library is flanked by a pair of restriction endonucleases site at the 5' and the 3' end. A restriction endonuclease refers to an enzyme that cleaves DNA into fragments at or near specific recognition sites within the molecule known as restriction sites. Restrictions enzymes are one class of the broader endonuclease group of enzymes. Restriction enzymes are commonly classified into five types, which differ in their structure and whether they cut their DNA substrate at their recognition site, or if the recognition and cleavage sites are separate from one another. To cut DNA, all restriction enzymes make two incisions, once through each sugar-phosphate backbone (i.e. each strand) of the DNA double helix. These enzymes are found in bacteria and archaea and provide a defense mechanism against invading viruses. Inside a prokaryote, the restriction enzymes selectively cut up foreign DNA in a process called restriction digestion; meanwhile, host DNA is protected by a modification enzyme (a methyltransferase) that modifies the prokaryotic DNA and blocks cleavage. Together, these two processes form the restriction modification system. Over 3000 restriction enzymes have been studied in detail, and more than 600 of these are available commercially. These enzymes are routinely used for DNA modification in laboratories, and they are a vital tool in molecular cloning.

Restriction enzymes recognize a specific sequence of nucleotides and produce a double-stranded cut in the DNA.

The recognition sequences can also be classified by the number of bases in its recognition site, usually between 4 and 8 bases, and the number of bases in the sequence will determine how often the site will appear by chance in any given genome. Non-limiting examples of restriction endonucleases sites include DNA sequences that are recognized by SapI, AtaII, Acc65I, ApaI, BamHI, BcII, BgIII, ClaI, EcoRI, EcoRV, HindIII, KasI, KpnI, Mfel, Mlul, NspI, PciI, PstI, SacI, SphI, XbaI, or XhoI.

Other aspects of the present disclosure provide engineered subgenomic promoters having differential activities. "Having differential activities" means the activity of an engineered subgenomic promoter is higher or lower compared to each other. In some embodiments, the activity of an engineered subgenomic promoter is different from (higher or lower) the activity of another engineered subgenomic promoter by at least 10% (e.g., at least 10%, 20%, 30%, 40%, 50%, 60%, 70%, 80%, 90% 100%, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, or 1000-fold). In some embodiments, the activity of an engineered subgenomic promoter is different from (higher or lower) the activity of another subgenomic promoter by 10%-100%. For example, the activity of an engineered subgenomic promoter may be different from (higher or lower) the activity of another engineered subgenomic promoter by 10%-100%, 10%-90%, 10%-80%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100%. For example, the activity of an engineered subgenomic promoter may be different from (higher or lower) the activity of another engineered subgenomic promoter by 1-1000 fold. For example, the activity of an engineered subgenomic promoter may be different from (higher or lower) the activity of another engineered subgenomic promoter by 1-1000, 1-900, 1-800, 1-700, 1-600, 1-500, 1-400, 1-300, 1-200, 1-100, 1-90, 1-80, 1-70, 1-60, 1-50, 1-40, 1-30, 1-20, 1-10, 1-9, 1-8, 1-7, 1-6, 1-5, 1-4, 1-3, 1-2, 5-1000, 5-900, 5-800, 5-700, 5-600, 5-500, 5-400, 5-300, 5-200, 5-100, 5-90, 5-80, 5-70, 5-60, 5-50, 5-40, 5-30, 5-20, 5-10, 5-9, 5-8, 5-7, 5-6, 10-1000, 10-900, 10-800, 10-700, 10-600, 10-500, 10-400, 10-300, 10-200, 10-100, 10-90, 10-80, 10-70, 10-60, 10-50, 10-40, 10-30, 10-20, 20-1000, 20-900, 20-800, 20-700, 20-600, 20-500, 20-400, 20-300, 20-200, 20-100, 20-90, 20-80, 20-70, 20-60, 20-50, 20-40, 20-30, 30-1000, 30-900, 30-800, 30-700, 30-600, 30-500, 30-400, 30-300, 30-200, 30-100, 30-90, 30-80, 30-70, 30-60, 30-50, 30-40, 40-1000, 40-900, 40-800, 40-700, 40-600, 40-500, 40-400, 40-300, 40-200, 40-100, 40-90, 40-80, 40-70, 40-60, 40-50, 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 fold. Methods of measuring the activities of a promoter (e.g., an engineered subgenomic promoter) are known to those skilled in the art, e.g., as described in Jeyaseclan et al., Nucleic Acids Research. 29 (12), 2001; Allard et al., Cell Notes (21), 2008; and Zaslaver et al., Nature Methods. 3 (8): 623-628, 2006, each of which is incorporated herein by reference.

II. Engineered Nucleic Acid, Expression Cassettes and Vectors

(i) Engineered Nucleic Acid

Further provided herein are engineered nucleic acids (e.g., constructs) containing the engineered subgenomic promoters described herein. In some embodiments, an engineered subgenomic promoter is operably linked to a transgene (e.g., a nucleotide sequence encoding a gene). A promoter is considered to be "operably linked" when it is in a correct functional location and orientation in relation to a nucleic acid sequence it regulates to control ("drive") transcriptional initiation and/or expression of that sequence.

In some embodiments, an engineered subgenomic promoter is operably linked to a nucleotide sequence encoding a transgene, such that activation of the engineered subgenomic promoter results in expression of the transgene. The signal of the transgene may be detected and its intensity is an indication of the level of activation of the subgenomic promoter. As such, by comparing the signal from the transgene, the activities of a subgenomic promoter can be compared. The engineered subgenomic promoter provided herein can be operably linked to a transgene encoding any molecule of interest, such as nucleic acids (e.g., mRNA, inhibitory nucleic acids, etc.), endogenous proteins, recombinant proteins, detectable proteins, therapeutic proteins, enzymes, growth factors, cytokines, etc.

In some embodiments, the transgene encodes a detectable molecule, such as a detectable protein. In some embodiments, a detectable protein is a fluorescent protein. A fluorescent protein is a protein that emits a fluorescent light when exposed to a light source at an appropriate wavelength (e.g., light in the blue or ultraviolet range). Suitable fluorescent proteins that may be used as a detectable protein in the sensor circuit of the present disclosure include, without limitation, cGFP, eYFP, cCFP, mKate2, mCherry, mPlum, mGrape2, mRaspberry, mGrape1, mStrawberry, mTangerine, mBanana, and mHoneydew. In some embodiments, a detectable protein is an enzyme that hydrolyzes a substrate to produce a detectable signal (e.g., a chemiluminescent signal). Such enzymes include, without limitation, beta-galactosidase (encoded by LacZ), horseradish peroxidase, or luciferase. In some embodiments, the detectable molecule is a fluorescent RNA. A fluorescent RNA is an RNA aptamer that emits a fluorescent light when bound to a fluorophore and exposed to a light source at an appropriate wavelength (e.g., light in the blue or ultraviolet range). Suitable fluorescent RNAs that may be used include, without limitation, Spinach and Broccoli (e.g., as described in Paige et al., Science Vol. 333, Issue 6042, pp. 642-646, 2011, incorporated herein by reference).

In some embodiments, an engineered subgenomic promoter is operably linked to a transgene encoding a therapeutic molecule. A "therapeutic molecule" is a molecule that has therapeutic effects on a disease or condition, and may be used to treat a diseases or condition.

Therapeutic molecules of the present disclosure may be nucleic acid-based or protein or polypeptide-based. In some embodiments, the engineered subgenomic promoter drives the expression of the therapeutic molecule in a desired cell type (e.g., cancer cell) but not in other cell types, due to the engineered subgenomic promoter's cell-specific activity. As such, targeted therapy of diseases (e.g., cancer) is achieved.

In some embodiments, an engineered subgenomic promoter is operably linked to a transgene encoding a therapeutic nucleic acid. In some embodiments, nucleic acid-based therapeutic molecule may be an RNA interference (RNAi) molecule (e.g., a microRNA, siRNA, or shRNA) or a nucleic acid enzyme (e.g., a ribozyme). RNAi molecules and there use in silencing gene expression are familiar to those skilled in the art. In some embodiments, the RNAi molecule targets an oncogene. An oncogene is a gene that in certain circumstances can transform a cell into a tumor cell. An oncogene may be a gene encoding a growth factor or mitogen (e.g., c-Sis), a receptor tyrosine kinase (e.g., EGFR, PDGFR, VEGFR, or HER2/neu), a cytoplasmic tyrosine kinase (e.g., Src family kinases, Syk-ZAP-70 family kinases, or BTK family kinases), a cytoplasmic serine/threonine kinase or their regulatory subunits (e.g., Raf kinase or cyclin-dependent kinase), a regulatory GTPasc (e.g., Ras), or a transcription factor (e.g., Myc). In some embodiments, the oligonucleotide targets Lipocalin (Lcn2) (e.g., a Lcn2 siRNA). One skilled in the art is familiar with genes that may be targeted for the treatment of cancer.

In some embodiments, an engineered subgenomic promoter is operably linked to a transgene encoding a therapeutic protein. Non-limiting examples of protein or polypeptide-based therapeutic molecules include enzymes, regulatory proteins (e.g., immuno-regulatory proteins), antigens, antibodies or antibody fragments, and structural proteins.

Suitable enzymes (for operably linking to a subgenomic promoter) for some embodiments of this disclosure include, for example, oxidoreductases, transferases, polymerases, hydrolases, lyases, synthases, isomerases, and ligases, digestive enzymes (e.g., proteases, lipases, carbohydrases, and nucleases). In some embodiments, the enzyme is selected from the group consisting of lactase, beta-galactosidase, a pancreatic enzyme, an oil-degrading enzyme, mucinase, cellulase, isomaltase, alginase, digestive lipases (e.g., lingual lipase, pancreatic lipase, phospholipase), amylases, cellulases, lysozyme, proteases (e.g., pepsin, trypsin, chymotrypsin, carboxypeptidase, elastase), esterases (e.g. sterol esterase), disaccharidases (e.g., sucrase, lactase, beta-galactosidase, maltase, isomaltase), DNases, and RNases.

A regulatory protein may be, in some embodiments, a transcription factor or an immunoregulatory protein. Non-limiting, exemplary transcriptional factors include: those of the NFkB family, such as Rel-A, c-Rel, Rel-B, p50 and p52; those of the AP-1 family, such as Fos, FosB, Fra-1, Fra-2, Jun, JunB and JunD; ATF; CREB; STAT-1, -2, -3, -4, -5 and -6; NFAT-1, -2 and -4; MAF; Thyroid Factor; IRF; Oct-1 and -2; NF-Y; Egr-1; and USF-43, EGR1, Sp1, and E2F1. Other transcription factors may be operably linked to a subgenomic promoter, as provided herein. As used herein, an immunoregulatory protein is a protein that regulates an immune response. Non-limiting examples of immunoregulatory proteins include: antigens, adjuvants (e.g., flagellin, muramyl dipeptide), cytokines including interleukins (e.g., IL-2, IL-7, IL-15 or superagonist/mutant forms of these cytokines), IL-12, IFN-gamma, IFN-alpha, GM-CSF, FLT3-ligand), and immunostimulatory antibodies (e.g., anti-CTLA-4, anti-CD28, anti-CD3, or single chain/antibody fragments of these molecules). Other immunoregulatory proteins may be operably linked to a subgenomic promoter, as provided herein.

In some embodiments, the transgene encodes a heavy chain and/or a light chain of an antibody. In some embodiments, one of the subgenomic promoters described herein is operably linked to a transgene encoding the heavy chain of an antibody. In some embodiments, one of the subgenomic promoters described herein is operably linked to a transgene encoding the light chain of an antibody. An antibody (interchangeably used in plural form) is an immunoglobulin molecule capable of specific binding to a target antigen, through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, NANOBODIES®, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins are assigned to different classes. There are five major classes of immunoglobulins: IgA, IgD. IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. The term "isolated antibody" used herein refers to an antibody substantially free from naturally associated molecules, i.e., the naturally associated molecules constituting at most 20% by dry weight of a preparation containing the antibody. Purity can be measured by any appropriate method, e.g., column chromatography, polyacrylamide gel electrophoresis, and HPLC.

A typical antibody molecule comprises a heavy chain variable region (VH) and a light chain variable region (VL), which are usually involved in antigen binding. The VH and VL regions can be further subdivided into regions of hypervariability, also known as "complementarity determining regions" ("CDR"), interspersed with regions that are more conserved, which are known as "framework regions" ("FR"). Each VH and VL is typically composed of three CDRs and four FRs, arranged from amino-terminus to carboxy-terminus in the following order: FR1, CDR1, FR2, CDR2, FR3, CDR3, FR4.

Non-limiting examples of antibodies and fragments thereof include: an anti-CTLA-4 antibody such as ipilimumab (YERVOY®), bevacizumab (AVASTIN®), trastuzumab (HERCEPTIN®), alemtuzumab (CAMPATH®), indicated for B cell chronic lymphocytic leukemia), gemtuzumab (MYLOTARG®, hP67.6, anti-CD33, indicated for leukemia such as acute myeloid leukemia), rituximab (RITUXAN®), tositumomab (BEXXAR®, anti- CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUX®), MDX-447, MDX-22, MDX-220 (anti-TAG-72), IOR-C5, IOR-T6 (anti-CD1), IOR EGF/R3, celogovab (ONCOSCINT® OV103), cpratuzumab (LYMPHOCIDE®), pemtumomab (THERAGYN®), Gliomab-H (indicated for brain cancer, melanoma). In some embodiments, the engineered nucleic acid comprises a subgenomic promoter selected from the subgenomic promoter library and a heavy chain or a light chain of an anti-CTLA-4 antibody coding sequence operably linked to the subgenomic promoter. In some embodiments, the anti-CTLA-4 antibody is ipilimumab.

(ii) Expression Cassettes and Vectors

The present disclosure also provides expression cassettes comprising one or more engineered nucleic acids described herein. An expression cassettes, as used herein, refers to a DNA fragment comprises one or more engineered nucleic acid described herein, for expression of one or more transgenes. In some embodiments, the expression cassette comprises one engineered nucleic acid, which comprises a first subgenomic promoter selected from the subgenomic promoter library and a first transgene. Alternatively or in addition, the expression cassette can comprise a second engineered nucleic acid, which comprises a second subgenomic promoter selected from the subgenomic promoter library and a second transgene. In other embodiments, the expression cassette can comprise 1, 2, 3, 4, 5, 6, 7, 9, 10, or more engineered nucleic acids described herein. The one or more subgenomic promoter selected from the subgenomic promoter library can be the same or different. The one or more transgenes can be the same or different. In some instances, the expression cassette is an antibody expression cassette. An antibody expression cassette, as used herein, refers to a DNA fragment that expresses both the heavy chain and the light chain of the antibody to generate a functional antibody. In some examples, the antibody expression cassette comprises a first engineered nucleic acid expressing the heavy chain of an antibody; and a second engineered nucleic acid expressing the light chain of an antibody. In some embodiments, the antibody expression cassette comprises a first engineered nucleic acid comprising a first engineered subgenomic promoter selected from the engineered subgenomic promoter library operably linked to a first transgene, and the first transgene encodes a heavy chain of an antibody; and a second engineered nucleic acid comprising a second engineered subgenomic promoter selected from the engineered subgenomic promoter library operably linked to a second transgene, and the second transgene encodes a light chain of an antibody. In some embodiments, the first subgenomic promoter driving the expression of the heavy chain of the antibody, and the second subgenomic promoter driving the expression of the light chain of the same antibody are selected from the subgenomic promoter library to ensure the optimal production of functional antibodies.

Further provided herein are vectors that comprise one or more engineered nucleic acids or one or more expression cassettes described in the present disclosure. A vector includes any genetic element, such as a plasmid, phage, transposon, cosmid, chromosome, artificial chromosome, virus, virion, etc., which is capable of replication when associated with the proper control elements and which can transfer gene sequences between cells. Thus, the term vector includes cloning and expression vehicles, as well as viral vectors. In some instances, the vector is a plasmid, RNA replicon, linear double stranded DNA, viral vector, liposome or nanoparticle. As used herein, the term "RNA replicon" refers to a self-replicating genetic element comprised a RNA that replicates from one origin of replication. In some embodiments, the self-amplifying replicon RNA is derived from an alphavirus. Distinct from host mRNA, alphavirus replicon RNAs encode a set of four nonstructural proteins (nsPs 1-4) that are responsible both for genome replication and, when engineered to include genes encoding non-virus products, such as a transgene, provide for transcription of such non-viral products under the subgenomic promoter.

Cells comprising the engineered nucleic acids, expression cassettes and vectors are within the scope of the disclosure. The cell can be any cell suitable for producing the transgene. In some embodiments, the cells are mammalian cells, plant cells, insect cells, bacterial cells or fungi cells. In some examples, the cells are mammalian cells.

III. Applications of Subgenomic Promoter Library (i) Production of Transgene Encoded Molecules The present disclosure, at least in part, relates to a method of producing one or more transgene encoded molecules using the engineered nucleic acid described herein.

In some embodiments, the method comprises constructing one or more engineered nucleic acids described herein, for expression of one or more transgenes. In some examples, the engineered nucleic acid is prepared by recombinant technology as exemplified below. One or more transgenes are operably linked to a subgenomic promoter selected from the subgenomic promoter library provided herein and cloned into an expression vector.

In some embodiments, one or more engineered nucleic acids or one or more vectors (e.g., expression vectors) including engineered nucleic acids encoding the one or more transgenes may be introduced into suitable host cells for producing the transgene encoded molecules. The engineered nucleic acids or vectors can be introduced into host cells by conventional methods, e.g., liposome transfection, electroporation, or calcium phosphate precipitation. The host cells are cultured under suitable conditions for expression of the transgene thereof. In other embodiments, one or more engineered nucleic acid or one or more vectors including engineered nucleic acids encoding the one or more transgenes may be introduced into a host animal for producing the transgene encoded molecules in vivo by conventional methods in the art. Non-limiting exemplary suitable host animals can be humans or non-human mammals such as mice, goats, rabbits, pigs, donkeys, cows, or camels. Methods of introducing an engineered nucleic acid or vectors into a host animal are conventional in the art, for example, by recombinant viruses such as recombinant adeno-associated virus, recombinant lentivirus, liposome, nanoparticles, or microinjection.

Such transgene encoded molecules thereof can be recovered from the cultured cells (e.g., from the cells or the culture supernatant) via a conventional method, e.g., affinity purification.

Standard molecular biology techniques are used to prepare the recombinant expression vector, transfect the host cells, select for transformants, culture the host cells and recovery of the antibodies from the culture medium.

Non-limiting examples transgene encoded molecules include therapeutic molecules (e.g., cytokines, peptide based agonists), detectable molecules (e.g., fluorescent proteins), antibodies or antibody fragments, siRNA, enzymes, regulatory proteins (e.g., immuno-regulatory proteins), antigens, and structural proteins.

(ii) Fine Tune Expression Level of Multiple Transgenes on One Replicon RNA

Also provided herein are methods for selecting and using subgenomic promoters with differential levels to fine tune expression level of multiple transgenes on one vector. The methods comprise constructing an expression cassette library. In some embodiments, each expression cassette comprises more than one engineered nucleic acids. Each engineered nucleic acid can comprise a subgenomic promoter selected from the subgenomic promoter library operably linked to a different transgene. In some embodiments, the expression cassette is an antibody cassette. In some embodiments, the transgene is the heavy chain and the light chain of the antibody. In other embodiments, the transgene encodes a therapeutic molecule or a detectable molecule.

The library of the constructed expression cassettes can be introduced into suitable host cell. The host cells are cultured under suitable conditions for expression of the transgene thereof. The cells expressing desired level of each transgene can be selected by conventional methods (e.g., FACS sorting). In some embodiments, the transgenes encodes for a heavy chain and a light chain of an antibody, and the cells that express a desired level of functional antibody can be selected. In some embodiments, the nucleic acid sequences of the subgenomic promoters driving the transgenes can then be determined (e.g., by nucleic acid sequencing). Such subgenomic promoters can be selected to produce the transgenes at desired level. In some examples, the pair of subgenomic promoters that produce optimal level of functional antibodies can be selected for production of the antibody.

IV. General Techniques

The practice of the present invention will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995). Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Construction of Alphavirus Replicon Subgenomic Promoter Library

To precisely tune expression level of multiple transgenes from a single alphavirus replicon, libraries of subgenomic promoter (SGP) with differential activity (increased or decreased relative another subgenomic promoter in the library or wild type) was constructed. Subgenomic promoter mutants were generated using error-prone PCR, and specific mutants with varying expression level were screened. Utilization of the subgenomic promoter library is demonstrated by optimization of antibody expression.

Alphavirus derived wild type subgenomic promoter (assuming position +1 is the transcription start site) sequence from position −99 to +30 was flanked by SapI restriction site and subsequently cloned into vector pBjh6018. The nucleic acid sequence of the wild type subgenomic promoter is set forth in SEQ ID NO: 1 (−99 to 0 underlined; Kozak sequence in bold face):

(SEQ ID NO: 1)

GACTTCCATCATAGTTATGGCCATGACTACTCTAGCTAGCAGTGTTAAAT

CATTCAGCTACCTGAGAGGGGCCCCTATAACTCTCTACGGCTAACCTGAA

TGGACTACGACATAGTCTAGTCCGCCAAGGCCACC

The sequence of SapI flanked wild type subgenomic promoter is set forth in SEQ ID NO: 76 (SapI site in boldface):

(SEQ ID NO: 76)

GCTCTTCAGACTTCCATCATAGTTATGGCCATGACTACTCTAGCTAGCA

GTGTTAAATCATTCAGCTACCTGAGAGGGGCCCCTATAACTCTCTACGG

CTAACCTGAATGGACTACGACATAGTCTAGTCCGCCAAGGCCACCTGAA

GAGC

Mutants of the subgenomic promoter were created by error prone PCR using the GeneMorphII Random mutagenesis Kit (Agilent). The primers used in the PCR are:

Forward primer:
(SEQ ID NO: 77)
TATTGGGCGCTCTTCAGACT

Reverse primer:
(SEQ ID NO: 78)
GAGGAAGCGCTCTTCAGGTG

The PCR products contained various mutations of the subgenomic promoter, which were subjected to further screening for mutant subgenomic promoters that have differential activity in driving downstream gene expression.

The PCR products containing mutant subgenomic promoters (mutant SGP) were digested by SapI (SapI-mutant SGP-SapI) and ligated into the pBjh6031 vector, which comprises one wild type subgenomic promoter driving the expression of mVenus, and a Ptet promoter driving the expression of Red Fluorescence Protein (RFP), illustrated as Seq1_D1-CMV_nsP(1-4)-SGP1(−98/+30)_mVenus_3'UTR_SapI-Ptet-RFP-SapI_mKate_3'UTR-rb_glob_PA_Seq2. The sequence flanked by SapI sites are in Boldface. The SapI-mutant SGP-SapI was inserted into pBjh6031 to replace the SapI-Ptet-RFP-SapI. The resulting vectors comprises one wild type subgenomic promoter (referred to as SGP1) driving the expression of mVenus, and a mutant subgenomic promoter driving the expression of mKate, illustrated as Seq1_D1-CMV_nsP(1-4)-SGP1(−98/+30)_mVenus_3'UTR_SapI-mutant SGP-SapI_mKate_3'UTR-rb_glob_PA_Seq2. The ligated vectors were transformed into EC100D electrocompetent cell (Lucigen) by electroporation for further propagation and vector purification. The mutant SGP is referred to as SGP2.

One million of A549 cells were transfected with 7.5 μg of purified vectors, cultured for proper expression of mVenus and mKate and analyzed by Fluorescence Activated Cell Sorting (FACS). Cells expressing various levels of mVenus and mKate were sorted into eight different populations according to the gating strategy illustrated in FIG. 1A. Total RNA of each cell population was isolated for cDNA generation. cDNAs were digested with SapI and inserted into pBjh6031 for propagation and subsequent sequencing of the SGP2 region. For each gated region in FIG. 1A, 12 clones were picked and SGP2 region of the vectors isolated from each clone were sequenced. The results of the sequencing are shown in Table 1 and the mutations in each mutant subgenomic promoter are annotated as compared to wild type subgenomic promoter in FIG. 2.

TABLE 1

| ID | −99/+30/GCCACC (−99 underlined; Kozak sequence in boldface) | Length | SEQ ID NO |
|---|---|---|---|
| WT | GACTTCCATCATAGTTATGGCCATGACTACTCTAGCTAGCAGTGTTAAATCA TTCAGCTACCTGAGAGGGGCCCCTATAACTCTCTACGGCTAACCTGAATGGA CTACGACATAGTCTAGTCCGCCAAG**GCCACC** | 135 | 1 |
| P4-1 | Sequencing failed | 0 | |
| P4-2 | Sequencing failed | 0 | |
| P4-3 | Sequencing failed | 0 | |
| P4-4 | Sequencing failed | 0 | |
| P4-5 | Sequencing failed | 0 | |
| P4-6 | Sequencing failed | 0 | |
| P4-7 | Sequencing failed | 0 | |
| P4-8 | Sequencing failed | 0 | |
| P4-9 | Sequencing failed | 0 | |
| P4-10 | GACTTCCATCATAGTTATGGCCATGACTACTCTAGCTAGCAGTGTTAAATCA TTCAGCTACCTGAGAGGGGCCCCTATAACTCTCTACGGCTAACCTGAATGGA CTACGACATAGTCTAGTCCGCCAAGGCCACC | 135 | 1 |
| P4-11 | GACTTCCATCATATTTATGGCCATGACTACTCTAGCTAGCAGTGTTAAATCA TTCAGCTACCTGAGAGGGGCCCCTATAACTCTCTACGGCTAACCTGAATGGA ACTACGACATAGTCTAGTCCGCCAAGGCCACC | 135 | 3 |
| P4-12 | GACTTGATGTCGACATCTTTGGTCAGAATCACCATATCGGCGCTCGCCACAT CCTCCGCAGTCAGTTCATTTTCCAGACCGATTGACCCCTGGGTTTCTACTTT TACTTCCCAGCCTTTCGCTTTCGCGGCACTTTCCAGCGCCTCTGCTGCCATT TAGGTGTGGGCAACACC | 173 | 4 |
| P5-1 | GACTTCCATCATAGTTATGGCCATGACTACTCTAGCTAGCAGTGTGAAATCA TTCAGCGACCTGAGAGGGGCCCCTATAACTCTCTACGGCTAACCTGTATGGA CTACGACATAGTCTAGTCCGCCAAGGCCACC | 135 | 5 |
| P5-2 | GACTCACCCACCACCACAGCAACGCGAGCACTCCATTTATCAGCGCAGGCAA ACTGTTTCTAAAAGTTGCCGCCACCGTTGTTGGTCATCAATTTCACGCCCGG TAGTTCATCACGCAGACGCTCGGCTATTGCTATAGCCGCAGATAGTGTATCA GCACC | 161 | 6 |

TABLE 1-continued

| ID | -99/+30/GCCACC (-99 underlined; Kozak sequence in boldface) | Length | SEQ ID NO |
|---|---|---|---|
| P5-3 | GACTTGATGCCGATATCTATGACCAGAATCGCCATATCAGCGCTCGCCTTAT CTTCCGCAGTCAGTTCATTTTCCGGACCAATTAATTCCTGGGTTTCCACCTT CACTTCCCAGCCTTTCGCTTTCGCTGCAATATCCAGCGCCTCTGCTGCCATA TAGGTATGGGCAACACC | 173 | 7 |
| P5-4 | GACTTGATGCCGATATCTTTGGTCAGATTCACCATATCAGCGCTCGCCACTT CTTCCGCAGTCAGTTCATTTTCCAGATCAAATGACCCCTGGGCTTCTACTTT CACTTCCCAGCCTTTCGCTTTCGCGGCAGTTTCCAGCGCCTCTGCTGCCATA TAGGTATGGGCAACACC | 173 | 8 |
| P5-5 | GACTTCCATCATAGTTATGGCCATGACTACTCTAGATAGCAGTGTTAAATCA TTCAGCTACCTGAGAGGGGGCCCCTATAACTCTCTACGGCTAACCTTATTGG ACTACGACATAGTCTAGCTCGCCAAGGCCACC | 136 | 9 |
| P5-6 | GACTTCCATCATAGTTATGGCCATGACTACTCTAGCTATCAGTGTTAAATCA TTCAGCTACCTGAGAGGGGCCCCTATAACTCTCTACGGCTAACCTGAATGGA CTACAACATAGTCTAGTCCGCCAAGGCCACC | 135 | 10 |
| P5-7 | Sequencing failed | 0 | |
| P5-8 | GACTCATCCAGCACCACAGCAACGCGGGTACCCCATTTATCAGCACGGGCGA ACTGTTTCTTGAAGTTGCCACCGCCAAGGTTGGTCATCAATTTCACGCCCGG TAACTCATCACGCAGACACTCAGCTAATGCCATAGCCGCAGATTGTGTATCA GCACC | 161 | 11 |
| P5-9 | GACTTGATGCCGATATCTTTGATCAGTATCACCTTATCAACGCTAGCCACAA CTTCCGCAGTCAGTGATTTTTCCAGACCAATTGACCCCAGGGTTTCTACTTT CACTTCCCTGCCTTTCGCATTCCCGGCACTTTCCAGCGCCTCTACTGCAATA TAGGTATGGGCAACACC | 173 | 12 |
| P5-10 | GACTTCCATCATAGATATGGCCATGACTACTCTAGCTAGCAGTGTTAAATCT TTCAGCTACCTGAGAGGGCCCCCATAACTCTCTACGGATAACCTGAATGGAC TACGACATAGTCTGGTCCGCCAAGGCCACC | 134 | 13 |
| P5-11 | GACTTCCATCATAGTTATGGCCATGACTACTCTAGCTAGCAGTGTTAAATCA TTCAGCTACCTGAGAGGGGCCCCTATAACTCTCTACGGCTAACCTGAATGGA CTACGACATAGTCTAGTCCGCCAAGGCCACC | 135 | 1 |
| P5-12 | GACTTGATGCCGATATCTTTGGTCAGAATCACCATATCAGCGCTCGCCACAT CTTCCTGTAGTCAGTTCATTTCCCTGACCATTTGACCCCTGGGTTTCTATTC TCACTTCCCAGCCTTTCGCTTTTGCAGCACTTTCTGGCGCCTCTGCAGCCGT ATAGGTATGGGCAACACC | 174 | 15 |
| P6-1 | GACTTCCATCATAGTTATGGCCGTGACTACTCTAGCTAGCAGTGTTAAATCA TTCAGCTACCTGAGAGGGGCCCCTAAAACTCTCTACCGCTAACCTGAATGGA CTACTACATAGTCTAATCCGCCAAGGCCACC | 135 | 16 |
| P6-2 | GACTTCCATCATAGTTATGGCCATGACTACTCTAGCTAGCAGTGTTAAATCA TTCAGCTACCTGAGAGGGGCCCCTATAACTCTCTACGGCTAACCTGAATGGA CTACGACATAGTCTAGTCAGCCAAGGCCACC | 135 | 17 |
| P6-3 | GACTTCCATCATAGTTACGGCCATGACTCCTCAAGCAAGCAGTGTTAGATCA TTCAGCTACCTGAGAGGGACCCTATAACTCTCTACGGCTAACCTGAATGGTC TTCGACATAGTCTAGACCGCCGAGGCCACC | 134 | 18 |
| P6-4 | GACTTCCATCATAGTTATGGCCATGACTACTCTAGCTAGCAGTGTTAAATCA TTCAGCTACCTGAGAGGGGCCCCTATAACTCTCTACGGCTAACCTGAATGGA CTACGACATAGTCTAGTCCGCCAAGGCCACC | 135 | 19 |
| P6-5 | GACTTGATGCCGTTATCTTTGGTCAGAATCACCATATCAGCGTTTGCCTCAT CTCCCGCAGTCAGTTCATTTTCCAGACCAATTGACCCCTGGGTTTCTACTTT CACTTCCCAGCCTTTCGCTTTCGCGGCACTTTCCAGCGCCTCTGCTGCCATA TTGGTATGGGCAACACC | 173 | 20 |
| P6-6 | GACTTCCATCATAGTTATGGCCATGACTATTCTAGCTAGCAGTGATAAATCA TTCAGCTACCTGAGAGGGGCCCCTATAACTCTCTACGGCTAACCTGAATGGA CTACGACATAGTCTAGCCCGCCAAGGCCACC | 135 | 21 |
| P6-7 | GACTTCCATCATAGTTATGGCCATGACTACTCTAGCTAGCAGTGTTAAATCA TTCAGCTACCTGAGAGGGGCCCCTATAACTCTCTACAGCTAACCTGAATGGA CTACGACATAGTCTAGTCCGCCAAGGCCACC | 135 | 22 |
| P6-8 | GACTTCCATCATAGTTATGGCCATGACTACTCTAGCTAGCAGTGTTAAATCA TTCAGCTACCTGAGAGGGGCCCCTATAACTCTCTACGGCTAACCTGAATGGA CTACGACATAGTCTAGTCCGCCAAGGCCACC | 135 | 1 |
| P6-9 | Sequencing failed | 0 | |

TABLE 1-continued

| ID | -99/+30/GCCACC (-99 underlined; Kozak sequence in boldface) | Length | SEQ ID NO |
|---|---|---|---|
| P6-10 | GACTTGATGCCGATATCATTAGTCAAAATCACCAAATCAGCGCTCGCCACAT CTTCCGCAGTCAGATCATTTTCCAGACCAATTGACCCCTGGGTTTCTACTTT CACTTCCAGCCTTTCGCTTTCGCGGCACTTTCCAGCGCTTCTGCTGCCATAT AGGTATGGGCAGCACC | 172 | 24 |
| P6-11 | GACTCACCCAGCATCACAGCATCGCGGGCCCCCCATTTATCAGCACGGTAAA CAGTTTCTTAAAGCTGTCGCCGCCGTGGTTGGTCATCAATTCCACGCCCGGT AATTCGTCATGCAGACGCTCATCTAATGCCATAGCCGCTGATTGTGTATCAG CACC | 160 | 25 |
| P6-12 | GACTTGATGTCGATATCTTTGGTCAGAATCACCATATCAGCGCTCGCCACAT CTTCCGCAATCAGTTCATTTTCCAGACCAATTGATGCCTGGGTTTCTACTTT CACTTCCCAGCCTTTCGCTTTCGCGGCACTTTTCAGCGCCTCTGCTGCCATA TAGGTATGGGCAACACC | 173 | 26 |
| P7-1 | GACTTCCATCATAGTTATGGCCATGACTACTCTACCTAGCAGTGTTAAATCA TTCAGCTACCTGAGAGGGGCCCCTATAACTCTCTACGGCTAACCTGAATGGA CTACGACATAGTCTAGTCCGCCAAGGCCACC | 135 | 27 |
| P7-2 | GACTTCAATCATAGTCATGGCTATGACTACTCCAGCTAGCAGTGTTAAATCA TTCAGCTACCTGGGAGTGGCCCCTATAACTCTCTACGGCTAACCTGAATGGA CTACGACATAGTCTAGTTCGCCAAGGCCACC | 135 | 28 |
| P7-3 | GACTTCCATCATAGTTATGACCATGACTACTCTAGCTAGCAGTGTTAAATCA TTCAGCTACCTGAGAGGGGCCCCTATAACTCTCTACGGCTAACCTGAATGGA CTACGACATAGTCTAGCCCGCCAAGGCCACC | 135 | 29 |
| P7-4 | GACTTCCATCATAGTTTTGGCCATGACTACTCTAGCTAGCAGTGTTAAATCA TTCAGCTACCTGAGAGGGGCCCCTATAACTCTTTACGGCTAACCTGAATGGA CTACGACATAGTCTAGTCCGCCAAGGCCACC | 135 | 30 |
| P7-5 | GACTTCCATCATAGTTATGGCCATGACTACTCTAGCTAGCAGTGTTAAATCA TTCAGCTACCTGAGAGGGGCCCCTATAACTCTTTACGGCTAACCTGAATGGA CTACGACATAGTCTAGTCCGCCAAGGCCACC | 135 | 31 |
| P7-6 | GACTTCCATCTTAGTTATGGCCATGACTACTCTAGCTAGCAGTGTTAAATCA TTCAGCTACCTGAGAGGGGCCCTTATAACTCTCTACTGCTAACCTGAATGGA CTACGACATAGTCTAGTCCGCCAAGGCCACC | 135 | 32 |
| P7-7 | GACTTGATGCCGATATCTTTGGCAGAATCACCATATCAGCGCTCGCACATCT TCCGCAGTCAGTTCATTATCCAGACTGATTGACCCCTGGGTTTCTACTTTCA CTTCCCAGCCTTTCGCCTTCGCGGCACTTTCCAGCGCCTCTGCTGCCATATA GGTATGGGCAACACC | 171 | 33 |
| P7-8 | GACTTCCATCATAGTTACGGCCATGACTACTCGAGCTAGCAGTGTTAAATCA TTCAGCTACCTGAGAGGGGACCTTTTAACTCTCTACGGCTAACCTGTATGGA CTACGACAAAGTCTAGTCAGCCAAGGCCACC | 135 | 34 |
| P7-9 | GACTTGATGCCGATATCTTTGGCAGAATCACCATATCAGCGCTCGCACATCT TCCGCAGTCAGTTCATTATCCAGACTGATTGACCCCTGGGTTTCTACTTTCA CTTCCCAGCCTTTCGCCTTCGCGGCACTTTCCAGCGCCTCTGCTGCCATATA GGTATGGGCAACACC | 171 | 35 |
| P7-10 | GACTTCCATCATAGTTATGGCCATGACTACTCTAGCTAGCAGTGTTAGATCA TTCAGCCACCTGAGAGGGGCCCCTAAAACTCTCTACGGCTGACCTGAATGGA CTACGACATAGTTTAGTTCACCAAGGCCACC | 135 | 36 |
| P7-11 | GACTTCCATCATAGTTATGGCCATGACTACTCTAGCTAGCAGTGTTAAATCA TTCAGCTACCTGAGAGGGACCCCTATGACTCTCTACGGCTAACCTGAATGGA CTACGACATAGTCTAGTCAGCCAAGGCCACC | 135 | 37 |
| P7-12 | GACTTCCATCATAGTTATGGCCATGACTACTCTAGCTAGCAGTGTTAAATCA TTCAGCTACCTGAGAGGGGCCCCTATAACTCTCTACGGCTAACCTGAAGAGC GCTTCCTCAGGCCACC | 120 | 38 |
| P8-1 | GACTTCCATCATAGTTATGGCCATGACTACTCTAGCTAGCAGTGTTAAATCA TTCAGCTACCTGAGATGGGCCCCTATAACTCTCTACGGCTAACCTGAATGGA CTACGACATAGTCTAGTCCGCCAAGGCCACC | 135 | 39 |
| P8-2 | GACTTCCATCATCGTTATGGCCATGGCTACTCTAGCTAGCAGTGTTAAATCA TTCAGCTACCTGAGAGGGGCCCCTATAACTCTCTACGTCTAACCGGAATGGA CTACGACATAGTCTAGTCCGCCAAGCCCACC | 135 | 40 |
| P8-3 | GACTTCCATCATAGTTATGGCCATGACTACTCTAGCTAGCAGTGTTAAATCA TTCAGCTACCTGAGAGGGGCCCCTATAACTCTCTACGGCTAACCTGAATGGA CTACGACATAGTCTAGTCCGCCAAGGCCACC | 135 | 1 |

TABLE 1-continued

| ID | -99/+30/GCCACC (-99 underlined; Kozak sequence in boldface) | Length | SEQ ID NO |
|---|---|---|---|
| P8-4 | GACTTCCATCATAGTTATGGCCATGACTACTCTAGCTAGCAGTGTTAAATCA TTCAGCTACCTGAGAGGGGCCCCTATAACTCTCTACGGCTAACCTGAATGGA CTACGACATAGTCTAGTCCGCCAAGGCCACC | 135 | 1 |
| P8-5 | GACTTGATGCCGATATCTTTGGTCAGAATCACCATATCAGCGCTCGCCACAT CTTCCGCAGTCAGTTCATTTTCTAGACCAATTGACCCCTGGGTTTCTACTTT CACTTCCCAGCCTTTCGCTTTCGCGGCACTTTCCAGCGCCTCTGCTGCCATA TAGGTATGGGCAACACC | 173 | 43 |
| P8-6 | GACTTCCATCATAGTTATGGCCATGACTACTCTAGCTAGCAGTGTTAAATCA TTCAGCTACCTGAGAGGGGCCCCTATAACTCTCTACGGCTAACCTGAATGGA CTACTACATAGTCTAGTCCGCCAAGGCCACC | 135 | 44 |
| P8-7 | GACTTCCATCATAGTTATGGCCATGACTACTCTAGCTAGCAGTGTTAAATCA TTCAGCTACCTGAGAGGGGCCCCTATAACTCTCTACGGCTAACCTGAATGGA CTACGACATAGTCTAGTCCGCCAAGGCCACC | 135 | 1 |
| P8-8 | GACTTGATGCCGATATCCTTGCTCAGGATCACCGTATCAGCGCTCGCCACAT CTTCGGCAGTCAGTTCATTTTCCATACCAACTGGCCCCTGGGTTTCTACTTT CGCGTCCCAGCCTTTCGCTTTCGTGGCACTTTCCAGCATCTCTGCTGCCATA TAGGTATGTGCAACACC | 173 | 46 |
| P8-9 | GACTTCCATCATAGTTATGGCCATGACTACTCTAGCTAGTAGTGTTAAATCA TTCAGCTACCTGAGAGGGGCCCCTATAACTCTCTACGGCTAACCTGAATGGA CTACGACATAGTCTAGTCCGCCAAGGCCACC | 135 | 47 |
| P8-10 | GACTTCCATCATAGTTATGGCCATGACTACTCTAGCTAGCAGTGTTGAATCA TTCAGCTACCTGAGAGGGGCCCCTATAACTCTCTACGGCTAACCTGAACGGA CTACGACATAGTCTAGTCCGCCAAGGCCACC | 135 | 48 |
| P8-11 | GACTTCCATCATAGTTATGGCCATGACTACTCTAGCTAGCAGTGTAAATCAT TCAGCTACCTGAGAGGGGCCCCTATAACTCTCTACGGCTAACCTGAATGCAC TACGACATAGTCTAGTCCGCACAGGCCACC | 134 | 49 |
| P8-12 | GACTTCCATCATAGTTATGGCCATGACTACTCTAGCTAGCAGTGTTAAATCA TTCAGCTACCTGAGAGGGGCCCCTATAACTCTCTACGGCTAACCTGGATGGA CTACGACATAGTCTAGTCCGCCAAGGCCACC | 135 | 50 |
| P9-1 | GACTTCCATCATAGTTATGGCCATGACTACTCTAGCTAGCAGTGTTAAATCA TTCAGCTACCTGAGAGGGGCCCCTATAACTCTCTACGGCTAACCTGAATGGA CTACGACATAGTCTAGTCCGCCAAGGCCACC | 135 | 1 |
| P9-2 | Sequencing failed | 0 | |
| P9-3 | GACTTGACGCCGACATCTATGGTCAGAACCACCAAATCAGTGCTCGCCTCAT CTTCTGCAGTAAGTTCATTTTCCAGACCAATCGACCCCTGGGTTTCTTCTTT CTCTTCCCAGCCTTTCGCTTTCGCGGCACTTTCCAGCGCCCCTGCTGCCATA TAGGCATGGGTTACACC | 173 | 52 |
| P9-4 | GACTTCCATCATAGTTATGGCCATGACTACTCTAGCTAGCAGTGTTAAATCA TTCAGCTACCTGAGAGGGGCCCCTATAACTCTCTATGGCTAACCTGAATGGA CTACGACTTAGTCTAGTCCGCCATGGCCACC | 135 | 53 |
| P9-5 | Sequencing failed | 0 | |
| P9-6 | GACTTCCAGCATAGTTATCGCCAAGACTACTCTAGCTAGCATTGTTAAATCA TTCAGCTACCTGAGAGGGGCCCCTATAACTCTCTACGGCTAACCTGAATGGA CTACGACATTGTCTAGTCCGCCAAGGCCACCTGAAGAGCGCTTCCTCAGCCC ACC | 159 | 54 |
| P9-7 | GACTTCCATCATAGTTATGGCCATGACTACTCTAGCTAGCAGTGTTAAATCA TTCAGCTACCTGAGAGGGGCCCCTATAACTCTCTACGGCTAGCCTGAATGGA CTACGACATAGTCTAGTCCGCCAAGGCCACC | 135 | 55 |
| P9-8 | GACTTCCATCATAGTTATGGCCATGACTACTCTAGCTAGCAGTGTTAAATCA TTCAGCTACCTGAGGGGGGCCCCTATAACTCTCTACGGCTAACCTGAATGGA CTACGACATAGTCTAGTCCGCCAAGGCCACC | 135 | 56 |
| P9-9 | GACTTCCATCATAGTTATGGCCATGACTACTCTAGCTAGCAGTGTTAAATCA TTCAGCTACCTGAGAGGGGCCCCTATAACTCTCTACGGCTAACCTGAATGGA CTACGACATAGTCTAGTCCGCCAAGGCCACC | 135 | 1 |
| P9-10 | Sequencing failed | 0 | |

TABLE 1-continued

| ID | -99/+30/GCCACC (-99 underlined; Kozak sequence in boldface) | Length | SEQ ID NO |
|---|---|---|---|
| P9-11 | GACTTGATGCAGGTATCTTTGGTCGGAACCACCATATCAACGCTCTCCACAT CCTCCGCAGTCAGCACATTATCCAGACCAATTGACCCCTGTGTTTCTACTAT CTCTTCCCCACCTTTCGCTTTCGCGGCGCTTTCCTGCGCCTCTGCCGCCATA TAGGTATGGGCAACACC | 173 | 58 |
| P9-12 | GACTTCCATCATAGTTATGGCCATGACTACTCTAGCTAGCAGAGTTAATCAT TCAGCTACCTGAGAGGGGCCCCTATAACTCTCTACGGCAAACCTGAATGGAC TACGACATAGTCTAGTCCGCCAAGGCCACC | 134 | 59 |
| P10-1 | GACTTCCATCATAGTTATGGCCATGACTACTCTAGCTAGCAGTGTTAAATCA TTCAGCTTCCTGAGAGGGGCCCCTATAACTCTCTACGGCTAACCTGAATGGA CTACGACATAGTCTAGTCCGCCAAGGCCACC | 135 | 60 |
| P10-2 | GACTTCCATCATAGTTATGGCCATGACTACTCTAGCTAGCAGTGTTAAATCA TTCAGCTACCTGAGAGGGGCCCCTATAACTCTCTACGGCTAACCTGAAAGGT CTACGACATAGTCTAGTCCGCCAAGGCCACC | 135 | 61 |
| P10-3 | Sequencing failed | 0 | |
| P10-4 | GACTTCCATCATAGTTACGGCCATGACCACTATAGCTAGCAGTGTTAAATCA TTAAGCTACCTAAGAGGGGCCCCCTTAACTATATACGGCTAACCTGAAGGGC TACGACATAGTCTAGTCCGCCAAGGCCACC | 134 | 62 |
| P10-5 | Sequencing failed | 0 | |
| P10-6 | Sequencing failed | 0 | |
| P10-7 | GACTTCCATCATAGTTATGCCCTTGACTACTCTAGCTAGCAGTGTTAAATCA TTCAGCTACCTGAGAGGGGCCCCTATAACTCTCTACGGCTAACCTGAATGGA CTACGACATAGTCTAGTCCGCCAAGGCCACC | 135 | 63 |
| P10-8 | GACTCACCCAGCACCACAGCAACACGGGCTACCCATTCATCAGCCTGGGCAG ACTGTTTCTTAAAGTTGCCGACGCCGCGCTTGGTCATCAATCTCACGTCCGG TAATTCATCACTCAGACGCTCTGCTAATGCCATAGCCGCAGATTGTGTATCA GCACC | 161 | 64 |
| P10-9 | GACTTGATGCCGATATCTATGGTCAGGATCACCATTACGTCGCTCGCCACAT CTTTCGCAGTCAGTTCATTTTCCAGGCCTATTGACCCCTGGGTTTCTATTAT CACTTCCCATCCTTTCGCATTCGCGGTACTTTCCAGCGCCTCTGCCGCCAAA TAGGTGTAGACTACACC | 173 | 65 |
| P10-10 | Sequencing failed | 0 | |
| P10-11 | GACTTCCATCATAATTAAGGCCATGACTACTCAAGCTAGCAGTGTTAAATCG TTCAGTCGCCTAAGAGGGGACACTTTAACTCTCTACGGCTAACCTGTATCGA CTACGACTTAGTCTAGTCTGCCAAGGCCACC | 135 | 66 |
| P10-12 | GACTTGATGCCGATATCTTCGGTCAGAATCACCATATCAGCGCTCACAACAT CTTCACCAGTCAGTAGATTTTCCAGACCAATTGACCCGTGGGCTTCTACTTT CACTTCCCAGCCTTTCGCTTTCGCGGCACTTTCCAGCGCCTCTGCTGCCTAT AGGCATGGGCAACACC | 172 | 67 |
| P11-1 | Sequencing failed | 0 | |
| P11-2 | Sequencing failed | 0 | |
| P11-3 | GACTTGATGCCGATATCTCTGGTCAGAATCACCATATCAGCGCTCGCCATAT CTTCCGCAGTCAGTTCATTTTCCAAACCAATTGACCCATGGGTTTCTACCTT CACTTCCCAGCCTTTCGCTTTCGCGGCACTTTCCAGCGCCTCTGCTGCCATA TAGTTATGGGCAACACC | 173 | 68 |
| P11-4 | GACTTCCATCATAGTTACGGCCACGTCTACTCTAGCTTGCAGTGTCAAATCA ATCAGCCACC | 62 | 69 |
| P11-5 | Sequencing failed | 0 | |
| P11-6 | GACTTCCATCATAGTTATGGCCATGACTACTCTAGCTAGCAATGTTAAATCA TTCAGCTACCTGAGAGGGGCCCCTATAACTCTCTACGGCTAACCTGCATGGA CTACGACATAGTCTAGTCCGCCAAGGCCACC | 135 | 70 |
| P11-7 | GACTTGATGACGATATCTTTGGTCGGAATCACCATATCAATGCTCGCCACAT CTTCCGCGGTAAGTTCATCTTCCAGACAATTGACCCCTGGGTTACTACTATC ACTTCCCTGCCTTACGCTTTGCGGCACTTACCAGCGCCTCCATTGCCATATA GGAATGGGCAACACCTGAAGAGCGCTTCGTCGAGGCCACC | 196 | 71 |
| P11-8 | Sequencing failed | 0 | |

TABLE 1-continued

| ID | -99/+30/GCCACC (-99 underlined; Kozak sequence in boldface) | Length | SEQ ID NO |
|---|---|---|---|
| P11-9 | Sequencing failed | 0 | |
| P11-10 | GACTTCCATCATAGATATGGCCAAGACTAGTCTAGCTATTAGTGATAAATCA TTCAACTACCTGAGAGGGGCCCCCATTACTCACTACGGCTAACCTGAACGGA GTACGGCATTGTCTAGTCTGCCAAGGCCACC | 135 | 72 |
| P11-11 | GACTTCCATCATAGTTATGGCCATGACTACTCTAGCTAGCAGTGTTGAATCA TTCAGCTACCTGAGAGGGGCCCCTATAACTCTCTACGGCTAACCTGAATGGA CTACGACATAGTCTAGTCCGCCAAGGCCACC | 135 | 73 |
| P11-12 | GACTTGATGCCGATATCTTAGGTCAGAATCACCATATCAGTGATCGCAACAT CTTCCGCAGACAATTCATTTTCCAAACCAATTGACCCCTGGGTTTCTACTTT CGCTTCTCAGCCTTTCGCTTTCGCGGCACTTTCCAGCGCCTCTGCTGTCATA AAGGTATGGGCAACACC | 173 | 74 |
| Consensus | GACTTCCATCATACGTTATGGCCATGACTACTCTAGCTAGCAGTGTTAAATC ATTCAGCTACCTGAGAGGGGCCCCTATAACTCTCTACGGCTAACCTGAATGG ACTACGACATAGTCTAGTCCGCCAAGGCCACCATATAGGTATGGGCAACACC YRMMGAGCGCTTCGTCGAGGCCACC | | 80 |

Subsequently, a mutant SGP library is created to include SGP mutants that exhibit differential levels of activity. In addition, the library can be expanded to include more SGP mutants once more SGP mutant clones are screened and sequenced.

The strength of selected subgenomic promoters from the library were tested to validate that these promoters indeed have differential levels of activity. Each promoter was cloned into an individual vector driving the expression of the florescent protein mKate. The resulting vectors were amplified by inoculating each individual clones in 10 ml of Terrific Broth media (1:100 dilution from bacteria stock) supplemented with 100 μg/mL of carbenicillin. The cultures were incubated for 16 hours (overnight) at 37° C. on a shaker (225 rpm). Each vector was purified using QIAGEN® Plasmid Plus Midi Kit (Qiagen, Germany) and the concentration of each vector after purification was measured.

A549 cells were transfected with each of the purified vectors for expression of mKate driven by the subgenomic promoters. The expression level of mKate is directly proportional to the strength of the subgenomic promoters. A549 cells were grown to 70% confluency prior to transfection, and the cells were then trypsinized to obtain single cell suspension. One million cells were seeded into each well of a 24 well plates in 500 μL of DMEM/10% FBS.

To transfect the A549 cells with the purified vectors, 750 ng of each purified vector were mixed with 2.25 μL of ViaFect™ Transfection Reagent (Promega, USA) in 30 μL of OptiMeM, and added to the cells prepared in 24 well plate.

Figure 1B:
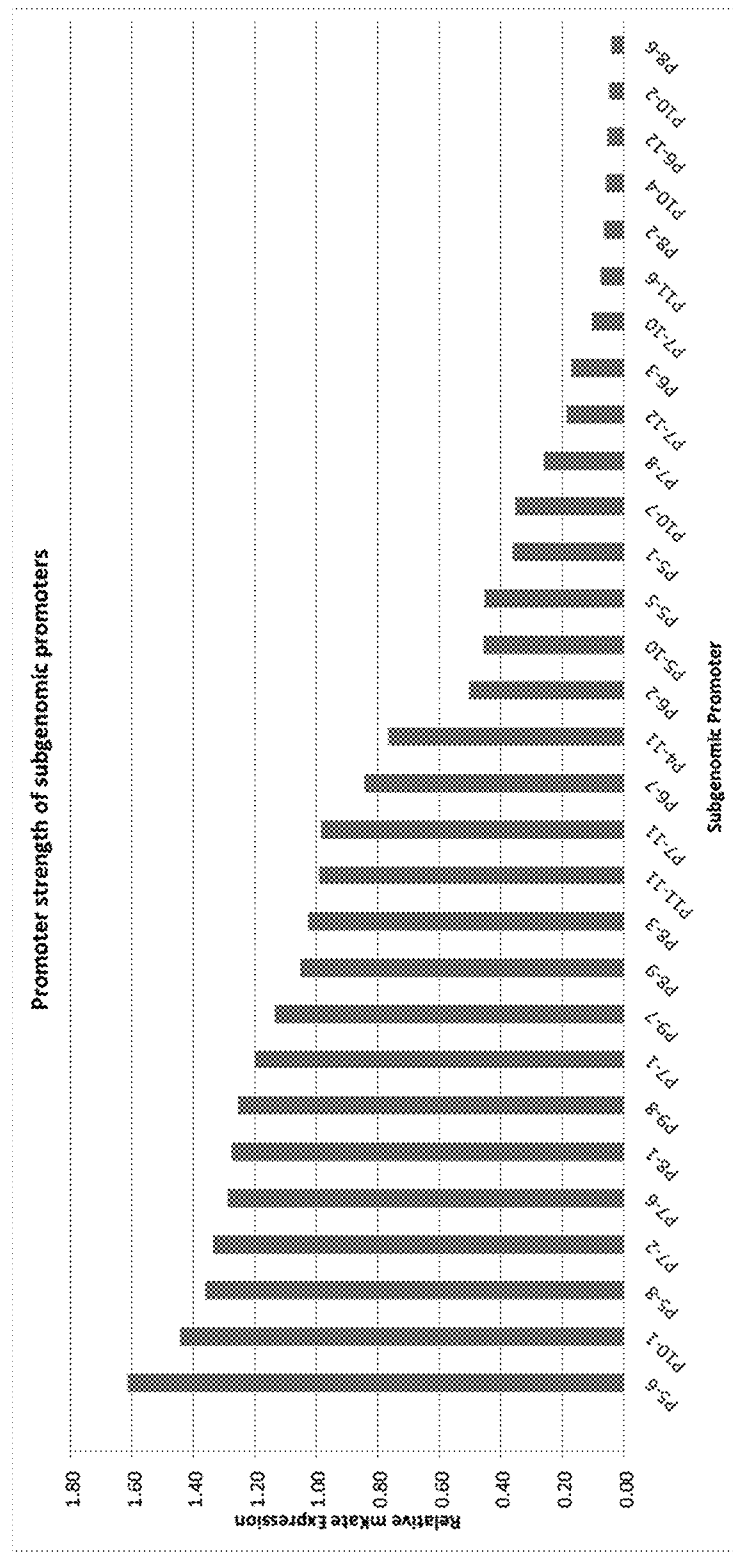

The cells were then incubated at 37° C. with 5% CO2 for 48 hours. The cells in each well were trypsinized and washed once with PBS. The cells were resuspended in the FACS buffer (1% BSA, 0.1% NaN3 sodium azide in PBS), and analyzed with LSR Fortessa (BD Biosciences, USA) for mKate expression. Geometric mean of mKate expression were calculated in mVenus positive cells, and relative mKate expression level was graphed. The results indicate that subgenomic mutant promoter strength vary between 161% of WT (P8-3) and 4% of WT. (FIG. 1B)

Example 2: Optimization of Antibody Expression by Expression Cassette Driven by Optimized Subgenomic Promoter Pair from the Library The SGP mutants identified in the library are used to tune expression level of multiple transgenes from a single alphavirus. The transgenes can be therapeutic molecules, e.g., cytokines, peptides, inhibitors. Moreover, the SGP mutants are used to optimize antibody expression, using an antibody expression cassette illustrated as: Seq1_D1-CMV_nsP(1-4)_SGP1 from subgenomic promoter library_Ipilimumab-HC_3'UTR_SGP2 from subgenomic promoter library_Ipilimumab-LC_3'UTR-rb_glob_PA_Seq2. Alternatively, SGP1 can drive the expression of the light chain of Ipilimumab, while SGP2 can drive the expression of the heavy chain of Ipilimumab. In this construct, the expression of Ipilimumab heavy chain was driven by one of the mutant SGPs selected from the SGP mutant library (SGP1), and the expression of Ipilimumab light chain was driven by another one of the mutant SGPs selected from the SGP mutant library (SGP2). Various SGP1/SGP2 pairs are used to express Ipilimumab. The constructs can then be delivered into suitable cells for expression of the Ipilimumab. The levels of functional Ipilimumab expressed by the expression cassette with different pairs of SGP1 and SGP2 are measured and compared. The expression cassette with SGP1/SGP2 pair that produces the highest level of Ipilimumab is selected for future Ipilimumab production. Likewise, the method is used to select expression cassettes for other antibodies, as well as other molecules, such as therapeutic molecules or detectable molecules.

Other Embodiments

1. An engineered subgenomic promoter library, comprising a plurality of promoters, wherein each promoter comprises a nucleotide sequence of $$GACTX_1X_2X_3X_4X_5X_6X_7X_8X_9X_{10}X_{11}X_{12}X_{13}X_{14}X_{15}X_{16}X_{17}X_{18}X_{19}X_{20}$$
$$X_{21}X_{22}X_{23}X_{24}X_{25}X_{26}X_{27}X_{28}X_{29}X_{30}X_{31}X_{32}X_{33}X_{34}X_{35}X_{36}X_{37}X_{38}X_{39}$$
$$X_{40}X_{41}X_{42}X_{43}X_{44}X_{45}X_{46}X_{47}X_{48}X_{49}X_{50}X_{51}X_{52}X_{53}X_{54}X_{55}X_{56}X_{57}X_{58}$$
$$X_{59}X_{60}X_{61}X_{62}X_{63}X_{64}X_{65}X_{66}X_{67}X_{68}X_{69}X_{70}X_{71}X_{72}X_{73}X_{74}X_{75}X_{76}X_{77}$$
$$X_{78}X_{79}X_{80}X_{81}X_{82}X_{83}X_{84}X_{85}X_{86}X_{87}X_{88}X_{89}X_{90}X_{91}X_{92}X_{93}X_{94}X_{95}X_{96}$$
$$X_{97}X_{98}X_{99}X_{100}X_{101}X_{012}X_{103}X_{104}X_{105}X_{106}X_{107}X_{108}X_{109}X_{110}X_{111}$$
$$X_{112}X_{113}X_{114}X_{115}X_{116}X_{117}X_{118}X_{119}X_{120}X_{121}X_{122}X_{123}X_{124}X_{125}$$

-continued $X_{126}X_{127}X_{128}X_{129}X_{130}X_{131}X_{132}X_{133}X_{134}X_{135}X_{136}X_{137}X_{138}X_{139}$ $X_{140}X_{141}X_{142}X_{143}X_{144}X_{145}X_{146}X_{147}X_{148}X_{149}X_{150}X_{151}X_{152}X_{153}$ $X_{154}X_{155}X_{156}X_{157}X_{158}X_{159}X_{160}X_{161}X_{162}X_{163}X_{164}X_{165}X_{166}X_{167}$ $X_{168}X_{169}X_{170}X_{171}X_{172}X_{173}X_{174}X_{175}X_{176}X_{177}X_{178}X_{179}X_{180}X_{181}$ $X_{182}X_{183}X_{184}X_{185}X_{186}X_{187}X_{188}X_{189}X_{199}X_{200}X_{201}X_{201}X_{203}X_{204}$ $X_{205}X_{206}X_{207}X_{208}X_{209}X_{210}X_{211}X_{212}X_{213}X_{214}X_{215}X_{216}X_{217}X_{218}$ $X_{219}X_{220}X_{221}X_{222}X_{223}X_{224}X_{225}X_{226}X_{227}X_{228}X_{229}X_{230}X_{231}X_{232}$ $X_{233}X_{234}$, wherein $X_1$ is absent or present, and when $X_1$ is present, $X_1$=C; wherein $X_2$ is absent or present, and when $X_2$ is present, $X_2$=A; wherein $X_3$=T or C; wherein $X_4$=C or G; wherein $X_5$=C or A; wherein $X_6$=C, T or A; wherein $X_7$=T, G or C; wherein $X_8$=C, T or A; wherein $X_9$ is absent or present, and when $X_9$ is present, $X_9$=C or A; wherein $X_{10}$ is absent or present, and when $X_{10}$ is present, $X_{10}$=G; wherein $X_{11}$ is absent or present, and when $X_{11}$ is present, $X_{11}$=T, A or G; wherein $X_{12}$ is absent or present, and when $X_{12}$ is present, $X_{12}$=T or C; wherein $X_{13}$ is absent or present, and when $X_{13}$ is present, $X_{13}$=A or C; wherein $X_{14}$=G, T or A; wherein $X_{15}$=T, A or C; wherein $X_{16}$=T, C or A; wherein $X_{17}$=A, T or C; wherein $X_{18}$=T, C or A; wherein $X_{19}$=G, C or A; wherein $X_{20}$=G, C or A; wherein $X_{21}$ is absent or present, and when $X_{21}$ is present, $X_{21}$=C or T; wherein $X_{22}$ is absent or present, and when $X_{22}$ is present, $X_{22}$=A; wherein $X_{23}$ is absent or present, and when $X_{23}$ is present, $X_{23}$=A or T; wherein $X_{24}$=C or T; wherein $X_{25}$=A, T or G; wherein $X_{26}$=T, A, C, or G; wherein $X_{27}$=G, T or A; wherein $X_{28}$=A, G, or T; wherein $X_{29}$=C, T, or G; wherein $X_{30}$=T, C or A; wherein $X_{31}$=A, C or G; wherein $X_{32}$=C, T, or G; wherein $X_{33}$=T, C or A; wherein $X_{34}$=C, A, G or T; wherein $X_{35}$=T, C, G or A; wherein $X_{36}$=A, T or G; wherein $X_{37}$ is absent or present, and when $X_{37}$ is present, $X_{37}$=T or A; wherein $X_{38}$ is absent or present, and when $X_{38}$ is present, $X_{38}$=C or T; wherein $X_{39}$ is absent or present, and when $X_{39}$ is present, $X_{39}$=A, G or T; wherein $X_{40}$ is absent or present, and when $X_{40}$ is present, $X_{40}$=G, A or T; wherein $X_{41}$ is absent or present, and when $X_{41}$ is present, $X_{41}$=C or T; wherein $X_{42}$=G, C or A; wherein $X_{43}$=C, A or T; wherein $X_{44}$=T, A or C; wherein $X_{45}$=A, T or C; wherein $X_{46}$=G, T, A or C; wherein $X_{47}$=C or T; wherein $X_{48}$ is absent or present, and when $X_{48}$ is present, $X_{48}$=C or A; wherein $X_{49}$ is absent or present, and when $X_{49}$ is present, $X_{49}$=A or T; wherein $X_{50}$ is absent or present, and when $X_{50}$ is present, $X_{50}$=C or T; wherein $X_{51}$ is absent or present, and when $X_{51}$ is present, $X_{51}$=A or T; wherein $X_{52}$ is absent or present, and when $X_{52}$ is present, $X_{52}$=T or A; wherein $X_{53}$ is absent or present, and when $X_{53}$ is present, $X_{53}$=C; wherein $X_{54}$ is absent or present, and when $X_{54}$ is present, $X_{54}$=T or C; wherein $X_{55}$ is absent or present, and when $X_{55}$ is present, $X_{55}$=T or C; wherein $X_{56}$ is absent or present, and when $X_{56}$ is present, $X_{56}$=C; wherein $X_{57}$ is absent or present, and when $X_{57}$ is present, $X_{57}$=C, T, G or A; wherein $X_{58}$ is absent or present, and when $X_{58}$ is present, $X_{58}$=T; wherein $X_{59}$ is absent or present, and when $X_{59}$ is present, $X_{59}$=A, G or C; wherein $X_{60}$ is absent or present, and when $X_{60}$ is present, $X_{60}$=G, A, T, C; wherein $X_{61}$ is absent or present, and when $X_{61}$ is present, $X_{61}$=T, A, or G; wherein $X_{62}$ is absent or present, and when $X_{62}$ is present, $X_{62}$=G or A; wherein $X_{63}$ is absent or present, and when $X_{63}$ is present, $X_{63}$=T, A, or G; wherein $X_{64}$ is absent or present, and when $X_{64}$ is present, $X_{64}$=T, G, C, or A; wherein $X_{65}$ is absent or present, and when $X_{65}$ is present, $X_{65}$=A or G; wherein $X_{66}$ is absent or present, and when $X_{66}$ is present, $X_{66}$=A or G; wherein $X_{67}$ is absent or present, and when $X_{67}$ is present, $X_{67}$=A, T, or C; wherein $X_{68}$ is absent or present, and when $X_{68}$ is present, $X_{68}$=T, A, C or G; wherein $X_{69}$ is absent or present, and when $X_{69}$ is present, $X_{69}$=C, T, G or A; wherein $X_{70}$ is absent or present, and when $X_{70}$ is present, $X_{70}$=A, T or G; wherein $X_{71}$ is absent or present, and when $X_{71}$ is present, $X_{71}$=Tor A; wherein $X_{72}$ is absent or present, and when $X_{72}$ is present, $X_{72}$=T or C; wherein $X_{73}$ is absent or present, and when $X_{73}$ is present, $X_{73}$=C, A or T; wherein $X_{74}$ is absent or present, and when $X_{74}$ is present, $X_{74}$=A, T or C; wherein $X_{75}$ is absent or present, and when $X_{75}$ is present, $X_{75}$=G, A, C or T; wherein $X_{76}$ is absent or present, and when $X_{76}$ is present, $X_{76}$=C or T; wherein $X_{77}$ is absent or present, and when $X_{77}$ is present, $X_{77}$=T, G, C or A; wherein $X_{78}$ is absent or present, and when $X_{78}$ is present, $X_{78}$=A, T or G; wherein $X_{79}$ is absent or present, and when $X_{79}$ is present, $X_{79}$=C, A or G; wherein $X_{80}$=C or T; wherein $X_{81}$ is absent or present, and when $X_{81}$ is present, $X_{81}$=T or C; wherein $X_{82}$ is absent or present, and when $X_{82}$ is present, $X_{82}$=G, A or T; wherein $X_{83}$ is absent or present, and when $X_{83}$ is present, $X_{83}$=G; wherein $X_{84}$ is absent or present, and when $X_{84}$ is present, $X_{84}$=G; wherein $X_{85}$ is absent or present, and when $X_{85}$ is present, $X_{85}$=C; wherein $X_{86}$ is absent or present, and when $X_{86}$ is present, $X_{86}$=A, G or T; wherein $X_{87}$ is absent or present, and when $X_{87}$ is present, $X_{87}$=G or A; wherein $X_{88}$ is absent or present, and when $X_{88}$ is present, $X_{88}$=A or G; wherein $X_{89}$ is absent or present, and when $X_{89}$ is present, $X_{89}$=G; wherein $X_{90}$ is absent or present, and when $X_{90}$ is present, $X_{90}$=G, T, A, or C; wherein $X_{91}$=G, T or C; wherein $X_{92}$=G, T or A; wherein $X_{93}$=G, A or T; wherein $X_{94}$=C, A or T; wherein $X_{95}$=C, T or G; wherein $X_{96}$=C, A, or G; wherein $X_{97}$=C, T, A or G; wherein $X_{98}$=T, C, G or A; wherein $X_{99}$=A, T, G or C; wherein $X_{100}$ is absent or present, and when $X_{100}$ is present, $X_{100}$=C; wherein $X_{101}$ is absent or present, and when $X_{101}$ is present, $X_{101}$=C; wherein $X_{102}$ is absent or present, and when $X_{102}$ is present, $X_{102}$=G, T, A or C; wherein $X_{103}$ is absent or present, and when $X_{103}$ is present, $X_{103}$=G, T, or A; wherein $X_{104}$ is absent or present, and when $X_{104}$ is present, $X_{104}$=T, C or G; wherein $X_{105}$ is absent or present, and when $X_{105}$ is present, $X_{105}$=T or G; wherein $X_{106}$ is absent or present, and when $X_{106}$ is present, $X_{106}$=T, A or G; wherein $X_{107}$ is absent or present, and when $X_{107}$ is present, $X_{107}$=T, A or C; wherein $X_{108}$ is absent or present, and when $X_{108}$ is present, $X_{108}$=A, G, T or C; wherein $X_{109}$ is absent or present, and when $X_{109}$ is present, $X_{109}$=A, T or G; wherein $X_{110}$ is absent or present, and when $X_{110}$ is present, $X_{110}$=C, T or G; wherein $X_{111}$ is absent or present, and when $X_{111}$ is present, $X_{111}$=T, or C; wherein $X_{112}$ is absent or present, and when $X_{112}$ is present, $X_{112}$=C, A, T or G; wherein $X_{113}$ is absent or present, and when $X_{113}$ is present, $X_{113}$=T, A or C; wherein $X_{114}$ is absent or present, and when $X_{114}$ is present, $X_{114}$=C, T or A; wherein $X_{115}$ is absent or present, and when $X_{115}$ is present, $X_{115}$=T, A, G or C;

wherein $X_{116}$ is absent or present, and when $X_{116}$ is present, $X_{116}$=A or C; wherein $X_{117}$ is absent or present, and when $X_{17}$ is present, $X_{117}$=C, T, G or A; wherein $X_{118}$ is absent or present, and when $X_{118}$ is present, $X_{118}$=G, A, C or T; wherein $X_{119}$ is absent or present, and when $X_{119}$ is present, $X_{119}$=G, C or T; wherein $X_{120}$ is absent or present, and when $X_{120}$ is present, $X_{120}$=C, A or T; wherein $X_{121}$ is absent or present, and when $X_{121}$ is present, $X_{121}$=T, A, C or G; wherein $X_{122}$ is absent or present, and when $X_{122}$ is present, $X_{122}$=A, G, C or T; wherein $X_{123}$ is absent or present, and when $X_{123}$ is present, $X_{123}$=A, G, C or T; wherein $X_{124}$ is absent or present, and when $X_{124}$ is present, $X_{124}$=C or G; wherein $X_{125}$ is absent or present, and when $X_{125}$ is present, $X_{125}$=C or T; wherein $X_{126}$ is absent or present, and when $X_{126}$ is present, $X_{126}$=T, G or C; wherein $X_{127}$ is absent or present, and when $X_{127}$ is present, $X_{127}$=G, C or T; wherein $X_{128}$ is absent or present, and when $X_{128}$ is present, $X_{128}$=G; wherein $X_{129}$ is absent or present, and when $X_{129}$ is present, $X_{129}$=T; wherein $X_{130}$ is absent or present, and when $X_{130}$ is present, $X_{130}$=C; wherein $X_{131}$ is absent or present, and when $X_{131}$ is present, $X_{131}$=A; wherein $X_{132}$ is absent or present, and when $X_{132}$ is present, $X_{132}$=T; wherein $X_{133}$ is absent or present, and when $X_{133}$ is present, $X_{133}$=C; wherein $X_{134}$ is absent or present, and when $X_{134}$ is present, $X_{134}$=A; wherein $X_{135}$ is absent or present, and when $X_{135}$ is present, $X_{135}$=A; wherein $X_{136}$ is absent or present, and when $X_{136}$ is present, $X_{136}$=T; wherein $X_{137}$ is absent or present, and when $X_{137}$ is present, $X_{137}$=C; wherein $X_{138}$ is absent or present, and when $X_{138}$ is present, $X_{138}$=T; wherein $X_{139}$ is absent or present, and when $X_{139}$ is present, $X_{139}$=C; wherein $X_{140}$ is absent or present, and when $X_{140}$ is present, $X_{140}$=A; wherein $X_{141}$ is absent or present, and when $X_{141}$ is present, $X_{141}$=C; wherein $X_{142}$ is absent or present, and when $X_{142}$ is present, $X_{142}$=G; wherein $X_{143}$ is absent or present, and when $X_{143}$ is present, $X_{143}$=T; wherein $X_{144}$ is absent or present, and when $X_{144}$ is present, $X_{144}$=C; wherein $X_{145}$ is absent or present, and when $X_{145}$ is present, $X_{145}$=C; wherein $X_{146}$ is absent or present, and when $X_{146}$ is present, $X_{146}$=A, G, C or T; wherein $X_{147}$ is absent or present, and when $X_{147}$ is present, $X_{147}$=A, T, C or G; wherein $X_{148}$ is absent or present, and when $X_{148}$ is present, $X_{148}$=T, A, C or G; wherein $X_{149}$ is absent or present, and when $X_{149}$ is present, $X_{149}$=G, C, or A; wherein $X_{150}$ is absent or present, and when $X_{150}$ is present, $X_{150}$=G, C, A or T; wherein $X_{151}$ is absent or present, and when $X_{151}$ is present, $X_{151}$=A, C or T; wherein $X_{152}$ is absent or present, and when $X_{152}$ is present, $X_{152}$=C, G or T; wherein $X_{153}$ is absent or present, and when $X_{153}$ is present, $X_{153}$=T or C; wherein $X_{154}$ is absent or present, and when $X_{154}$ is present, $X_{154}$=A, T, G or C; wherein $X_{155}$ is absent or present, and when $X_{155}$ is present, $X_{155}$=C or T; wherein $X_{156}$ is absent or present, and when $X_{156}$ is present, $X_{156}$=G, T, A or C; wherein $X_{157}$ is absent or present, and when $X_{157}$ is present, $X_{157}$=A or G; wherein $X_{158}$ is absent or present, and when $X_{158}$ is present, $X_{158}$=C or T; wherein $X_{159}$ is absent or present, and when $X_{159}$ is present, $X_{159}$=A, T or G; wherein $X_{160}$ is absent or present, and when $X_{160}$ is present, $X_{160}$=T, A, C or G; wherein $X_{161}$ is absent or present, and when $X_{161}$ is present, $X_{161}$=A or T; wherein $X_{162}$ is absent or present, and when $X_{162}$ is present, $X_{162}$=G, T or A; wherein $X_{163}$ is absent or present, and when $X_{163}$ is present, $X_{163}$=A; wherein $X_{164}$ is absent or present, and when $X_{164}$ is present, $X_{164}$=C; wherein $X_{165}$ is absent or present, and when $X_{165}$ is present, $X_{165}$=G or A; wherein $X_{166}$ is absent or present, and when $X_{166}$ is present, $X_{166}$=C; wherein $X_{167}$ is absent or present, and when $X_{167}$ is present, $X_{167}$=T; wherein $X_{168}$ is absent or present, and when $X_{168}$ is present, $X_{168}$=C; wherein $X_{169}$ is absent or present, and when $X_{169}$ is present, $X_{169}$=G or A; wherein $X_{170}$ is absent or present, and when $X_{170}$ is present, $X_{170}$=T, G or A; wherein $X_{171}$ is absent or present, and when $X_{17}$ is present, $X_{171}$=C or T; wherein $X_{172}$ is absent or present, and when $X_{172}$ is present, $X_{172}$=T or C; wherein $X_{173}$ is absent or present, and when $X_{173}$ is present, $X_{173}$=A, G or T; wherein $X_{174}$ is absent or present, and when $X_{174}$ is present, $X_{174}$=G, A or T; wherein $X_{175}$ is absent or present, and when $X_{175}$ is present, $X_{175}$=T, C or A; wherein $X_{176}$ is absent or present, and when $X_{176}$ is present, $X_{176}$=C or T; wherein $X_{177}$ is absent or present, and when $X_{177}$ is present, $X_{177}$=C, A or T; wherein $X_{178}$ is absent or present, and when $X_{178}$ is present, $X_{178}$=G, A or C; wherein $X_{179}$ is absent or present, and when $X_{179}$ is present, $X_{179}$=C, A or T; wherein $X_{180}$ is absent or present, and when $X_{180}$ is present, $X_{180}$=C or T; wherein $X_{181}$ is absent or present, and when $X_{181}$ is present, $X_{181}$=A, C, G or T; wherein $X_{182}$ is absent or present, and when $X_{182}$ is present, $X_{182}$=A, T or C; wherein $X_{183}$ is absent or present, and when $X_{183}$ is present, $X_{183}$=G, T, A, or C; wherein $X_{184}$ is absent or present, and when $X_{184}$ is present, $X_{184}$=G, C or A; wherein $X_{185}$ is absent or present, and when $X_{185}$ is present, $X_{185}$=C or T; wherein $X_{186}$ is absent or present, and when $X_{186}$ is present, $X_{186}$=C, T or A; wherein $X_{187}$ is absent or present, and when $X_{187}$ is present, $X_{187}$=A or G; wherein $X_{188}$ is absent or present, and when $X_{188}$ is present, $X_{188}$=C or T; wherein $X_{189}$ is absent or present, and when $X_{189}$ is present, $X_{189}$=C, A or T; wherein $X_{190}$ is absent or present, and when $X_{190}$ is present, $X_{190}$=A, T, A or G; wherein $X_{191}$ is absent or present, and when $X_{191}$ is present, $X_{191}$=T, G, or A; wherein $X_{192}$ is absent or present, and when $X_{192}$ is present, $X_{192}$=A or T; wherein $X_{193}$ is absent or present, and when $X_{193}$ is present, $X_{193}$=T, or A; wherein $X_{194}$ is absent or present, and when $X_{194}$ is present, $X_{194}$=A or G; wherein $X_{195}$ is absent or present, and when $X_{195}$ is present, $X_{195}$=G, A, or T; wherein $X_{196}$ is absent or present, and when $X_{196}$ is present, $X_{196}$=G or T; wherein $X_{197}$ is absent or present, and when $X_{197}$ is present, $X_{197}$=T, C, or A; wherein $X_{198}$ is absent or present, and when $X_{198}$ is present, $X_{198}$=A or G; wherein $X_{199}$ is absent or present, and when $X_{199}$ is present, $X_{199}$=T or C; wherein $X_{200}$ is absent or present, and when $X_{200}$ is present, $X_{200}$=G, T, A or C; wherein $X_{201}$ is absent or present, and when $X_{201}$ is present, $X_{201}$=G, T or A; wherein $X_{202}$ is absent or present, and when $X_{202}$ is present, $X_{202}$=G, C or A; wherein $X_{203}$ is absent or present, and when $X_{203}$ is present, $X_{203}$=C or T; wherein $X_{204}$ is absent or present, and when $X_{204}$ is present, $X_{204}$=A or T; wherein $X_{205}$ is absent or present, and when $X_{205}$ is present, $X_{205}$=A, C or G; wherein $X_{206}$ is absent or present, and when $X_{206}$ is present, $X_{206}$=C or A; wherein $X_{207}$ is absent or present, and when $X_{207}$ is present, $X_{207}$=A or G; wherein $X_{208}$ is absent or present, and when $X_{208}$ is present, $X_{208}$=C; wherein $X_{209}$ is absent or present, and when $X_{209}$ is present, $X_{209}$=C; wherein $X_{210}$ is absent or present, and when $X_{210}$ is present, $X_{210}$=C or T; wherein $X_{211}$ is absent or present, and when $X_{211}$ is present, $X_{211}$=A or G; wherein $X_{212}$ is absent or present, and when $X_{212}$ is present, $X_{212}$=C or A; wherein $X_{213}$ is absent or present, and when $X_{213}$ is present, $X_{213}$=C or A; wherein $X_{214}$ is absent or present, and when $X_{214}$ is present, $X_{214}$=G; wherein $X_{215}$ is absent or present, and when $X_{215}$ is present, $X_{215}$=A; wherein $X_{216}$ is absent or present, and when $X_{216}$ is present, $X_{216}$=G; wherein $X_{217}$ is absent or present, and when $X_{217}$ is present, $X_{217}$=C; wherein $X_{218}$ is absent or present, and when $X_{218}$ is present, $X_{218}$=G; wherein $X_{219}$ is absent or present, and when $X_{219}$ is present, $X_{219}$=C; wherein $X_{220}$ is absent or present, and when $X_{220}$ is present, $X_{220}$=T; wherein $X_{221}$ is absent or present, and when $X_{221}$ is present, $X_{221}$=T; wherein $X_{222}$ is absent or present, and when $X_{222}$ is present, $X_{222}$=C; wherein $X_{223}$ is absent or present, and when $X_{223}$ is present, $X_{223}$=G; wherein $X_{224}$ is absent or present, and when $X_{224}$ is present, $X_{224}$=T; wherein $X_{225}$ is absent or present, and when $X_{225}$ is present, $X_{225}$=C; wherein $X_{226}$ is absent or present, and when $X_{226}$ is present, $X_{226}$=G; wherein $X_{227}$ is absent or present, and when $X_{227}$ is present, $X_{227}$=A; wherein $X_{228}$ is absent or present, and when $X_{228}$ is present, $X_{228}$=G; wherein $X_{229}$ is absent or present, and when $X_{229}$ is present, $X_{229}$=G; wherein $X_{230}$ is absent or present, and when $X_{230}$ is present, $X_{230}$=C; wherein $X_{231}$ is absent or present, and when $X_{231}$ is present, $X_{231}$=C; wherein $X_{232}$ is absent or present, and when $X_{232}$ is present, $X_{232}$=A; wherein $X_{233}$ is absent or present, and when $X_{233}$ is present, $X_{233}$=C; wherein $X_{234}$ is absent or present, and when $X_{234}$ is present, $X_{234}$=C (SEQ ID NO: 81).

2. The engineered subgenomic promoter library of paragraph 1, wherein the library comprises subgenomic promoter sequences set forth in SEQ ID NO: 1-74.
3. An engineered subgenomic promoter library comprising a plurality of promoters, wherein each promoter comprises a nucleic acid sequence at least 70% identical to nucleic acid sequences of SEQ IDs NO: 1-74 and 81.
4. The engineered subgenomic promoter library of any one of paragraphs 1-3, wherein the promoter is a subgenomic promoter derived from an alphavirus.
5. The engineered subgenomic promoter library of paragraph 4, wherein the alphavirus is Venezuela Equine Encephalitis virus, Semliki Forest virus, or Sindbis virus.
6. The engineered subgenomic promoter library of any one of paragraphs 1-5, wherein each of the subgenomic promoters further comprises restriction endonuclease sites at the 5' and 3' ends.
7. The engineered subgenomic promoter library of paragraph 6, wherein the restriction endonuclease site at the 5' and 3' ends are SapI sites.
8. The engineered subgenomic promoter library of any one of paragraphs 1-7, wherein the library comprises engineered subgenomic promoters having differential activities.
9. An engineered nucleic acid comprising: (i) a promoter selected from the engineered subgenomic promoter library of any one of paragraphs 1-8; and (ii) a transgene operably linked to the promoter of (i).
10. The engineered nucleic acid of paragraph 9, wherein the first transgene encodes for a therapeutic molecule or a detectable molecule.
11. The engineered nucleic acid of paragraph 10, wherein the first transgene encodes for a heavy chain or a light chain of an antibody.
12. An expression cassette comprising one or more engineered nucleic acid of any one of paragraphs 7-9.
13. The expression cassette of paragraph 12, wherein the expression cassette is an antibody expression cassette.
14. An antibody expression cassette, comprising a first engineered nucleic acid comprising a first engineered subgenomic promoter selected from the engineered subgenomic promoter library of paragraph 1 operably linked to a first transgene, wherein the first transgene encodes a heavy chain of an antibody; and a second engineered nucleic acid comprising a second engineered subgenomic promoter selected from the engineered subgenomic promoter library of paragraph 1 operably linked to a second transgene, wherein the second transgene encodes a light chain of an antibody.
15. A vector comprising one or more engineered nucleic acid of any one of paragraphs 9-11, one or more expression cassette of any one of paragraphs 12-13, or the antibody expression cassette of paragraph 14.
16. The vector of paragraph 15, wherein the vector is a plasmid, RNA replicon, linear double stranded DNA, viral vectors, liposome or nanoparticles.
17. The vector of paragraph 16, wherein the RNA replicon is derived from an alphavirus.
18. The vector of paragraph 17, wherein the one or more engineered nucleic acid is located at the subgenomic region of the RNA replicon.
19. A cell comprising the engineered nucleic acid of any one of paragraphs 9-11, expression cassette of any one of paragraphs 12-13, the antibody expression cassette of paragraph 14, or the vectors of any one of paragraphs 15-18.
20. A method for selecting an antibody expression cassette for optimized production of functional antibody comprising: constructing an antibody expression cassette library comprising a plurality of antibody expression cassette for expression of a heavy chain and a light chain of an antibody, wherein the antibody expression cassette comprises: a first engineered nucleic acid comprising a first engineered subgenomic promoter selected from the engineered subgenomic promoter library of paragraph 1 operably linked to a first transgene, wherein the first transgene encodes a heavy chain of an antibody; and a second engineered nucleic acid comprising a second engineered subgenomic promoter selected from the engineered subgenomic promoter library of paragraph 1 operably linked to a second transgene, wherein the second transgene encodes a light chain of an antibody; delivering the plurality of engineered nucleic acids to a population of cells; culturing the cell under conditions allowing for expression of the heavy chain and the light chain of the antibody; measuring a level of functional antibody comprising the heavy chain and the light chain produced by population of cells; selecting cell(s) expressing optimal level of functional antibody; and determining the nucleic acid sequence of the subgenomic promoter in the first engineered nucleic acid and the nucleic acid sequence of the subgenomic promoter in the second engineered nucleic acid.
21. A method for producing an antibody, comprising: constructing an antibody expression cassette for expression of a heavy chain and a light chain of an antibody, wherein the antibody expression cassette comprises: a first engineered nucleic acid comprising a first engineered subgenomic promoter selected from the engineered subgenomic promoter library of paragraph 1 operably linked to a first transgene, wherein the first transgene encodes a heavy chain of an antibody; and a second engineered nucleic acid comprising a second engineered subgenomic promoter selected from the engineered subgenomic promoter library of paragraph 1 operably linked to a second transgene, wherein the second transgene encodes a light chain of an antibody; delivering the antibody expression cassette to a population of cells or a host animal; culturing the cell or growing the host animal under conditions allowing for expression of the heavy chain and the light chain of the antibody; and harvesting the cultured host cell, culture medium or tissue from the host animal for collection of the antibody.

22. The method of paragraph 21, further comprising purifying the antibody.
23. A method for producing one or more molecules, comprising: constructing an expression cassette for expression of the one or more molecules, wherein the expression cassette comprises one or more engineered nucleic acids of paragraphs 9-11, delivering the expression cassette to a population of cells or a host animal; culturing the cell or growing the host animal under conditions allowing for expression of the one or more molecules; and harvesting the cultured host cell, culture medium or tissue from the host animal for collection of the molecule.
24. The method of paragraph 23, further comprising purifying the molecule.
25. The method of any one of paragraphs 23 or 24, wherein the molecule encoded by the transgene is a detectable molecule or a therapeutic molecule.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B." or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. An engineered subgenomic promoter library comprising a plurality of promoters, wherein each promoter comprises a nucleic acid sequence at least 70% identical to nucleic acid sequences of SEQ ID NOs: 1, 3-13, 15-22, 24-40, 43, 44, 46-50, 52-56, and 58-74.

2. The engineered subgenomic promoter library of claim 1, wherein the promoter is a subgenomic promoter derived from an alphavirus.

3. The engineered subgenomic promoter library of claim 2, wherein the alphavirus is Venezuela Equine Encephalitis virus, Semliki Forest virus, or Sindbis virus.

4. The engineered subgenomic promoter library of claim 1, wherein each of the subgenomic promoters further comprises restriction endonuclease sites at the 5' and 3' ends.

5. The engineered subgenomic promoter library of claim 1, wherein the library comprises engineered subgenomic promoters having differential activities.

6. An engineered nucleic acid comprising:

(i) a promoter, wherein the promoter comprises a nucleic acid sequence at least 70% identical to nucleic acid sequences of SEQ ID NOs: 1, 3-13, 15-22, 24-40, 43, 44, 46-50, 52-56, and 58-74, wherein the promoter is less than 200 nucleotides long; and (ii) a transgene operably linked to the promoter of (i).

7. The engineered nucleic acid of claim 6, wherein the transgene encodes for a therapeutic molecule or a detectable molecule.

8. The engineered nucleic acid of claim 7, wherein the transgene encodes for a heavy chain or a light chain of an antibody.

9. An expression cassette comprising one or more engineered nucleic acid of claim 6.

10. The expression cassette of claim 9, wherein the expression cassette is an antibody expression cassette.

11. An antibody expression cassette, comprising a first engineered nucleic acid comprising a first engineered subgenomic promoter, wherein the promoter comprises a nucleic acid sequence at least 70% identical to nucleic acid sequences of SEQ ID NOs: 1, 3-13, 15-22, 24-40, 43, 44, 46-50, 52-56, and 58-74 wherein the promoter is less than 200 nucleotides long operably linked to a first transgene, wherein the first transgene encodes a heavy chain of an antibody; and a second engineered nucleic acid comprising a second engineered subgenomic promoter, wherein the promoter comprises a nucleic acid sequence at least 70% identical to nucleic acid sequences of SEQ ID NOs: 1, 3-13, 15-22, 24-40, 43, 44, 46-50, 52-56, and 58-74 wherein the promoter is less than 200 nucleotides long operably linked to a second transgene, wherein the second transgene encodes a light chain of an antibody.

12. A vector comprising one or more engineered nucleic acid of claim 6.

13. The vector of claim 12, wherein the vector is a plasmid, RNA replicon, linear double stranded DNA, viral vector, liposome, or nanoparticle.

14. The vector of claim 13, wherein the one or more engineered nucleic acid is located at the subgenomic region of the RNA replicon.

15. A cell comprising the engineered nucleic acid of claim 6.

16. The antibody expression cassette of claim 11, wherein the first engineered subgenomic promoter and the second engineered subgenomic promoter have differential activities.

17. A vector comprising the antibody expression cassette of claim 11.

18. The vector of claim 17, wherein the vector is a plasmid, RNA replicon, linear double stranded DNA, viral vector, liposome, or nanoparticle.

19. A cell comprising the antibody expression cassette of claim 11.

20. The engineered subgenomic promoter library of claim 1, wherein the library comprises subgenomic promoter sequences set forth in SEQ ID NOs: 1, 3-13, 15-22, 24-40, 43, 44, 46-50, 52-56, and 58-74.

* * * * *